United States Patent
Manfredi et al.

(10) Patent No.: US 10,973,834 B2
(45) Date of Patent: Apr. 13, 2021

(54) EP4 INHIBITORS AND USE THEREOF

(71) Applicants: Arrys Therapeutics, Inc., Boston, MA (US); AskAt Inc., Nagoya (JP)

(72) Inventors: Mark Manfredi, Boston, MA (US); Jeffrey Ecsedy, Boston, MA (US); Atsushi Nagahisa, Nagoya (JP); Yukinori Take, Nagoya (JP); Takako Okumura, Nagoya (JP)

(73) Assignees: Arrys Therapeutics, Inc., Boston, MA (US); AskAt Inc., Nagoya (JP)

(*) Notice: Subject to any disclaimer, the term of this patent is extended or adjusted under 35 U.S.C. 154(b) by 0 days.

(21) Appl. No.: 16/385,524

(22) Filed: Apr. 16, 2019

(65) Prior Publication Data

US 2019/0314390 A1    Oct. 17, 2019

Related U.S. Application Data

(60) Provisional application No. 62/737,219, filed on Sep. 27, 2018, provisional application No. 62/658,494, filed on Apr. 16, 2018.

(51) Int. Cl.

| | | |
|---|---|---|
| *A61K 31/64* | (2006.01) | |
| *A61K 38/20* | (2006.01) | |
| *A61K 39/395* | (2006.01) | |
| *A61K 35/00* | (2006.01) | |
| *A61K 31/44* | (2006.01) | |
| *A61K 35/26* | (2015.01) | |
| *C07K 16/28* | (2006.01) | |
| *A61K 39/00* | (2006.01) | |
| *A61P 35/00* | (2006.01) | |

(52) U.S. Cl.
CPC .............. *A61K 31/64* (2013.01); *A61K 31/44* (2013.01); *A61K 35/26* (2013.01); *A61K 38/208* (2013.01); *A61K 39/39541* (2013.01); *A61P 35/00* (2018.01); *C07K 16/2818* (2013.01); *A61K 2039/505* (2013.01); *C07K 2317/24* (2013.01)

(58) Field of Classification Search
CPC ................................ A61K 31/64; A61P 35/00
USPC .......................................................... 514/303
See application file for complete search history.

(56) References Cited

U.S. PATENT DOCUMENTS

| | | | |
|---|---|---|---|
| 6,710,054 B2 | 3/2004 | Nakao et al. | |
| 7,141,580 B2 | 11/2006 | Nakao et al. | |
| 7,238,714 B2 | 7/2007 | Nakao et al. | |
| 7,479,564 B2 | 1/2009 | Nakao et al. | |
| 7,960,407 B2 | 6/2011 | Haruta et al. | |
| 8,921,391 B2* | 12/2014 | Take | A61K 31/192 514/303 |
| 9,265,756 B2 | 2/2016 | Newbold et al. | |
| 9,457,084 B2 | 10/2016 | Kanazawa et al. | |
| 9,688,674 B2* | 6/2017 | Take | A61K 31/44 |
| 10,342,785 B2* | 7/2019 | Ohtani | A61K 31/44 |
| 10,391,086 B2 | 8/2019 | Okumura | |
| 10,583,129 B2* | 3/2020 | Ohtani | A61K 31/192 |
| 10,611,761 B2* | 4/2020 | Take | C07D 213/82 |
| 2017/0253595 A1 | 9/2017 | Take et al. | |
| 2017/0360764 A1 | 12/2017 | Okumura | |
| 2019/0269663 A1 | 9/2019 | Ohtani et al. | |
| 2019/0365680 A1 | 12/2019 | Ohtani et al. | |

FOREIGN PATENT DOCUMENTS

| | | | | |
|---|---|---|---|---|
| CA | | 3029611 A1 * | 1/2018 | ........... A61K 31/277 |
| EP | | 2422779 A1 | 7/2019 | |
| WO | WO 2002032900 A2 | | 4/2002 | |
| WO | WO 2005021508 A1 | | 3/2005 | |
| WO | WO 2011102149 A1 | | 8/2011 | |
| WO | WO 2013090552 A1 | | 6/2013 | |
| WO | WO 2014148053 A1 | | 9/2014 | |
| WO | WO 2018084230 A1 | | 5/2018 | |
| WO | WO-2019204257 A1 | | 10/2019 | |
| WO | WO-2020014445 A1 | | 1/2020 | |
| WO | WO-2020014465 A1 | | 1/2020 | |
| WO | WO-20069288 A1 | | 4/2020 | |

OTHER PUBLICATIONS

Adams et al., "Big opportunities for small molecules in immuno-oncology," Nat Rev Drug Discov, 14(9):603-22 (Sep. 2015).
Bao et al., "Combination of EP4 antagonist and checkpoint inhibitors promotes anti-tumor effector T cells in preclinical tumor models," J Immunother Cancer, 3(Suppl 2):P350 (Nov. 2015).
Berge et al., "Pharmaceutical salts," J Pharm Sci, 66(1):1-19 (Jan. 1977).
Ji et al., "Modified toxicity probability interval design: a safer and more reliable method than the 3 + 3 design for practical phase I trials," J Clin Oncol 31(14):1785-91 (May 2013).
Majumder et al., "EP4 as a Therapeutic Target for Aggressive Human Breast Cancer," Int J Mol Sci, 19(4) (Mar. 2018).
Partial International Search Report and Provisional Opinion of the International Searching Authority in PCT/US2019/027603, dated Aug. 14, 2019 (15 pages).
Toogood, "Small molecule immuno-oncology therapeutic agents," Bioorg Med Chem Lett, 28(3):319-329 (Feb. 2018).

* cited by examiner

*Primary Examiner* — Kevin E Weddington
(74) *Attorney, Agent, or Firm* — Dechert LLP; Andrea L. C. Reid; Gang Wang

(57) ABSTRACT

The present invention provides use of an agent that inhibits EP4 activity and an immuno-oncology agent, or a composition thereof, for treatment of a cancer.

20 Claims, 7 Drawing Sheets

EP4 INHIBITORS AND USE THEREOF

TECHNICAL FIELD OF THE INVENTION

The present invention relates to EP4 inhibitors, and the use thereof in combination with an immuno-oncology agent for treatment of a proliferative disorder.

BACKGROUND OF THE INVENTION

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis or the like.

Four $PGE_2$ receptor subtypes (EP1, EP2, EP3 and EP4) displaying different pharmacological properties exist. The EP4 subtype, a Gs-coupled receptor, stimulates cAMP production as well as PI3K and GSK3β signaling, and is distributed in a wide variety of tissue suggesting a major role in $PGE_2$-mediated biological events. Various EP4 inhibitors have been described previously, for example, in WO 2002/032900, WO 2005/021508, U.S. Pat. Nos. 6,710,054, and 7,238,714, the contents of which are incorporated herein by reference in their entireties.

Immuno-oncology seeks to enlist the body's immune system to combat the growth of malignant tumors. Examples of immuno-oncology agents are discussed, for example, in *Nature Reviews Drug Discovery* 14 (2015) 603-622 and *Bioorganic & Medicinal Chemistry Letters* 28 (2018) 319-329, the contents of which are incorporated herein by reference in their entireties.

SUMMARY OF THE INVENTION

It has now been found that an EP4 inhibitor can be used in combination with immuno-oncology agents for treatment of proliferative disorders including cancer. In one aspect, the present invention provides a method for treating a proliferative disorder in a patient comprising administering to the patient an agent that inhibits prostaglandin EP4 receptor (EP4) activity, and an immuno-oncology agent. Examples of agents that inhibit EP4 activity, immuno-oncology agents, and proliferative disorders are described herein.

DETAILED DESCRIPTION OF CERTAIN EMBODIMENTS

Figure 1:
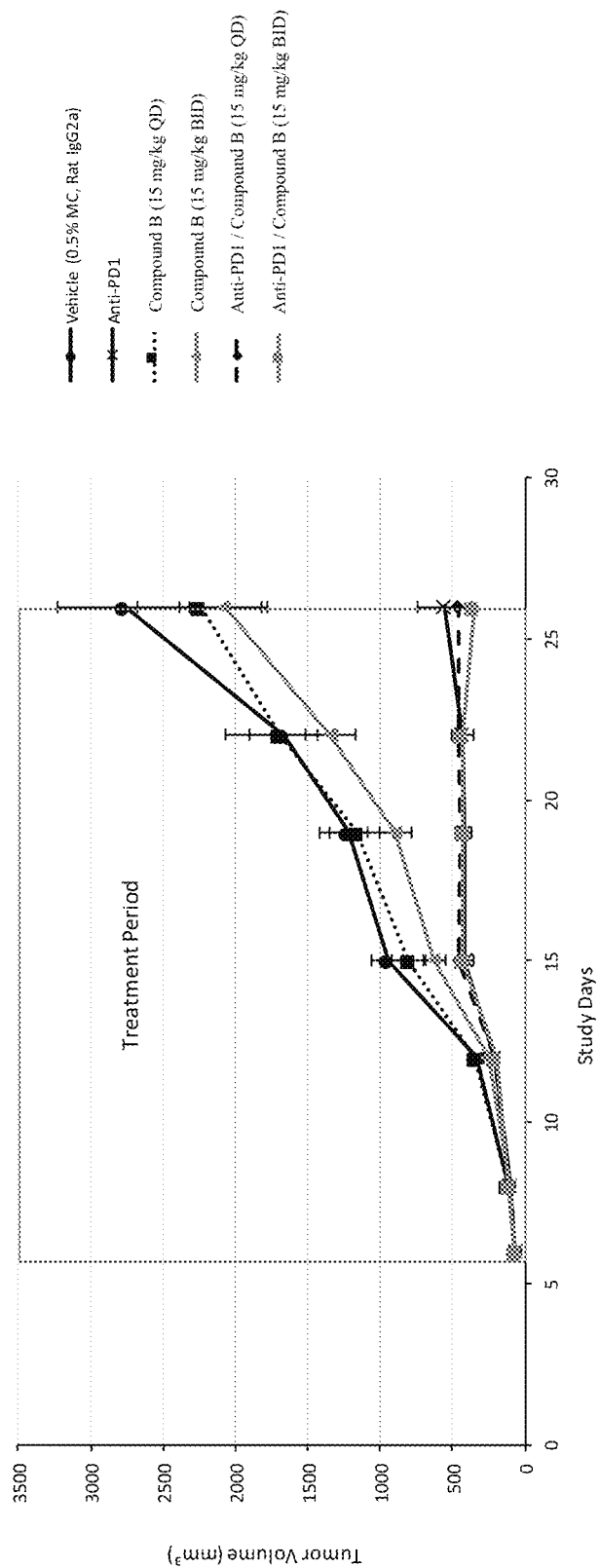
FIG. 1 depicts Growth Kinetics in BALB/C Mice Bearing CT-26 Tumors. BALB/C mice bearing CT-26 tumors were treated with vehicle (0.5% methylcellulose and IgG2a), anti-PD-1, or Compound B at 15 mg/kg QD and BID alone or in combination with anti-PD-1. Mean tumor volumes ($mm^3$) and standard error of the mean (n=10/group) are shown.

1. General Description of Certain Embodiments of the Invention

In one aspect, the present invention provides a method for treating a proliferative disorder in a patient comprising administering to the patient an agent that inhibits prostaglandin EP4 receptor (EP4) activity, and an immuno-oncology agent. In some embodiments, an agent that inhibits EP4 activity is a selective EP4 inhibitor. In some embodiments, an immuno-oncology agent is a PD-1 inhibitor. In some embodiments, a proliferative disorder is as described herein. In some embodiments, a proliferative disorder is a NSCLC subject that has been previously treated for more than 12 weeks with any PD-1 or PD-L1 checkpoint inhibitor. In some embodiments, a proliferative disorder is a CRC patient who has MSS disease. In some embodiments, an agent that inhibits prostaglandin EP4 receptor (EP4) activity is compound A, or a pharmaceutically acceptable salt thereof. In some embodiments, an agent that inhibits prostaglandin EP4 receptor (EP4) activity is compound B, or a pharmaceutically acceptable salt thereof.

2. Exemplary Agents that Inhibit EP4 Activity

2.1. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

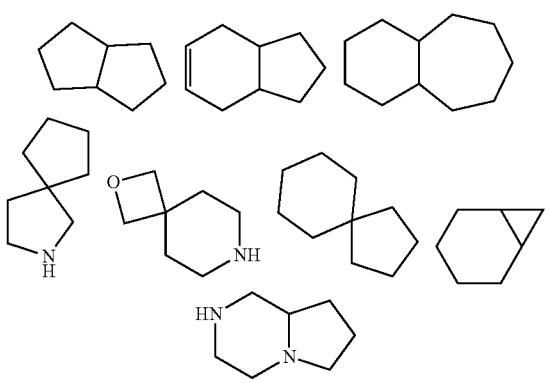

Exemplary bridged bicyclics include:

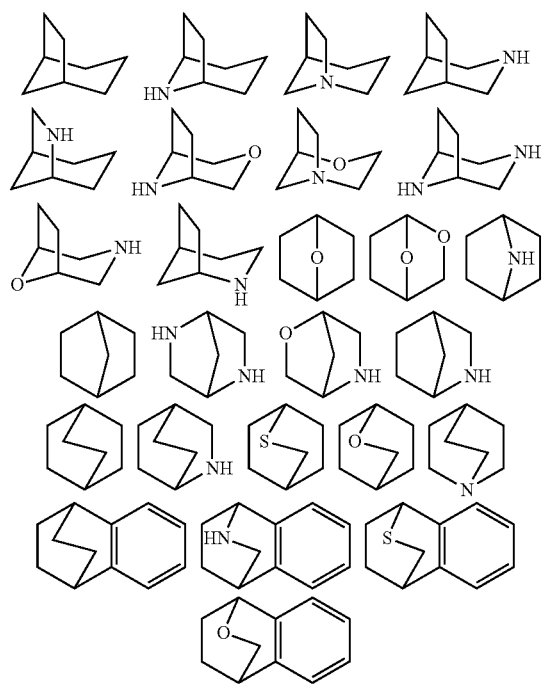

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

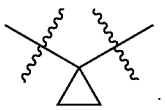 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —(CH$_2$)$_{0-4}$R°; —(CH$_2$)$_{0-4}$OR°; —O(CH$_2$)$_{0-4}$R, —O—(CH$_2$)$_{0-4}$C(O)OR°; —(CH$_2$)$_{0-4}$CH(OR°)$_2$; —(CH$_2$)$_{0-4}$SR°;

—(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR)R°; —C(O)C(O)R°; —C(O)CH$_2$C(O)R; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —S(O)(NR)R°; —S(O)$_2$N=C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$.

Each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from =O and =S; or each R° is optionally substituted with a monovalent substituent independently selected from halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$.

Each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, or a divalent substituent bound to vicinal substitutable carbons of an "optionally substituted" group is —O(CR$_2$)$_{2-3}$O—, wherein each independent occurrence of R* is selected from hydrogen, C$_{1-6}$ aliphatic or an unsubstituted 5-6-membered saturated, partially unsaturated, or aryl ring having 0-4 heteroatoms independently selected from nitrogen, oxygen, or sulfur.

When R* is C$_{1-6}$ aliphatic, R* is optionally substituted with halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

An optional substituent on a substitutable nitrogen is independently —R$^{\dagger}$, —NR$^{\dagger}$$_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$; wherein each R$^{\dagger}$ is independently hydrogen, C$_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R$^{\dagger}$ is C$_{1-6}$ aliphatic, R$^{\dagger}$ is optionally substituted with halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "an agent that inhibits EP4 activity" or "an EP4 inhibitor" refers to an agent that reduces or attenuates the biological activity of an EP4 receptor. Such agents may include proteins such as anti-EP4 antibodies, nucleic acids, amino acids, peptides carbohydrates, small molecules (organic or inorganic), or any other compound or composition which decreases the activity of an EP4 receptor either by reducing the amount of EP4 receptor present in a cell, or by decreasing the binding or signaling activity of the EP4 receptor.

As used herein, the term "EP4 receptor activity" or "EP4 activity" refers to an EP4-mediated increase in cAMP levels upon $PGE_2$ stimulation.

As used herein, the term "a selective EP4 inhibitor" is an agent that inhibits EP4 activity with an $IC_{50}$ at least 10-fold less, preferably, at least 100-fold less than the $IC_{50}$ for inhibition of EP1, EP2, or EP3 activity, as determined by standard methods known in the art.

As used herein, the term "measurable affinity" or "measurably inhibit" refers to a measurable change in EP4 activity between a sample comprising an EP4 inhibitor described herein, or a salt or a composition thereof, and EP4, and an equivalent sample comprising EP4, in the absence of said compound, or composition thereof.

2.2. Compounds of Formulae I, II, and III

In some embodiments, an agent that inhibits EP4 activity is a compound of formula I:

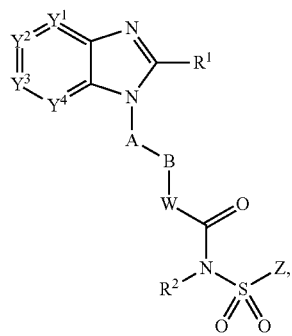

(I)

or a pharmaceutically acceptable salt thereof, wherein
$Y^1$, $Y^2$, $Y^3$ and $Y^4$ are independently selected from N, CH or C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

A is a 5-6 membered monocyclic aromatic ring optionally containing up to 3 heteroatoms selected from O, N and S, wherein said 5-6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C(=O)$—, HO(O=)C—, $C_{1-4}$alkyl-O(O=)C—, $C_{1-4}$ alkylsulfonylamino, $C_{3-7}$ cycloalkyl, $R^3C(=O)N(R^4)$— and $NH_2(HN=)C$—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;

$R^2$ is H, $C_{1-4}$ alkyl, OH or $C_{1-4}$ alkoxy;

Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3C(=O)N(R^4)$—, HO(O=)C, $C_{1-4}$alkyl-O(O=)C—, $C_{1-4}$ alkylsulfonylamino, $C_{3-7}$ cycloalkyl, $NH_2(HN=)C$—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{-1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $C_{1-4}$ alkyl sulfonylamino, $C_{3-7}$ cycloalkyl, $R^3C(=O)N(R^4)$—, $NH_2(HN=)C$—, $R^3N(R^4)C(=O)$—, $R^3N(R^4)S(O)m$—, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O=)C— or $C_{1-4}$ alkyl-O—(O=)C—; and $Q^2$ is a 5-12 membered monocyclic or bicyclic aromatic ring, or a 5-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-8}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl-(O=)C, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—.

As defined generally above, $Y^1$, $Y^2$, $Y^3$ and $Y^4$ are independently selected from N, CH or C(L).

In some embodiments, $Y^1$ is N. In some embodiments, $Y^1$ is CH. In some embodiments, $Y^1$ is C(L), wherein L is as defined in the embodiments described herein.

In some embodiments, $Y^2$ is N. In some embodiments, $Y^2$ is CH. In some embodiments, $Y^2$ is C(L), wherein L is as defined in the embodiments described herein.

In some embodiments, $Y^3$ is N. In some embodiments, $Y^3$ is CH. In some embodiments, $Y^3$ is C(L), wherein L is as defined in the embodiments described herein.

In some embodiments, $Y^4$ is N. In some embodiments, $Y^4$ is CH. In some embodiments, $Y^4$ is C(L), wherein L is as defined in the embodiments described herein.

In some embodiments, $Y^1$, $Y^2$, $Y^3$ and $Y^4$ are selected from:
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N; or
s) $Y^2$ is C(L), $Y^1$ and $Y^3$ are CH, and $Y^4$ is N.

In some embodiments, $Y^1$, $Y^2$, $Y^3$ and $Y^4$ are selected from:
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH; or
j) $Y^1$ and $Y^4$ are CH, and $Y^2$ and $Y^3$ are C(L).

In some embodiments, each of $Y^1$, $Y^2$, $Y^3$ and $Y^4$ is independently selected from those as depicted in Table 1.

As defined generally above, $R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—.

In some embodiments, $R^1$ is H. In some embodiments, $R^1$ is $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—, wherein each of $Q^1$, m, and $R^3$ is independently as defined in the embodiments described herein.

In some embodiments, $R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S—, $Q^1$-$C_{1-4}$ alkyl-O—, or $C_{1-4}$alkyl-C(O)—N($R^3$)—, wherein each of $Q^1$, $R^3$, and m is independently as defined in the embodiments described herein.

In some embodiments, $R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N($R^3$)—, wherein each of $Q^1$, $R^3$, and m is independently as defined in the embodiments described herein.

In some embodiments, $R^1$ is $C_{1-8}$ alkyl, optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, Q-$C_{1-4}$alkyl-O—, Q-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—, wherein each of $Q^1$, m, and $R^3$ is independently as defined in the embodiments described herein.

In some embodiments, $R^1$ is $C_{2-8}$ alkenyl, optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)

m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—, wherein each of $Q^1$, m, and $R^3$ is independently as defined in the embodiments described herein.

In some embodiments, $R^1$ is $C_{2-8}$ alkynyl, optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—, wherein each of $Q^1$, m, and $R^3$ is independently as defined in the embodiments described herein.

In some embodiments, $R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pynolidinyl, piperidyl, oxopyrrolidinyl, oxopiperidyl, $Q^1$-, or $C_{1-4}$alkyl-C(O)—N(H)—, wherein $Q^1$ is as defined in the embodiments described herein.

In some embodiments, $R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N($R^3$)—, wherein $R^3$ is as defined in the embodiments described herein.

In some embodiments, $R^1$ is $C_{3-7}$ cycloalkyl.

In some embodiments, $R^1$ is $C_{1-8}$ alkoxy.

In some embodiments, $R^1$ is halo-substituted $C_{1-8}$ alkoxy.

In some embodiments, $R^1$ is $C_{1-8}$ alkyl-S(O)m-, wherein m is as defined in the embodiments described herein.

In some embodiments, $R^1$ is $Q^1$-, wherein $Q^1$ is as defined in the embodiments described herein.

In some embodiments, $R^1$ is pyrrolidinyl.

In some embodiments, $R^1$ is piperidyl.

In some embodiments, $R^1$ is oxopyrrolidinyl.

In some embodiments, $R^1$ is oxopiperidyl.

In some embodiments, $R^1$ is amino.

In some embodiments, $R^1$ is mono- or di-($C_{1-8}$ alkyl) amino.

In some embodiments, $R^1$ is $C_{1-4}$alkyl-C(=O)—N($R^3$)—, wherein $R^3$ is as defined in the embodiments described herein.

In some embodiments, $R^1$ is $C_{1-4}$alkyl-S(O)m-N($R^3$)—, wherein each of m and $R^3$ is as defined in the embodiments described herein.

In some embodiments, $R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl.

In some embodiments, $R^1$ is selected from those depicted in Table 1.

As defined generally above, $Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—.

In some embodiments, $Q^1$ is a 5-12 membered monocyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—, wherein each of $R^3$ and $R^4$ is independently as defined in the embodiments described herein.

In some embodiments, $Q^1$ is a 5 or 6 membered monocyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—, wherein each of $R^3$ and $R^4$ is independently as defined in the embodiments described herein.

In some embodiments, $Q^1$ is a 5-12 membered bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—, wherein each of $R^3$ and $R^4$ is independently as defined in the embodiments described herein.

In some embodiments, $Q^1$ is a 8-10 membered bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—, wherein each of $R^3$ and $R^4$ is independently as defined in the embodiments described herein.

In some embodiments, $Q^1$ is a 5-12 membered monocyclic aromatic ring optionally containing up to 4 heteroatoms selected from N and S, and is optionally substituted with halo, $C_{1-4}$ alkyl, $C_{1-4}$ alkylsulfonyl or $C_{1-4}$ alkylC(=O)—.

In some embodiments, $Q^1$ is 5-12 membered monocyclic aromatic ring system optionally containing up to 2 heteroatoms selected from N and S.

In some embodiments, $Q^1$ is a 5 or 6 membered monocyclic aromatic ring optionally containing up to 4 heteroatoms selected from N and S.

In some embodiments, $Q^1$ is selected from those depicted in Table 1.

As defined generally above, A is a 5-6 membered monocyclic aromatic ring optionally containing up to 3 heteroatoms selected from O, N and S, wherein said 5-6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl) amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3$N($R^4$)C(=O)—, HO(O=)C—, $C_{1-4}$alkyl-O(O=)C—, $C_{1-4}$ alkylsulfonylamino, $C_{3-7}$ cycloalkyl, $R^3C(=O)N(R^4)$— and $NH_2(HN=)C$—.

In some embodiments, A is a 5 membered monocyclic aromatic ring optionally containing up to 3 heteroatoms selected from O, N and S, wherein said 5 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C(=O)$—, HO(O=)C—, $C_{1-4}$alkyl-O(O=)C—, $C_{1-4}$ alkylsulfonylamino, $C_{3-7}$ cycloalkyl, $R^3C(=O)N(R^4)$— and $NH_2(HN=)C$—, wherein each of $R^3$ and $R^4$ is independently as defined in the embodiments described herein.

In some embodiments, A is a 6 membered monocyclic aromatic ring optionally containing up to 3 heteroatoms selected from O, N and S, wherein said 6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C(=O)$—, HO(O=)C—, $C_{1-4}$alkyl-O(O=)C—, $C_{1-4}$ alkylsulfonylamino, $C_{3-7}$ cycloalkyl, $R^3C(=O)N(R^4)$— and $NH_2(HN=)C$—, wherein each of $R^3$ and $R^4$ is independently as defined in the embodiments described herein.

In some embodiments, A is a 5-6 membered monocyclic aromatic ring optionally containing up to 2 heteroatoms selected from O, N, and S, wherein said 5-6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy.

In some embodiments, A is 5-6 membered monocyclic aromatic ring optionally substituted with halo, $C_{1-4}$ alkyl or $C_{1-4}$ alkoxy.

In some embodiments, A is 5-6 membered monocyclic aromatic ring optionally substituted with halo or $C_{1-4}$ alkyl.

In some embodiments, A is 5-6 membered monocyclic aromatic ring.

In some embodiments, A is phenyl.

In some embodiments, A is selected from those depicted in Table 1.

As defined generally above, B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl.

In some embodiments, B is halo-substituted $C_{1-6}$ alkylene optionally substituted with an oxo group or $C_{1-3}$ alkyl.

In some embodiments, B is $C_{3-7}$ cycloalkylene optionally substituted with an oxo group or $C_{1-3}$ alkyl.

In some embodiments, B is $C_{2-6}$ alkenylene optionally substituted with an oxo group or $C_{1-3}$ alkyl.

In some embodiments, B is $C_{2-6}$ alkynylene optionally substituted with an oxo group or $C_{1-3}$ alkyl.

In some embodiments, B is —O—$C_{1-5}$ alkylene optionally substituted with an oxo group or $C_{1-3}$ alkyl.

In some embodiments, B is $C_{1-2}$ alkylene-O—$C_{1-2}$ alkylene optionally substituted with an oxo group or $C_{1-3}$ alkyl.

In some embodiments, B is $C_{1-6}$ alkylene optionally substituted with an oxo group or $C_{1-3}$ alkyl.

In some embodiments, B is $C_{3-7}$ cycloalkylene or $C_{1-6}$ alkylene optionally substituted with an oxo group or $C_{1-3}$ alkyl.

In some embodiments, B is $C_{1-3}$ alkylene optionally substituted with $C_{1-3}$ alkyl.

In some embodiments, B is $C_{1-2}$ alkylene optionally substituted with methyl.

In some embodiments, B is ethylene or propylene.

In some embodiments, B is selected from those depicted in Table 1.

As defined generally above, W is NH, N—$C_{1-4}$ alkyl, O, S, N—$OR^5$ or a covalent bond.

In some embodiments, W is NH, N—$C_{1-4}$ alkyl, O or N—OH.

In some embodiments, W is NH, N—$C_{1-2}$ alkyl or O.

In some embodiments, W is NH, N—$CH_3$ or O.

In some embodiments, W is NH.

In some embodiments, W is N—$C_{1-4}$ alkyl.

In some embodiments, W is O.

In some embodiments, W is S.

In some embodiments, W is N—$OR^5$, wherein $R^5$ is as defined in the embodiments described herein.

In some embodiments, W is a covalent bond.

In some embodiments, W is selected from those depicted in Table 1.

As defined generally above, $R^2$ is H, $C_{1-4}$ alkyl, OH or $C_{1-4}$ alkoxy.

In some embodiments, $R^2$ is H. In some embodiments, $R^2$ is $C_{1-4}$ alkyl, OH or $C_{1-4}$ alkoxy.

In some embodiments, $R^2$ is H or $C_{1-4}$ alkyl.

In some embodiments, $R^2$ is $C_{1-4}$ alkyl.

In some embodiments, $R^2$ is OH.

In some embodiments, $R^2$ is or $C_{1-4}$ alkoxy.

In some embodiments, $R^2$ is selected from those depicted in Table 1.

As defined generally above, Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3C(=O)N(R^4)$—, HO(O=)C, $C_{1-4}$alkyl-O(O=)C—, $C_{1-4}$ alkylsulfonylamino, $C_{3-7}$ cycloalkyl, $NH_2(HN=)C$—, $Q^2$-S(O)m-, $Q^2$-O—, $Q^2$-N($R^3$)— or $Q^2$-.

In some embodiments, Z is a 5 membered monocyclic aromatic ring optionally containing up to 3 heteroatoms selected from O, N and S, wherein said 5 membered monocyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3C(=O)N(R^4)$—, HO(O=)C, $C_{1-4}$alkyl-O(O=)C—, $C_{1-4}$ alkylsulfonylamino, $C_{3-7}$ cycloalkyl, $NH_2(HN=)C$—, $Q^2$-S(O)m-, $Q^2$-O—, $Q^2$-N($R^3$)— or $Q^2$-, wherein each of $R^3$, $R^4$, and $Q^2$ is independently as defined in the embodiments described herein.

In some embodiments, Z is a 6 membered monocyclic aromatic ring optionally containing up to 3 heteroatoms selected from O, N and S, wherein said 6 membered monocyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3$C(=O)N($R^4$)—, HO(O=)C, $C_{1-4}$alkyl-O(O=)C—, $C_{1-4}$ alkylsulfonylamino, $C_{3-7}$ cycloalkyl, $NH_2$(HN=)C—, $Q^2$-S(O)m-, $Q^2$-O—, $Q^2$-N($R^3$)— or $Q^2$-, wherein each of $R^3$, $R^4$, and $Q^2$ is independently as defined in the embodiments described herein.

In some embodiments, Z is a 8 membered bicyclic aromatic ring optionally containing up to 3 heteroatoms selected from O, N and S, wherein said 8 membered bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3$C(=O)N($R^4$)—, HO(O=)C, $C_{1-4}$alkyl-O(O=)C—, $C_{1-4}$ alkylsulfonylamino, $C_{3-7}$ cycloalkyl, $NH_2$(HN=)C—, $Q^2$-S(O)m-, $Q^2$-O—, $Q^2$-N($R^3$)— or $Q^2$-, wherein each of $R^3$, $R^4$, and $Q^2$ is independently as defined in the embodiments described herein.

In some embodiments, Z is a 9 membered bicyclic aromatic ring optionally containing up to 3 heteroatoms selected from O, N and S, wherein said 9 membered bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3$C(=O)N($R^4$)—, HO(O=)C, $C_{1-4}$alkyl-O(O=)C—, $C_{1-4}$ alkylsulfonylamino, $C_{3-7}$ cycloalkyl, $NH_2$(HN=)C—, $Q^2$-S(O)m-, $Q^2$-O—, $Q^2$-N($R^3$)— or $Q^2$-, wherein each of $R^3$, $R^4$, and $Q^2$ is independently as defined in the embodiments described herein.

In some embodiments, Z is a 10 membered bicyclic aromatic ring optionally containing up to 3 heteroatoms selected from O, N and S, wherein said 10 membered bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3$C(=O)N($R^4$)—, HO(O=)C, $C_{1-4}$alkyl-O(O=)C—, $C_{1-4}$ alkylsulfonylamino, $C_{3-7}$ cycloalkyl, $NH_2$(HN=)C—, $Q^2$-S(O)m-, $Q^2$-O—, $Q^2$-N($R^3$)— or $Q^2$-, wherein each of $R^3$, $R^4$, and $Q^2$ is independently as defined in the embodiments described herein.

In some embodiments, Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C-$C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-, wherein each of $R^3$, $R^4$, $Q^2$, and m is independently as defined in the embodiments described herein.

In some embodiments, Z is 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-, wherein each of $R^3$, $R^4$, $Q^2$, and m is independently as defined in the embodiments described herein.

In some embodiments, Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C, $Q^2$-S(O)m-, $Q^2$-O—, $Q^2$-N($R^3$)— or $Q^2$-, wherein each of $R^3$, $R^4$, $Q^2$, and m is independently as defined in the embodiments described herein.

In some embodiments, Z is 5-12 membered monocyclic or bicyclic aromatic ring optionally containing up to 3 heteroatoms selected from N and S, wherein said 5-12 membered monocyclic aromatic ring is optionally substituted with halo, $C_{1-4}$ alkyl, nitro, $R^3$C(=O)N($R^4$)— or $Q^2$-, wherein each of $R^3$, $R^4$, and $Q^2$ is independently as defined in the embodiments described herein.

In some embodiments, Z is 5-10 membered monocyclic or bicyclic aromatic ring optionally containing up to 3 heteroatoms selected from N and S, wherein said 5-10 membered monocyclic aromatic ring is optionally substituted with chloro, bromo, methyl, nitro, $CH_3$C(=O)NH—, tBuC(=O)NH— or phenyl.

In some embodiments, Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl.

In some embodiments, Z is selected from those depicted in Table 1.

As defined generally above, L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)—, $NH_2$(HN=)C—, $R^3$N($R^4$)C(=O)—, $R^3$N($R^4$)S(O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms.

In some embodiments, L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms, wherein each of $R^3$, $R^4$, $Q^2$, and m is independently as defined in the embodiments described herein.

In some embodiments, L is halo. In some embodiments, L is F. In some embodiments, L is Cl. In some embodiments, L is Br. In some embodiments, L is I.

In some embodiments, L is $C_{1-4}$ alkyl.

In some embodiments, L is halo-substituted $C_{1-4}$ alkyl.

In some embodiments, L is hydroxyl.
In some embodiments, L is $C_{1-4}$ alkoxy.
In some embodiments, L is halo-substituted $C_{1-4}$ alkoxy.
In some embodiments, L is $C_{1-4}$ alkylthio.
In some embodiments, L is nitro.
In some embodiments, L is amino.
In some embodiments, L is mono- or di-($C_{1-4}$ alkyl) amino.
In some embodiments, L is cyano.
In some embodiments, L is HO—$C_{-1-4}$ alkyl.
In some embodiments, L is $C_{1-4}$ alkoxy-$C_{1-4}$alkyl.
In some embodiments, L is $C_{1-4}$ alkylsulfonyl.
In some embodiments, L is aminosulfonyl.
In some embodiments, L is $C_{1-4}$alkylC(=O)—.
In some embodiments, L is HO(O=)C—.
In some embodiments, L is $C_{1-4}$alkyl-O(O=)C—.
In some embodiments, L is $C_{1-4}$ alkylsulfonylamino.
In some embodiments, L is $C_{3-7}$ cycloalkyl.
In some embodiments, L is $R^3C(=O)N(R^4)$—, wherein each of $R^3$ and $R^4$ is independently as defined in the embodiments described herein.
In some embodiments, L is $NH_2(HN=)C$—.
In some embodiments, L is $R^3N(R^4)C(=O)$—, wherein each of $R^3$ and $R^4$ is independently as defined in the embodiments described herein.
In some embodiments, L is $R^3N(R^4)S(O)m$-, wherein each of $R^3$, $R^4$, and m is independently as defined in the embodiments described herein.
In some embodiments, L is $Q^2$-, wherein $Q^2$ is as defined in the embodiments described herein.
In some embodiments, L is $Q^2$-C(=O)—, wherein $Q^2$ is as defined in the embodiments described herein.
In some embodiments, L is $Q^2$-O—, wherein $Q^2$ is as defined in the embodiments described herein.
In some embodiments, L is $Q^2$-$C_{1-4}$alkyl-O—, wherein $Q^2$ is as defined in the embodiments described herein.
In some embodiments, two adjacent L groups are optionally joined together to form an alkylene chain having 3 or 4 members in which one or two (non-adjacent) carbon atoms are optionally replaced by oxygen atoms.
In some embodiments, L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$-, $Q^2$-, $Q^2$-C(=O)—, or two adjacent L groups are joined together to form a methylenedioxy group, wherein each of $R^3$, $R^4$, $Q^2$, and m is independently as defined in the embodiments described herein.
In some embodiments, L is chloro, methyl, trifluoromethyl, hydroxy, methoxy, cyano, acetyl, —C(=O)$NH_2$, trifluoromethyloxy, methanesulfonyl, or 1-hydroxy-1-methyl-ethyl, or two adjacent L groups are joined together to form a methylenedioxy group.
In some embodiments, L is selected from those depicted in Table 1.
As defined generally above, m is 0, 1 or 2.
In some embodiments, m is 0 or 2.
In some embodiments, m is 0. In some embodiments, m is 1. In some embodiments, m is 2.
In some embodiments, m is selected from those depicted in Table 1.
As defined generally above, each of $R^3$ and $R^4$ is independently selected from H and $C_{1-4}$ alkyl.
In some embodiments, $R^3$ is H.
In some embodiments, $R^3$ is $C_{1-4}$ alkyl
In some embodiments, $R^4$ is H.
In some embodiments, $R^4$ is $C_{1-4}$ alkyl In some embodiments, each of $R^3$ and $R^4$ is independently selected from those depicted in Table 1.
As defined generally above, $R^5$ is H, $C_{1-4}$ alkyl, $C_{1-4}$ alkyl-(O=)C— or $C_{1-4}$ alkyl-O—(O=)C—.
In some embodiments, $R^5$ is H.
In some embodiments, $R^5$ is $C_{1-4}$ alkyl.
In some embodiments, $R^5$ is $C_{1-4}$ alkyl-(O=)C—.
In some embodiments, $R^5$ is $C_{1-4}$ alkyl-O—(O=)C—.
In some embodiments, $R^5$ is selected from those depicted in Table 1.
As defined generally above, $Q^2$ is a 5-12 membered monocyclic or bicyclic aromatic ring, or a 5-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-8}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl-(O=)C, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O) NH— or $NH_2(HN=)C$—.
In some embodiments, $Q^2$ is a 5-12 membered monocyclic or bicyclic aromatic ring, or a 8-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C, $C_{1-4}$ alkyl-O(O=)C—, $C_{1-4}$ alkylsulfonylamino, $C_{3-7}$ cycloalkyl or $C_{1-4}$ alkyl-C(=O)NH—, wherein each of $R^3$ and $R^4$ is independently as defined in the embodiments described herein.
In some embodiments, $Q^2$ is a 5-12 membered monocyclic or bicyclic aromatic ring, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-8}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl-(O=)C, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O) NH— or $NH_2(HN=)C$—, wherein $R^3$ and $R^4$ are as defined in the embodiments described herein.
In some embodiments, $Q^2$ is a 5 or 6 membered monocyclic aromatic ring, wherein said 5 or 6 membered monocyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-8}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl-(O=)C, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O) NH— or $NH_2(HN=)C$—, wherein $R^3$ and $R^4$ are as defined in the embodiments described herein.
In some embodiments, $Q^2$ is a 8-10 membered bicyclic aromatic ring, wherein said 8-10 membered bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-8}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl-(O=)C, $R^3(R^4)C(=O)N-$, $HO(O=)C-$, $C_{1-4}$ alkyl-O(O=)C-, $C_{1-4}$ alkylsulfonylamino, $C_{3-7}$ cycloalkyl, $C_{1-4}$ alkyl-C(=O)NH— or $NH_2(HN=)C-$, wherein $R^3$ and $R^4$ are as defined in the embodiments described herein.

In some embodiments, $Q^2$ is a 5-12 membered tricyclic ring optionally containing up to 3 heteroatoms selected from O, N and S.

In some embodiments, $Q^2$ is a 5 or 6 membered monocyclic aromatic ring, or a 8-12 membered tricyclic ring containing up to 3 heteroatoms selected from N and S, wherein said 5 or 6 membered monocyclic aromatic ring is optionally substituted with halo.

In some embodiments, $Q^2$ is a 5 or 6 membered monocyclic aromatic ring or a 8-12 membered tricyclic ring optionally containing 1 sulfur atom wherein said 5 or 6 membered mono cyclic aromatic ring is optionally substituted with halo.

In some embodiments, $Q^2$ is a 5 or 6 membered monocyclic aromatic ring.

In some embodiments, $Q^2$ is selected from those as depicted in Table 1.

In some embodiments, a compound of formula I is a compound depicted in Table 1, or a pharmaceutically acceptable salt thereof.

TABLE 1

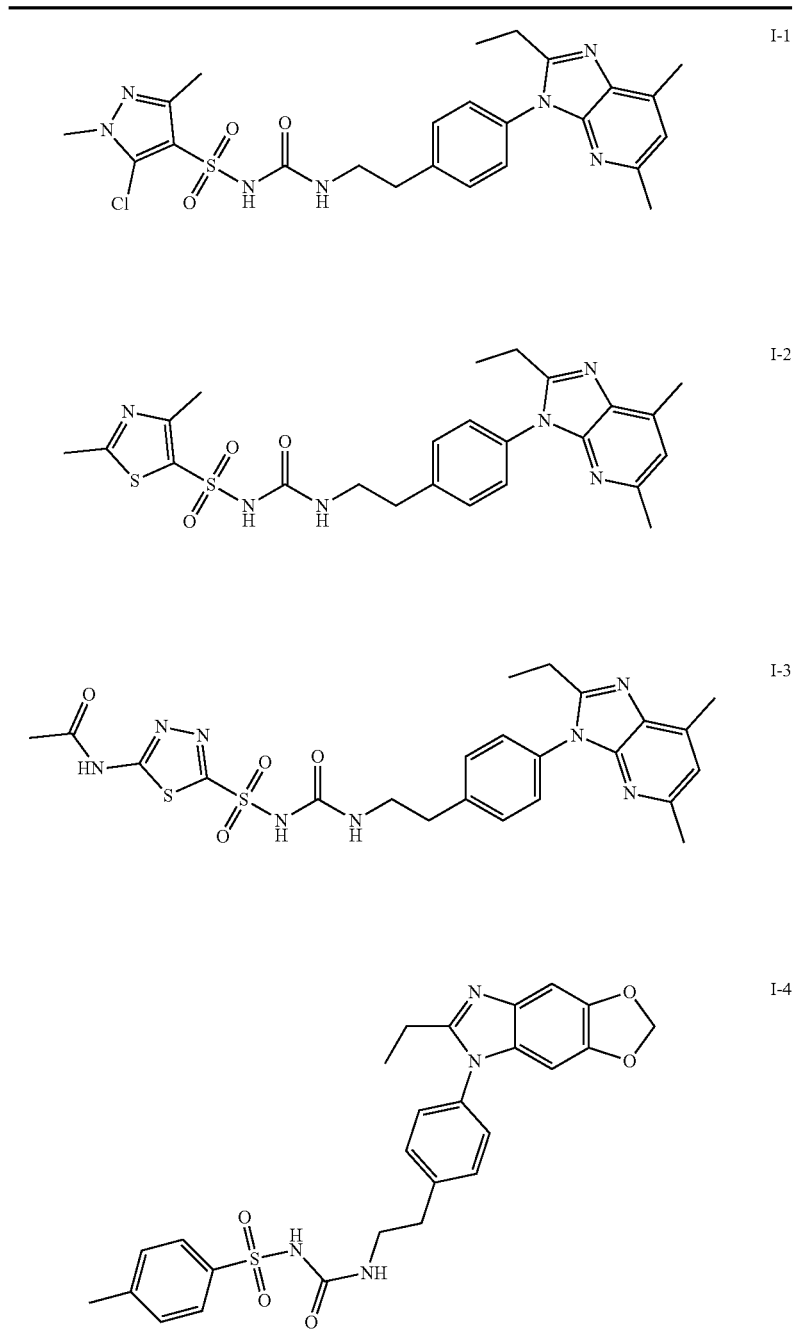

TABLE 1-continued
| | |
|---|---|
| 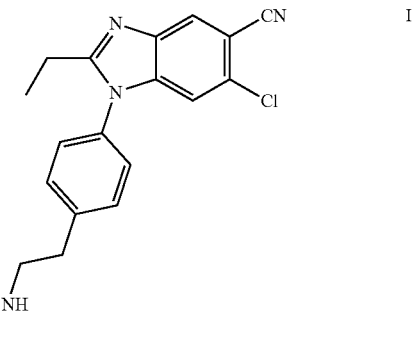 | I-5 |
| 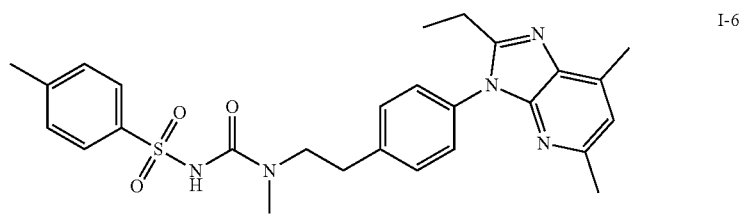 | I-6 |
| 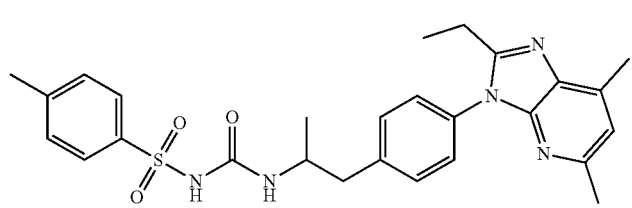 | I-7 |
| 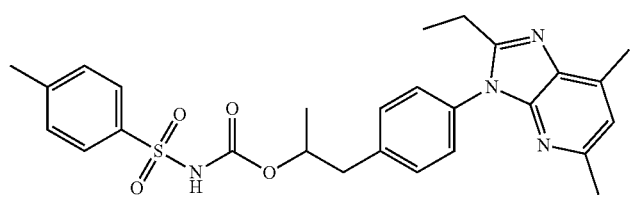 | I-8 |
| 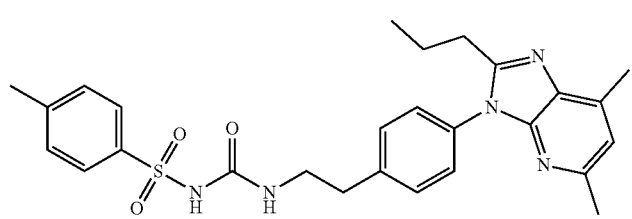 | I-9 |
| 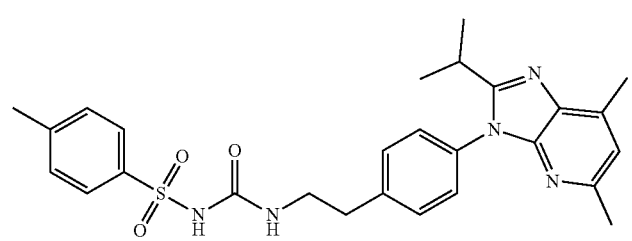 | I-10 |
| 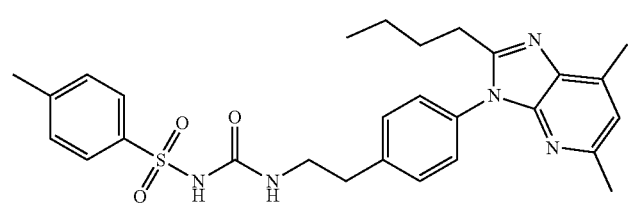 | I-11 |

TABLE 1-continued
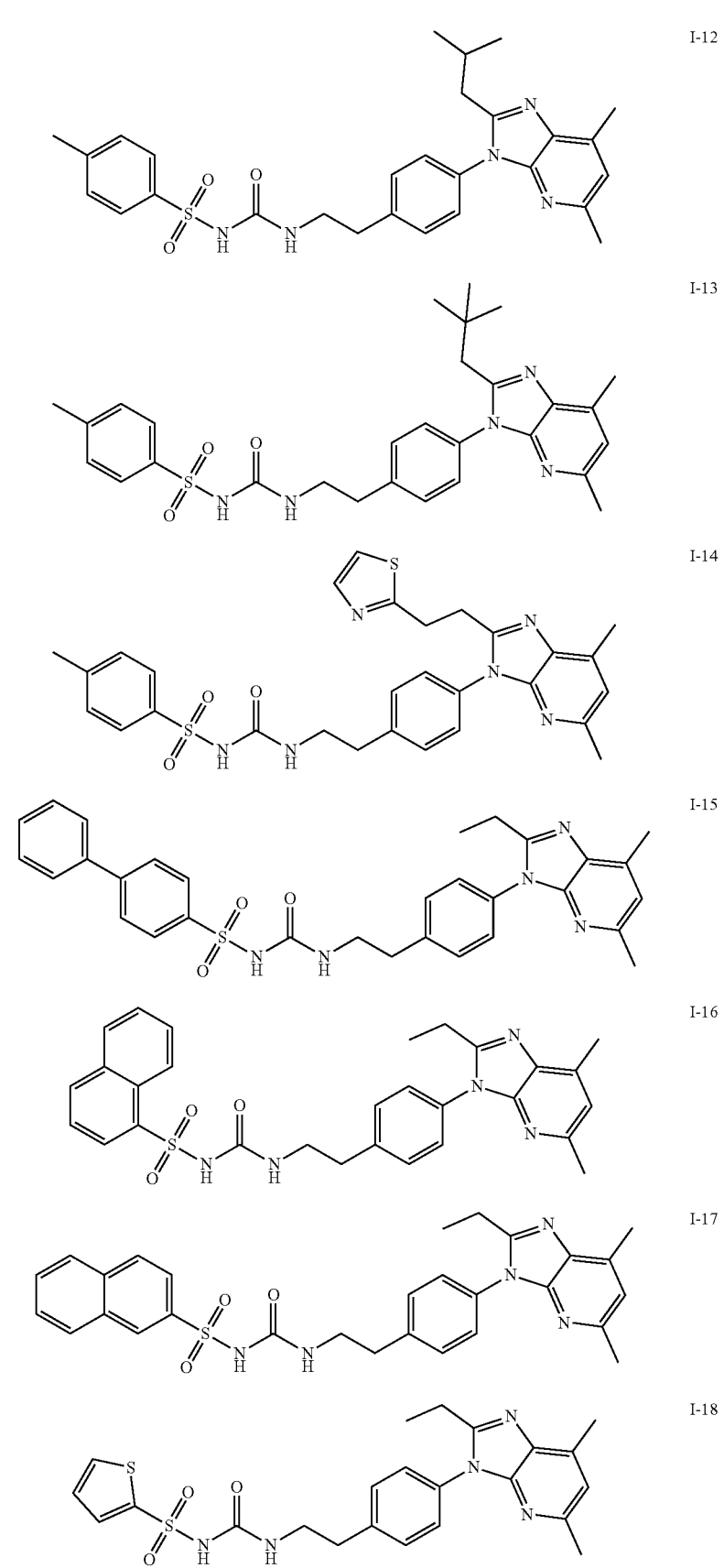

TABLE 1-continued
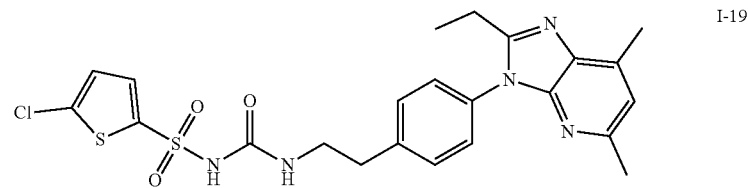
I-19
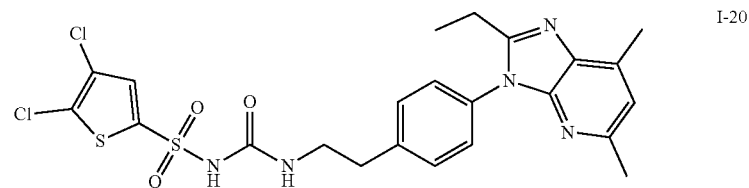
I-20
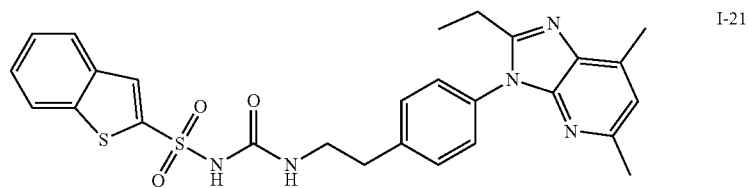
I-21
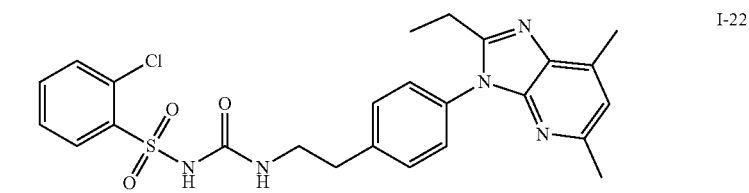
I-22
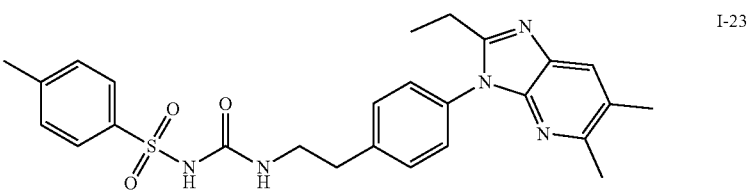
I-23
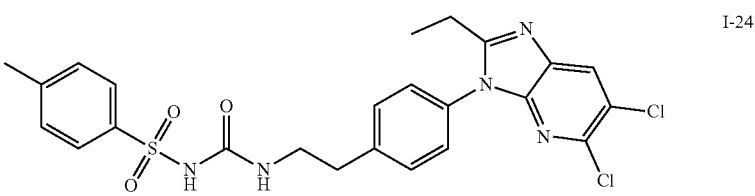
I-24
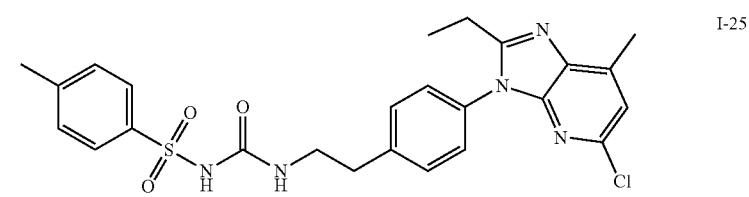
I-25
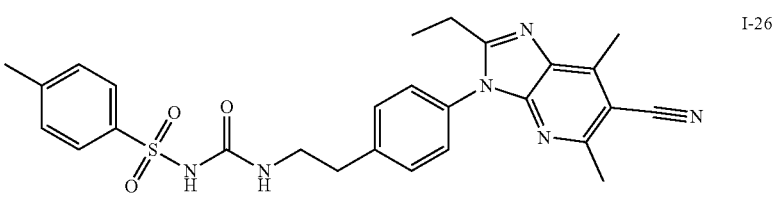
I-26

TABLE 1-continued
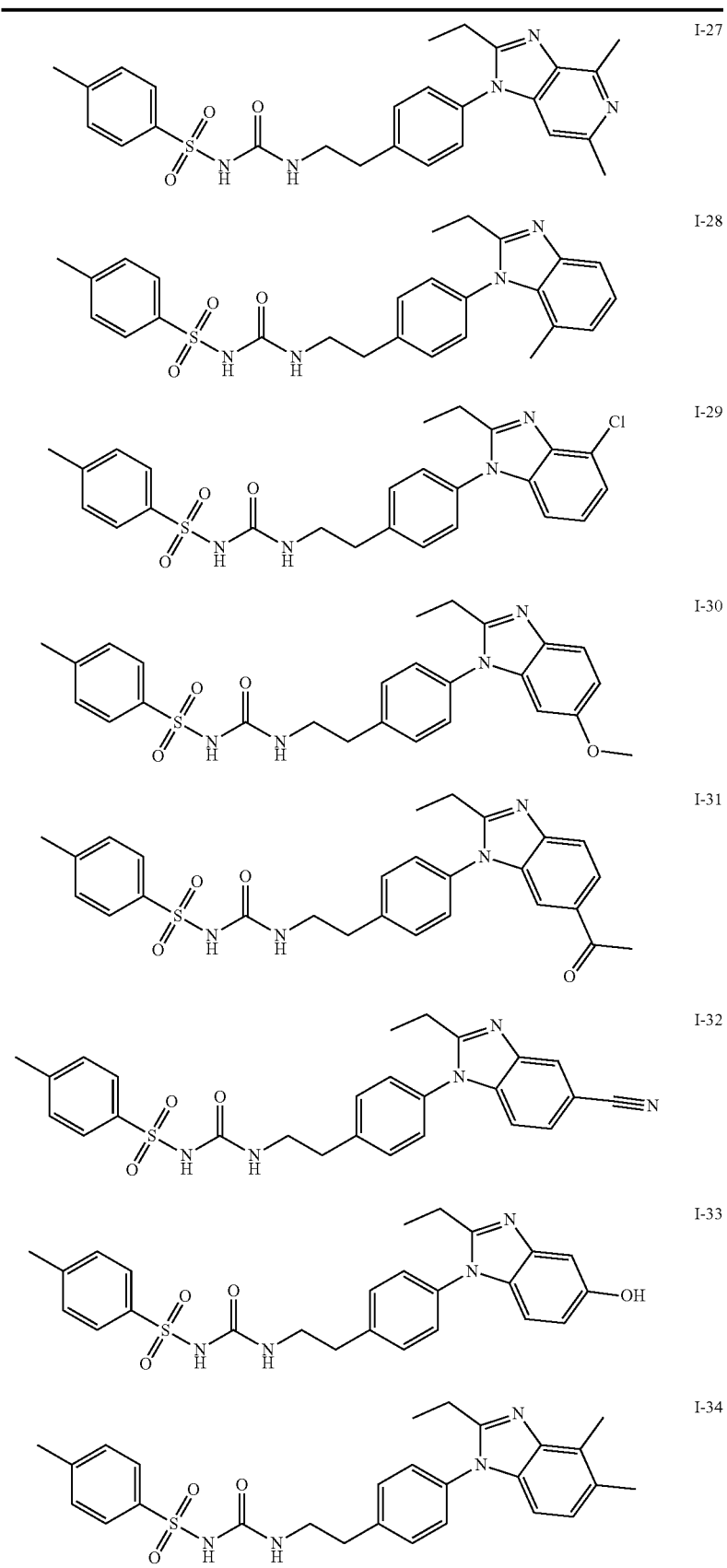

TABLE 1-continued
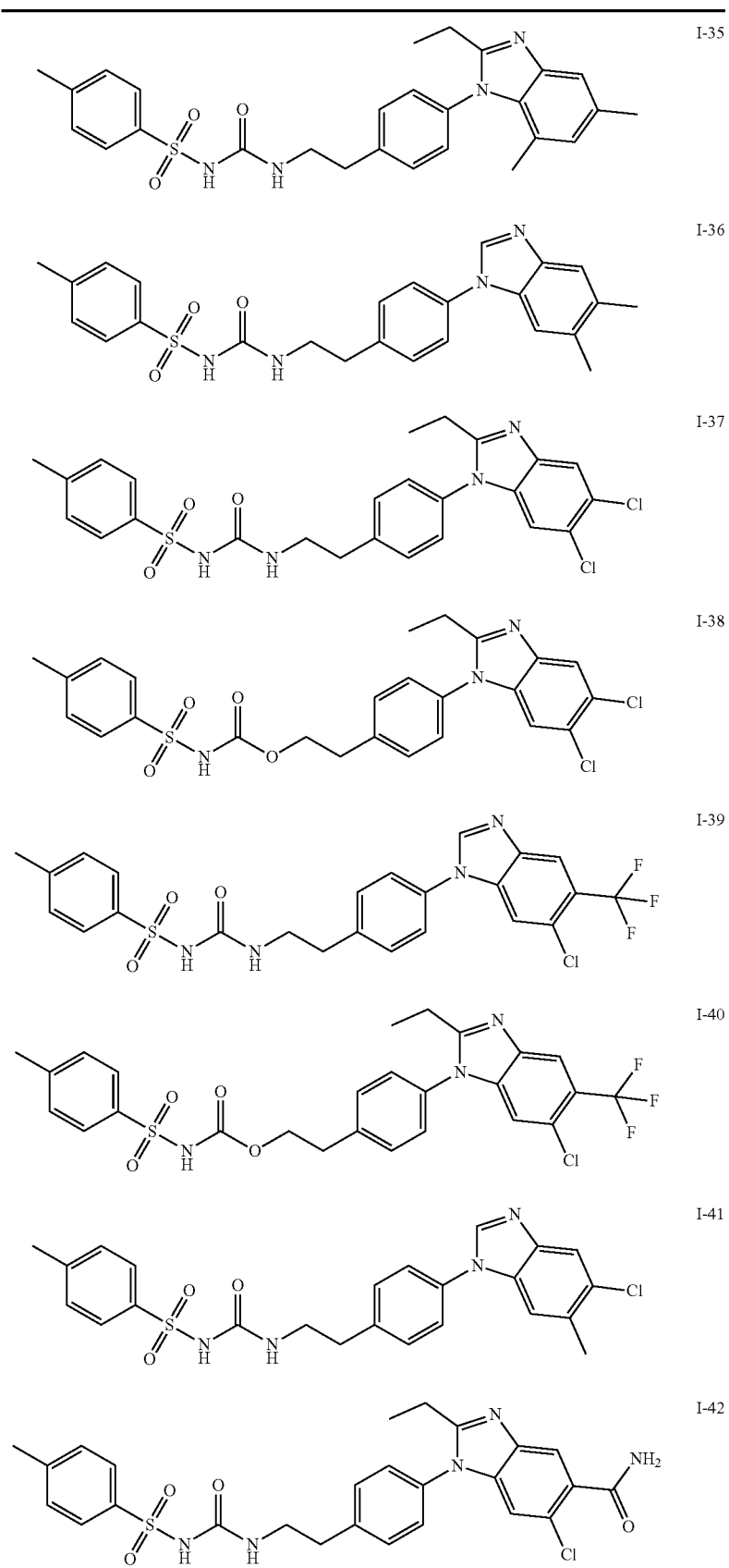

TABLE 1-continued
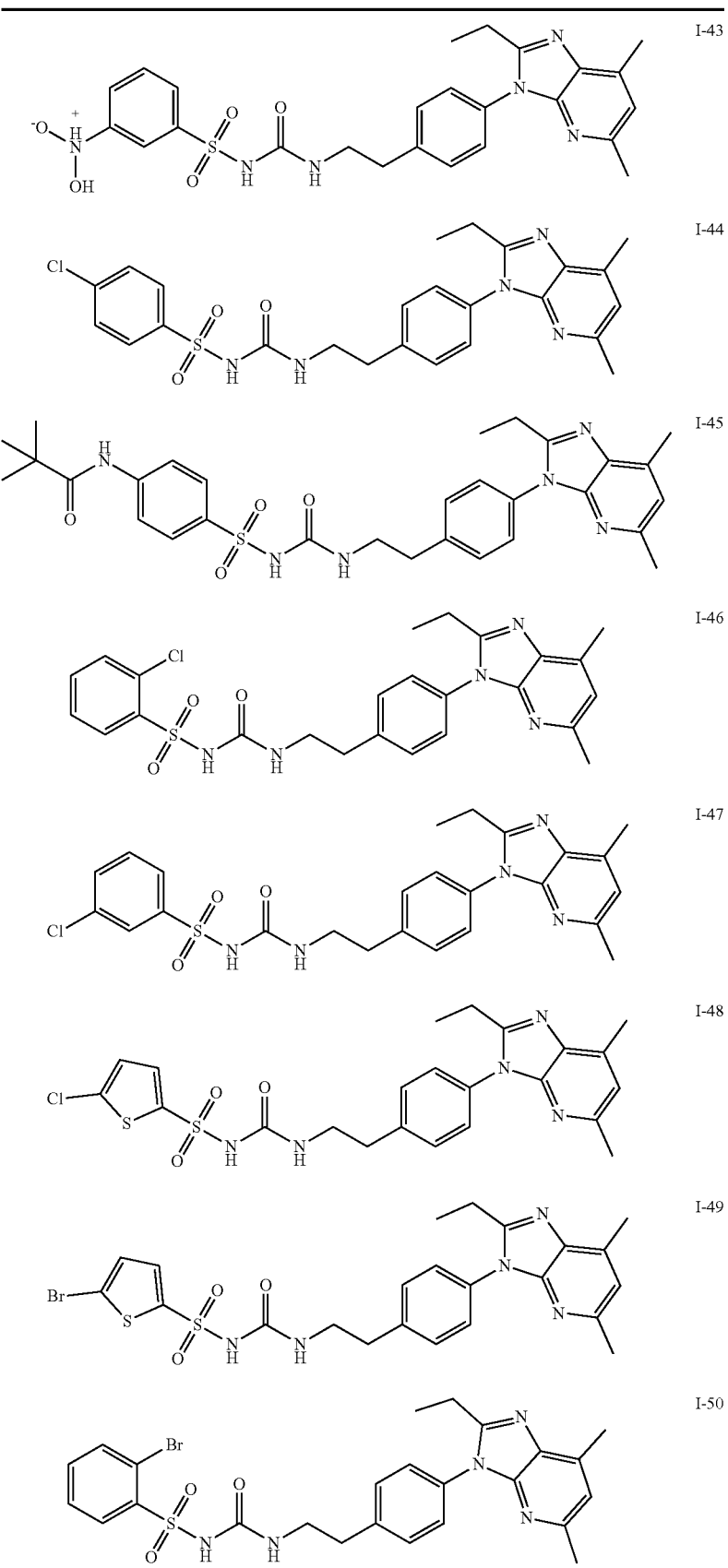

TABLE 1-continued
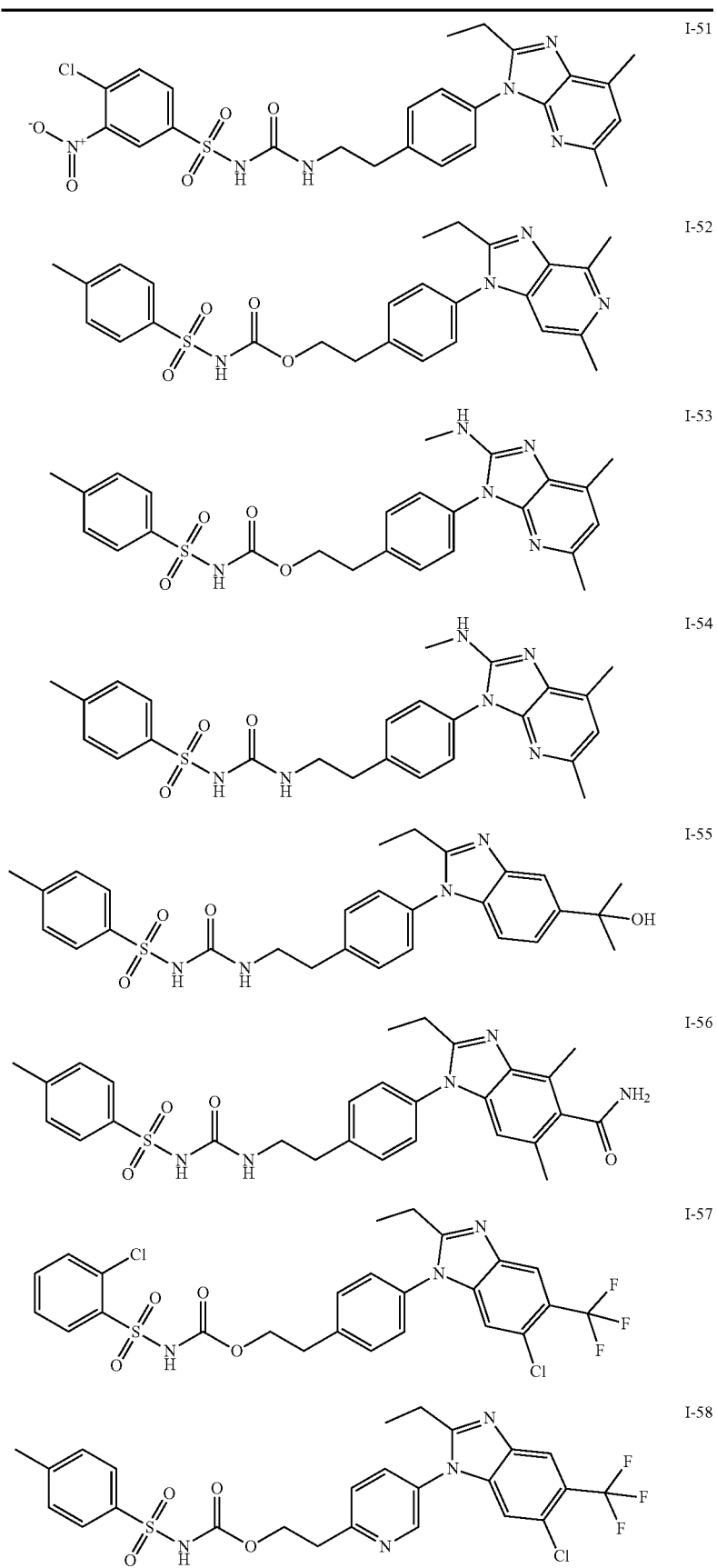

TABLE 1-continued
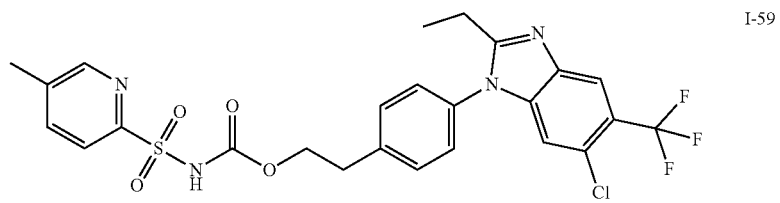
I-59
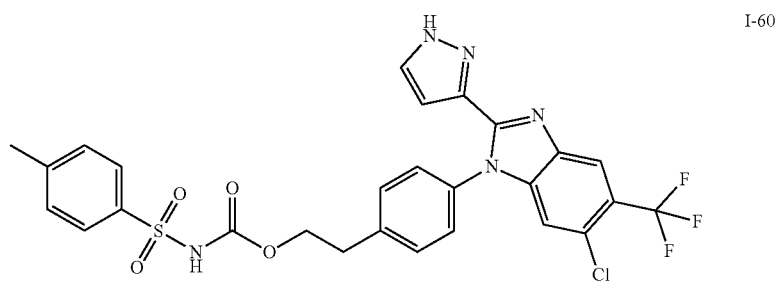
I-60
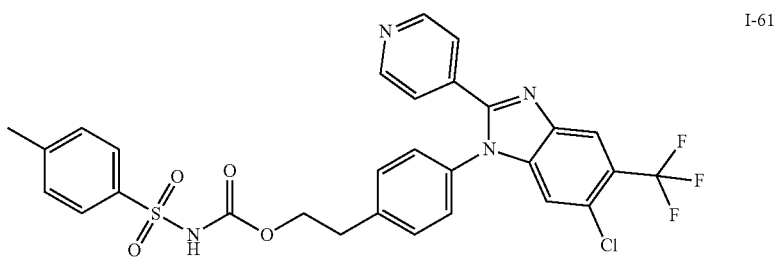
I-61
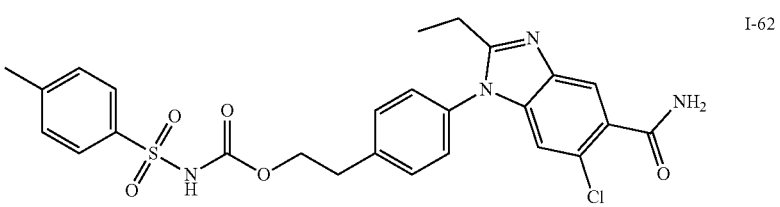
I-62
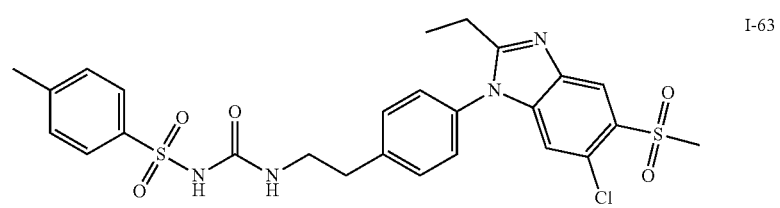
I-63
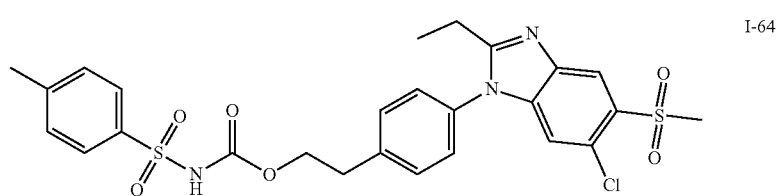
I-64
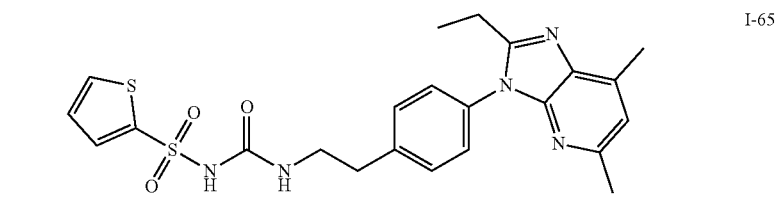
I-65

TABLE 1-continued
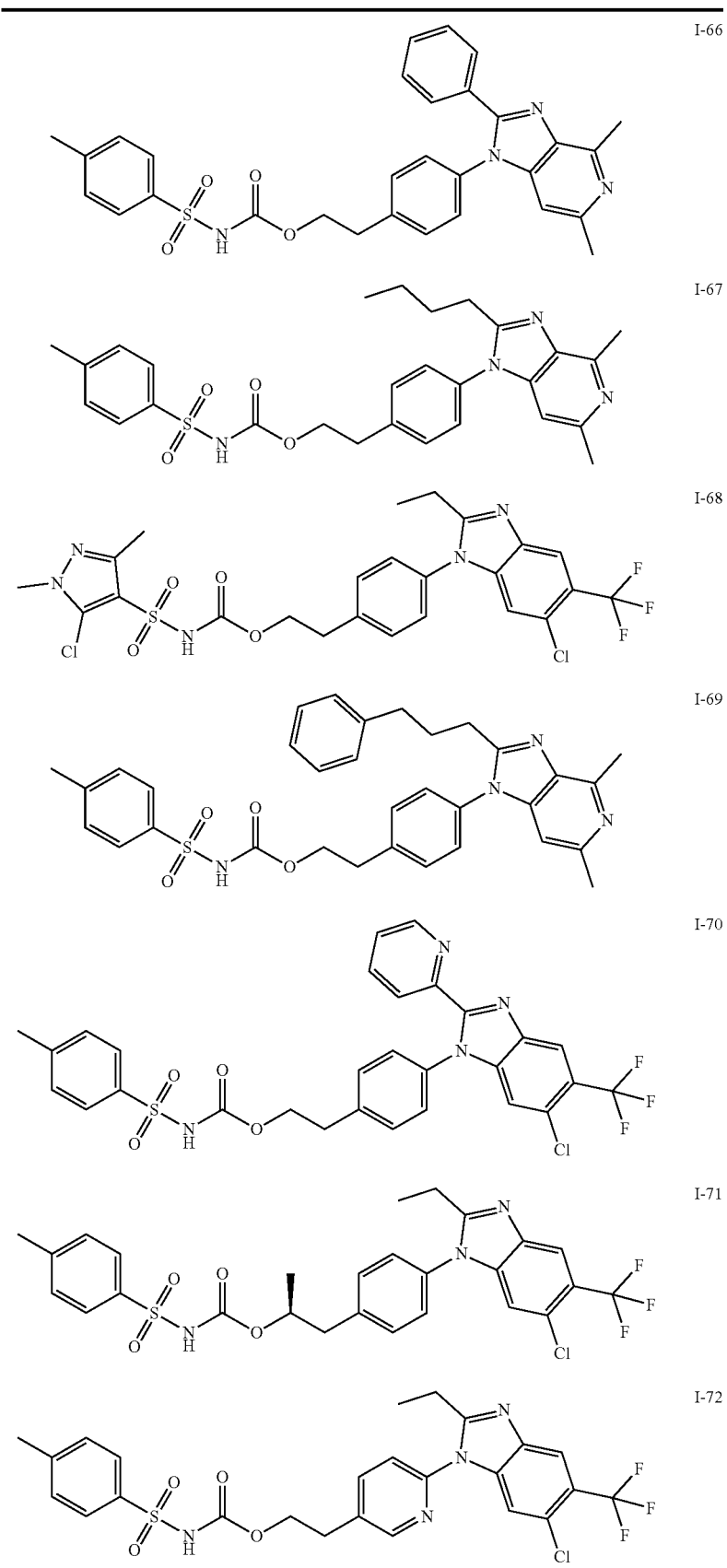

TABLE 1-continued
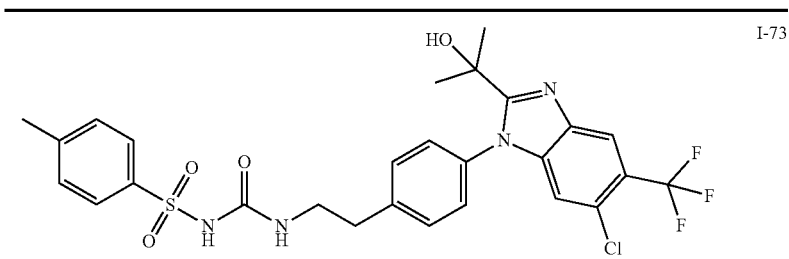
I-73
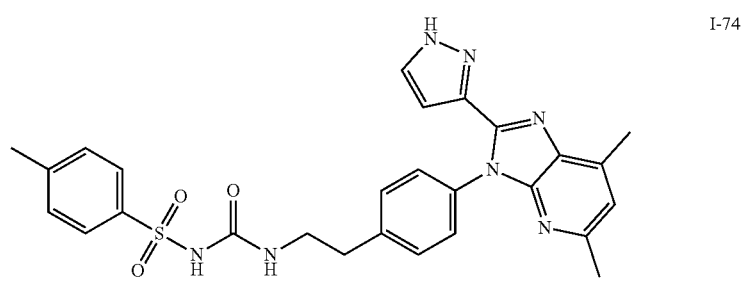
I-74
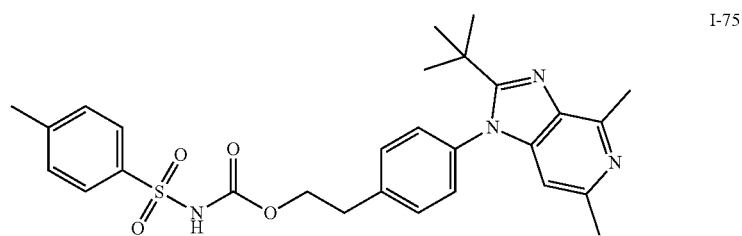
I-75
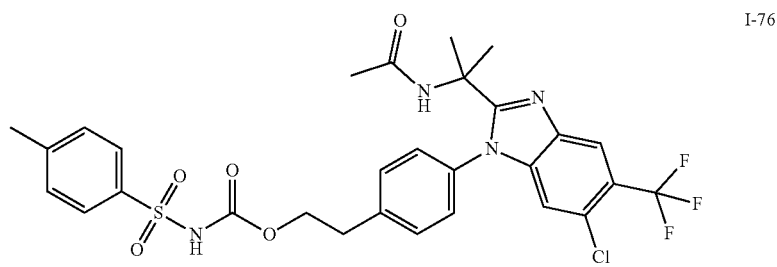
I-76
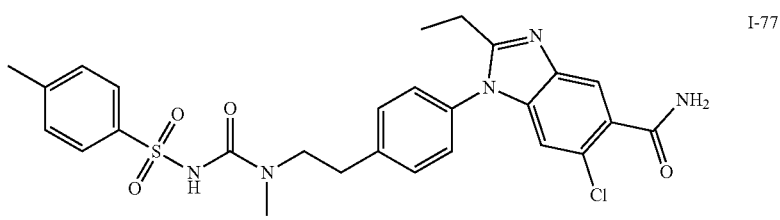
I-77

In some embodiments, a compound of formula I is a compound selected from the group consisting of I-4, I-5, I-8, I-14, I-18, I-22 to I-24, I-27, I-30 to I-34, I-40, I-42, and I-52 to I-77, or a pharmaceutically acceptable salt thereof.

In some embodiments, an agent that inhibits EP4 activity is compound A:

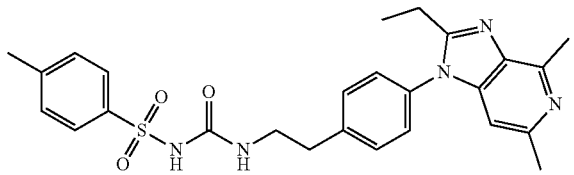

(also know as grapiprant), or a pharmaceutically acceptable salt thereof. In some embodiment, compound A is in crystal form. In some embodiments, compound A is in polymorph Form A, as described in U.S. Pat. Nos. 7,960,407 and 9,265,756, the contents of which are incorporated herein by reference in their entireties. In some embodiments, polymorph Form A of compound A is characterised by a powder X-ray diffraction pattern obtained by irradiation with Cu Kα radiation which includes main peaks at 2-Theta° 9.8, 13.2, 13.4, 13.7, 14.1, 17.5, 19.0, 21.6, 24.0 and 25.7+/−0.2. In some embodiments, polymorph Form A of compound A is characterised by differential scanning calorimetry (DSC) in which it exhibits an endothermic event at about 160° C. In some embodiments, polymorph Form A of compound A exhibits an X-ray powder diffraction pattern having characteristic peaks expressed in degrees 2-theta at about 9.9, about 13.5, about 14.3, about 16.1, about 17.7, about 21.8, about 24.14, and about 25.8. In some embodiments, polymorph Form A of compound A exhibits a differential scanning calorimetry profile having showed an endotherm/exotherm at about 155-170° C. In some embodiments, polymorph Form A of compound A exhibits a thermogravimetric analysis showing a loss of mass of 0.5-0.6% when heated from about 30° to about 150° C.

In some embodiments, an agent that inhibits EP4 activity is a compound of formula I, or a pharmaceutically acceptable salt thereof, wherein:

one of $Y^1$, $Y^2$, $Y^3$ and $Y^4$ is N and the others are independently selected from CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphryl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$ alkyl-N($R^3$)— or $C_{1-4}$ alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3$N($R^4$)C(=O)—, $C_{1-4}$ alkylsulfonylamino, $C_{3-7}$cycloalkyl, $R^3$C(=O)N($R^4$)— or $NH_2$(HN=)C—;

A is a 5-6 membered monocyclic aromatic ring optionally containing up to 3 heteroatoms selected from O, N and S, wherein said 5-6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3$N($R^4$)C(=O)—, HO(O=)C—, $C_{1-4}$ alkyl-O(O=)C—, $C_{1-4}$ alkylsulfonylamino, $C_{3-7}$cycloalkyl, $R^3$C(=O)N($R^4$)— and $NH_2$(HN=)C—; B is halo-substituted $C_{1-6}$ alkylene, $C_{3-7}$ cycloalkylene, $C_{2-6}$ alkenylene, $C_{2-6}$alkynylene, —O—$C_{1-5}$ alkylene; $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;

$R^2$ is H, $C_{1-4}$ alkyl, OH or $C_{1-4}$ alkoxy;

Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$alkylC(=O)—, $R^3$C(=O)N($R^4$)—, HO(O=)C—, $C_{1-4}$ alkyl-O(O=)C—, $C_{1-4}$alkylsulfonylamino, $C_{3-7}$ cycloalkyl, $NH_2$(HN=)C—, $Q^2$-S(O)m-, $Q^2$-O, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$alkoxy-$C_{1-4}$ alkyl, $C_{1-4}$ alkylsulfonyl, aminosulfonyl, $C_{1-4}$alkylC(=O)—, HO(O=)C—, $C_{1-4}$ alkyl-O(O=)C—, $C_{1-4}$ alkylsulfonylamino, $C_{3-7}$cycloalkyl, $R^3$C(=O)N($R^4$)—, $NH_2$(HN=)C—, $R^3$N($R^4$)C(=O)—, $R^3$N($R^4$)S(O)m-, $Q^2$-, $Q^2$-C(=O)—, $Q^2$-O—, $Q^2$-$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O)C— or $C_{1-4}$ alkyl-O—(O=)C—; and $Q^2$ is a 5-12 membered monocyclic or bicyclic aromatic ring, or a 5-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{2-4}$ alkenyl, $C_{2-4}$alkynyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2$(HN=)C—.

In some embodiments, an agent that inhibits EP4 activity is a compound of formula I, or a pharmaceutically acceptable salt thereof, wherein:

one of $Y^1$, $Y^2$, $Y^3$, and $Y^4$ is N and the others are independently selected from CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphryl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(=O)—N($R^3$)—, or $C_{1-4}$alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$alkylsulfonyl, aminosulfonyl, $C_{1-4}$ alkylC(=O)—, HO(O=)C—, $C_{1-4}$ alkyl-O(O)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—;

A is a 5-6 membered monocyclic aromatic ring optionally containing up to 2 heteroatoms selected from O, N, and S, wherein said 5-6 membered monocyclic aromatic ring is optionally substituted with up to 2 substituents selected from halo, $C_{1-4}$ alkyl, halo-substituted $C_{1-4}$ alkyl, hydroxy, $C_{1-4}$alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5-12 membered monocyclic or bicyclic aromatic ring optionally containing up to 3 heteroatoms selected from, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$alkylsulfonylamino, $C_{1-4}$ alkyl-C(=O)NH—, $Q^2$-S(O)m-, $Q^2$-O—, $Q^2$-N($R^3$)— or $Q^2$;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(=O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5-12 membered monocyclic or bicyclic aromatic ring, or a 8-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{2-4}$ alkenyl, $C_{2-4}$ alkynyl, hydroxy, $C_{1-4}$ alkoxy, halo-substituted $C_{1-4}$ alkoxy, $C_{1-4}$alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

In some embodiments, an agent that inhibits EP4 activity is a compound of formula I, or a pharmaceutically acceptable salt thereof, wherein:

one of $Y^1$, $Y^2$, $Y^3$, and $Y^4$ is N and the other are independently selected from CH and C(L);

$R^1$ is H, $C_{1-8}$alkyl, $C_{2-8}$alkenyl, $C_{2-8}$alkynyl, $C_{3-7}$cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S—, $Q^1$-$C_{1-4}$ alkyl-O—, or $C_{1-4}$ alkyl-C(O)—N($R^3$)—;

$Q^1$ is a 5-12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

A is 5-6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5-12 membered monocyclic or bicyclic aromatic ring optionally containing up to 3 heteroatoms selected from, N and S, wherein said 5-12 membered monocyclic or bicyclic aromatic ring is optionally substituted with halo, $C_{1-4}$ alkyl, halo-substituted $C_{1-4}$ alkyl, $C_{2-4}$ alkenyl, $C_{1-4}$ alkoxy, nitro, amino, cyano, $R^3$C(O)N($R^4$)—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(=O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8-12 membered tricyclic ring containing up to 3 heteroatoms selected from N and S, wherein said 5 or 6 membered monocyclic aromatic ring is optionally substituted with halo.

In some embodiments, an agent that inhibits EP4 activity is a compound of formula I, or a pharmaceutically acceptable salt thereof, wherein:

one of $Y^1$, $Y^2$, $Y^3$ and $Y^4$ is N and the others are independently selected from CH and C(L);

$R^1$ is H, $C_{1-8}$alkyl, $C_{2-8}$alkenyl, $C_{2-8}$alkynyl or $C_{3-7}$cycloalkyl, wherein said $C_{1-8}$alkyl is optionally substituted with halo, $C_{1-3}$ alkyl, hydroxy, oxo, $C_{1-4}$alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$ alkyl-C(O)—N($R^3$)—;

$Q^1$ is a 5 or 6 membered monocyclic aromatic ring optionally containing up to 4 heteroatoms selected from N and S;

A is 5-6 membered monocyclic aromatic ring system optionally substituted with halo or $C_{1-4}$ alkyl;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{2-4}$ alkenyl, $C_{1-4}$ alkoxy, nitro, amino, cyano, $R^3C(=O)N(R^4)$—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O), HO(O=)C—, $C_{1-4}$ alkyl-O(O=)C—, $C_{1-4}$alkylsulfonylamino, $C_{3-7}$ cycloalkyl, $R^3C(=O)NR^4$—, $R^3N(R^4)C(=O)$—, $R^3N(R^4)S(O)$m-, $Q^2$-, $Q^2$-C(=O)—, $Q^2$-O—, $Q^2$-$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl, and $Q^2$ is 5 or 6 membered monocyclic aromatic ring or a 8-12 membered tricyclic ring optionally containing 1 sulfur atom wherein said 5 or 6 membered monocyclic aromatic ring is optionally substituted with halo.

In some embodiments, an agent that inhibits EP4 activity is a compound of formula I, or a pharmaceutically acceptable salt thereof, wherein:

one of $Y^1$, $Y^2$, $Y^3$ and $Y^4$ is N and the others are independently selected from CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C^{1-4}$ alkyl-C(O)—N(H)—;

$Q^1$ is 5-12 membered monocyclic aromatic ring system optionally containing up to 2 heteroatoms selected from N and S, A is 5-6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is 5-12 membered monocyclic or bicyclic aromatic ring optionally containing up to 3 heteroatoms selected from N and S, wherein said 5-12 membered monocyclic aromatic ring is optionally substituted with halo, $C_{1-4}$ alkyl, nitro, $R^3C(=O)N(R^4)$— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)$m-, $Q^2$-, $Q^2C(=O)$—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system.

In some embodiments, an agent that inhibits EP4 activity is a compound of formula I, or a pharmaceutically acceptable salt thereof, wherein:

one of $Y^1$, $Y^2$, $Y^3$ and $Y^4$ is N and the others are independently selected from CH and C-L;

$R^1$ is $C_{1-5}$ alkyl optionally substituted with $C_{1-3}$alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$ alkyl-C(O)—N($R^3$)—;

A is phenyl;

B is $C_{1-2}$ alkylene optionally substituted with methyl;

W is NH, N—$CH_3$ or O;

$R^2$ is H;

Z is 5-10 membered monocyclic or bicyclic aromatic ring optionally containing up to 3 heteroatoms selected from N and S, wherein said 5-10 membered monocyclic aromatic ring is optionally substituted with chloro, bromo, methyl, nitro, $CH_3C(=O)NH$—, tBuC(=O)NH— or phenyl; and L is chloro, methyl, trifluoromethyl, hydroxy, methoxy, cyano, acetyl, —C(=O)$NH_2$, trifuluoramethyloxy, methanesulfonyl, or 1-hydroxy-1-methyl-ethyl, or two adjacent L groups are joined together to form a methylenedioxy group.

In some embodiments, an agent that inhibits EP4 activity is a compound of formula I, or a pharmaceutically acceptable salt thereof, wherein:

one of $Y^1$, $Y^2$, $Y^3$ and $Y^4$ is N and the others are independently selected from CH and C-(L);

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—$CH_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)$NH_2$, trifuluoromethyloxy, methanesulfonyl, or 1-hydroxy-1-methyl-ethyl, or two adjacent L groups are joined together to form a methylenedioxy group.

In some embodiments, an agent that inhibits EP4 activity is a compound of formula I, or a pharmaceutically acceptable salt thereof, wherein $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
n) $Y^1$ and $Y^2$ are C(L), $Y^3$ is CH and $Y^4$ is N;
p) $Y^1$ and $Y^2$ are C(L), $Y^3$ is N and $Y^4$ is CH;
r) $Y^1$ is C(L), $Y^2$ and $Y^3$ are CH, and $Y^4$ is N; and
s) $Y^2$ is C(L), $Y^1$ and $Y^3$ are CH, and $Y^4$ is N;

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—$CH_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

In some embodiments, an agent that inhibits EP4 activity is a compound of formula I, or a pharmaceutically acceptable salt thereof, wherein $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CHY$^2$ and $Y^3$ are C(L) and $Y^4$ is N;
c) $Y^1$, $Y^2$ and $Y^3$ are C(L) and $Y^4$ is N; and
d) $Y^1$ and $Y^3$ are C(L), $Y^2$ is N and $Y^4$ is CH; $R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;
B is ethylene or propylene;
W is NH, N—CH$_3$ or O;
$R^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

In some embodiments, an agent that inhibits EP4 activity is a compound of formula II:

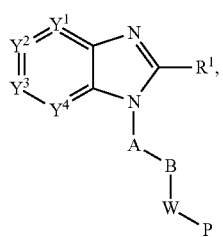

(II)

or a pharmaceutically acceptable salt thereof, wherein
$Y^1$, $Y^2$, $Y^3$ and $Y^4$ are independently selected from N, CH or C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, amino, mono- or di-($C_{1-8}$ alkyl)amino, $C_{1-4}$alkyl-C(=O)—N(R$^3$)— or $C_{1-4}$alkyl-S(O)m-N(R$^3$)—, wherein said $C_{1-8}$ alkyl, $C_{2-8}$ alkenyl and $C_{2-8}$ alkynyl are optionally substituted with halo, $C_{1-3}$ alkyl, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N(R$^3$)—, $Q^1$-$C_{1-4}$alkyl-N(R$^3$)— or $C_{1-4}$alkyl-C(O)—N(R$^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3N(R^4)C(=O)$—, $C_{1-4}$ alkylsulfonylamino, $C_{3-7}$ cycloalkyl, $R^3C(=O)N(R^4)$— or NH$_2$(HN=)C—;

A is a benzene ring optionally substituted with up to 3 substituents or pyridine ring optionally substituted with up to 3 substituents, wherein said substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C(=O)$—, HO(O=)C—, $C_{1-4}$alkyl-O(O=)C—, $C_{1-4}$ alkylsulfonylamino, $C_{3-7}$ cycloalkyl, $R^3C(=O)N(R^4)$— and NH$_2$(HN=)C—;

B is $C_{2-6}$ alkylene, $C_{3-7}$ cycloalkylene, $C_{2-6}$ alkenylene, or $C_{2-6}$ alkynylene optionally substituted with $C_{1-3}$ alkyl;

W is NH or O;
P is H, a protecting group, or $Q^3$-OC(=O)—;
$Q^3$ is a 6-10 membered monocyclic or bicyclic aromatic ring optionally substituted with halo, $C_{1-4}$ alkyl, $C_{1-4}$ alkoxy, $C_{1-4}$ alkylthio, nitro, cyano, $C_{1-4}$ alkylsulfonyl, $C_{1-4}$alkylC(=O)—, HO(O=)C—, or $C_{1-4}$alkyl-O(O=)C—;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $C_{1-4}$ alkyl sulfonylamino, $C_{3-7}$ cycloalkyl, $R^3C(=O)N(R^4)$—, NH$_2$(HN=)C—, $R^3N(R^4)C(=O)$— or $R^3N(R^4)S(O)$m-, or two adjacent L groups are optionally joined together to form an alkylene chain having 3 or 4 members in which one or two (non-adjacent) carbon atoms are optionally replaced by oxygen atoms;

m is 0, 1 or 2; and
$R^3$ and $R^4$ are independently selected from H and $C_{1-4}$ alkyl.

In some embodiments, P is H.

In some embodiments, P is a protecting group. Exemplary protecting groups are described in detail in Greene (2006), the content of which is incorporated herein by reference in its entirety.

In some embodiments, P is a suitable amino protecting group. Suitable amino protecting groups are well known in the art and include those described in detail in Greene (2006). In some embodiments, suitable amino protecting groups, taken with the —NH-moiety to which they are attached, include, but are not limited to, aralkylamines, carbamates, allyl amines, amides, and the like. In certain embodiments, P is an amino protecting group selected from t-butyloxycarbonyl (BOC), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, or pivaloyl. In some embodiments, P is an amino protecting group selected from t-butyloxycarbonyl, ethyloxycarbonyl, pivaloyl, and acetyl. In some embodiments, P is pivaloyl.

In some embodiments, P is a suitable hydroxyl protecting group. Suitable hydroxyl protecting groups are well known in the art and include those described in detail in Greene (2006). In certain embodiments, a suitable hydroxyl protecting group, taken with the oxygen atom to which it is bound, is selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl. In certain embodiments, a suitable hydroxyl protecting group, taken with the oxygen atom to which it is bound, is a silyl ether or arylalkyl ether. In some embodiments, P is a suitable hydroxyl protecting group selected from t-butyldimethylsilyl and benzoyl. In some embodiments, P is t-butyldimethylsilyl ("TBS").

In some embodiments, P is $Q^3$-OC(=O)—, wherein $Q^3$ is as defined in the embodiments described herein.

In some embodiments, $Q^3$ is a 6 membered monocyclic aromatic ring optionally substituted with halo, $C_{1-4}$ alkyl, $C_{1-4}$ alkoxy, $C_{1-4}$ alkylthio, nitro, cyano, $C_{1-4}$ alkylsulfonyl, $C_{1-4}$alkylC(=O)—, HO(O=)C—, or $C_{1-4}$alkyl-O(O=)C—.

In some embodiments, $Q^3$ is a 8-10 membered bicyclic aromatic ring optionally substituted with halo, $C_{1-4}$ alkyl, $C_{1-4}$ alkoxy, $C_{1-4}$ alkylthio, nitro, cyano, $C_{1-4}$ alkylsulfonyl, $C_{1-4}$alkylC(=O)—, HO(O=)C—, or $C_{1-4}$alkyl-O(O=)C—.

In some embodiments, an agent that inhibits EP4 activity is a compound of formula III,

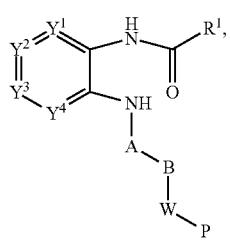

(III)

or a pharmaceutically acceptable salt thereof, wherein
$Y^1$, $Y^2$, $Y^3$ and $Y^4$ are independently selected from N, CH or C(L);
$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—;
$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or NH$_2$(HN=)C—; A is a benzene ring optionally substituted with up to 3 substituents or pyridine ring optionally substituted with up to 3 substituents, wherein said substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3$N($R^4$)C(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)— and NH$_2$(HN=)C—;

B is $C_{2-6}$ alkylene, $C_{3-7}$ cycloalkylene, $C_{2-6}$ alkenylene, or $C_{2-6}$ alkynylene optionally substituted with $C_{1-3}$ alkyl;

W is NH or O;

P is H, a protecting group, or Z—S(O)$_2$—N($R^2$)—C(=O)—;

Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, $R^3$C(=O)N($R^4$)—, HO(O=)C—, $C_{1-4}$alkyl-O(O=)C—, $C_{1-4}$ alkylsulfonylamino, $C_{3-7}$ cycloalkyl, NH$_2$(HN=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $C_{1-4}$ alkyl sulfonylamino, $C_{3-7}$ cycloalkyl, $R^3$C(=O)N($R^4$)—, NH$_2$(HN=)C—, $R^3$N($R^4$)C(=O)— or $R^3$N($R^4$)S(O)m-, or two adjacent L groups are optionally joined together to form an alkylene chain having 3 or 4 members in which one or two (non-adjacent) carbon atoms are optionally replaced by oxygen atoms;

m is 0, 1 or 2; and $R^2$, $R^3$, and $R^4$ are independently selected from H and $C_{1-4}$ alkyl.

In some embodiments, P is H.

In some embodiments, P is a protecting group.

In some embodiments, P is Z—S(O)$_2$—N($R^2$)—C(=O)—, wherein Z is as defined in the embodiments described herein.

2.3. Compounds of Formulae I', II', and III'

In some embodiments, an agent that inhibits EP4 activity is a compound of formula (I'):

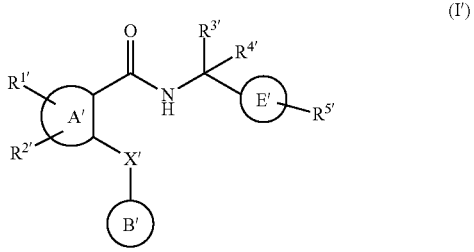

(I')

or a pharmaceutically acceptable salt thereof, wherein:
A' represents a phenyl group or a pyridyl group;
B' represents an aryl group or a heteroaryl group;
E' represents a 1,4-phenylene group;
$R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
$R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 2 to 6 carbon atoms;
$R^{5'}$ represents
$CO_2H$, $—CO_2W'$,

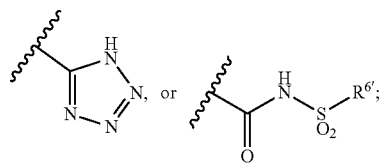

$R^{6'}$ represents an alkyl group having from 1 to 6 carbon atoms, a cycloalkyl group having from 3 to 7 ring atoms, an aryl group or a heteroaryl group;
X' represents a methylene group, an oxygen atom or a sulfur atom;
said aryl groups have from 6 to 10 carbon atoms;
said heteroaryl groups are 5- to 10-membered aromatic heterocyclic groups containing from 1 to 3 heteroatoms selected from the group consisting of sulfur atoms, oxygen atoms and nitrogen atoms;
said aryl groups and said heteroaryl groups referred to in the definitions of B' are unsubstituted or are substituted by at least one substituent selected from the group consisting of substituents α;
said 1,4-phenylene group referred to in the definition of E' is unsubstituted or is substituted by at least one substituent selected from the group consisting of substituents β;
said aryl groups and said heteroaryl groups referred to in the definitions of $R^{6'}$ and α are unsubstituted or are substituted by at least one substituent selected from the group consisting of substituents β;
said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;
said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;
W' is a pharmaceutically acceptable ester pro-drug group;
with the proviso $R^{1'}$ and $R^{2'}$ do not represent a hydrogen atom simultaneously.

As defined generally above, A' represents a phenyl group or a pyridyl group.
In some embodiments, A' is phenyl. In some embodiments, A' is pyridyl.
In some embodiments, A' is selected from those as depicted in Table 2.
As defined generally above, B' represents an aryl group or a heteroaryl group.
In some embodiments, B' is aryl.
In some embodiments, B' is heteroaryl.
In some embodiments, B' represents a phenyl or pyridyl group, said group is unsubstituted or is substituted by at least one substituent selected from the group consisting of substituents α, wherein each substituent α is as defined in the embodiments described herein.
In some embodiments, B' represents a phenyl group optionally substituted by substituent selected from the group consisting of substituents α, wherein each substituent α is as defined in the embodiments described herein.
In some embodiments, B' is selected from those as depicted in Table 2.
As defined generally above, $R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group.

In some embodiments, $R^{1'}$ represents a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group.

In some embodiments, $R^{1'}$ is a hydrogen atom. In some embodiments, $R^{1'}$ is a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group.

In some embodiments, $R^{1'}$ is a halogen atom. In some embodiments, $R^{1'}$ is an alkyl group having from 1 to 4 carbon atoms. In some embodiments, $R^{1'}$ is an alkoxy group having from 1 to 4 carbon atoms. In some embodiments, $R^{1'}$ is a haloalkyl group having from 1 to 4 carbon atoms. In some embodiments, $R^{1'}$ is a haloalkoxy group having from 1 to 4 carbon atoms. In some embodiments, $R^{1'}$ is a cyano group. In some embodiments, $R^{1'}$ is an aminocarbonyl group.

In some embodiments, $R^{2'}$ represents a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group.

In some embodiments, $R^{2'}$ is a hydrogen atom. In some embodiments, $R^{2'}$ is a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group.

In some embodiments, $R^{2'}$ is a halogen atom. In some embodiments, $R^{2'}$ is an alkyl group having from 1 to 4 carbon atoms. In some embodiments, $R^{2'}$ is an alkoxy group having from 1 to 4 carbon atoms. In some embodiments, $R^{2'}$ is a haloalkyl group having from 1 to 4 carbon atoms. In some embodiments, $R^{2'}$ is a haloalkoxy group having from 1 to 4 carbon atoms. In some embodiments, $R^{2'}$ is a cyano group. In some embodiments, $R^{2'}$ is an aminocarbonyl group.

In some embodiments, $R^{1'}$ represents a halogen atom and $R^{2'}$ represents a hydrogen atom.

In some embodiments, each of $R^{1'}$ and $R^{2'}$ is independently selected from those as depicted in Table 2.

As defined generally above, $R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 2 to 6 carbon atoms.

In some embodiments, $R^{3'}$ represents a hydrogen atom or an alkyl group having from 1 to 4 carbon atoms.

In some embodiments, $R^{3'}$ is a hydrogen atom. In some embodiments, $R^{3'}$ is an alkyl group having from 1 to 4 carbon atoms.

In some embodiments, $R^{4'}$ represents a hydrogen atom or an alkyl group having from 1 to 4 carbon atoms.

In some embodiments, $R^{4'}$ is a hydrogen atom. In some embodiments, $R^{4'}$ is an alkyl group having from 1 to 4 carbon atoms.

In some embodiments, $R^{3'}$ and $R^{4'}$ groups may be joined together to form an alkylene chain having 2 to 6 carbon atoms.

In some embodiments, $R^{3'}$ and $R^{4'}$ independently represent a hydrogen atom or an alkyl group having from 1 to 4 carbon atoms.

In some embodiments, $R^{3'}$ represents an alkyl group having from 1 to 4 carbon atoms and $R^{4'}$ represents a hydrogen atom.

In some embodiments, $R^{3'}$ represents a methyl group and $R^{4'}$ represents a hydrogen atom.

In some embodiments, each of $R^{3'}$ and $R^{4'}$ is independently selected from those as depicted in Table 2.

As defined generally above, $R^{5'}$ represents —CO$_2$H, —CO$_2$W',

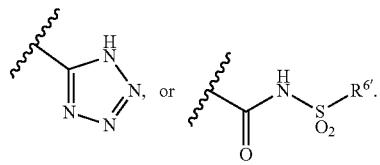

In some embodiments, $R^{5'}$ is —CO$_2$H.

In some embodiments, $R^{5'}$ is —CO$_2$W', wherein W' is as defined in the embodiments described herein.

In some embodiments, $R^{5'}$ is

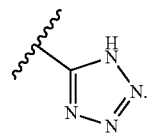

In some embodiments, $R^{5'}$ is

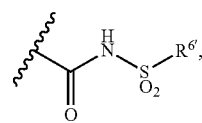

wherein $R^{6'}$ is as defined in the embodiments described herein.

In some embodiments, $R^{5'}$ represents —CO$_2$H,

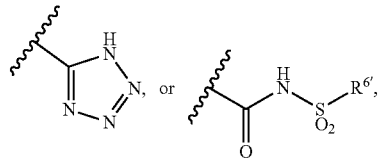

and $R^{6'}$ represents an aryl group optionally substituted by halogen atoms or a heteroaryl group.

In some embodiments, $R^{5'}$ represents —CO$_2$H,

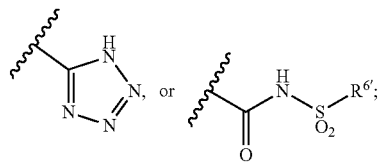

and $R^{6'}$ represents an aryl group optionally substituted by halogen atoms.

In some embodiments, $R^{5'}$ represents —CO$_2$H,

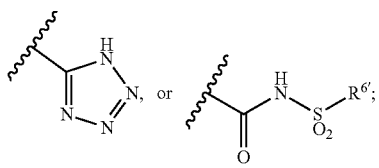

and $R^{6'}$ represents a phenyl group optionally substituted by halogen atoms.

In some embodiments, $R^{5'}$ represents —CO$_2$H or

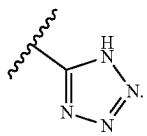

In some embodiments, $R^{5'}$ is selected from those as depicted in Table 2.

As defined generally above, $R^{6'}$ represents an alkyl group having from 1 to 6 carbon atoms, a cycloalkyl group having from 3 to 7 ring atoms, an aryl group or a heteroaryl group.

In some embodiments, $R^{6'}$ is an alkyl group having from 1 to 6 carbon atoms.

In some embodiments, $R^{6'}$ is a cycloalkyl group having from 3 to 7 ring atoms.

In some embodiments, $R^{6'}$ is an aryl group.

In some embodiments, $R^{6'}$ is a heteroaryl group.

In some embodiments, $R^{6'}$ is selected from those as depicted in Table 2.

As defined generally above, X' represents a methylene group, an oxygen atom or a sulfur atom.

In some embodiments, X' is a methylene group.

In some embodiments, X is an oxygen atom.

In some embodiments, X' is a sulfur atom.

In some embodiments, X' represents a methylene group or an oxygen atom.

In some embodiments, X' is selected from those as depicted in Table 2.

As defined generally above, said aryl groups have from 6 to 10 carbon atoms.

In some embodiments, an aryl group has 6 carbon items. In some embodiments, an aryl group has 7 carbon items. In some embodiments, an aryl group has 8 carbon items. In some embodiments, an aryl group has 9 carbon items. In some embodiments, an aryl group has 10 carbon items.

In some embodiments, an aryl group is selected from those as depicted in Table 2.

As defined generally above, said heteroaryl groups are 5- to 10-membered aromatic heterocyclic groups containing from 1 to 3 heteroatoms selected from the group consisting of sulfur atoms, oxygen atoms and nitrogen atoms.

In some embodiments, a heteroaryl group is a 5-membered aromatic heterocyclic group containing from 1 to 3 heteroatoms selected from the group consisting of sulfur atoms, oxygen atoms and nitrogen atoms.

In some embodiments, a heteroaryl group is a 6-membered aromatic heterocyclic group containing from 1 to 3 heteroatoms selected from the group consisting of sulfur atoms, oxygen atoms and nitrogen atoms.

In some embodiments, a heteroaryl group is a 7-membered aromatic heterocyclic group containing from 1 to 3 heteroatoms selected from the group consisting of sulfur atoms, oxygen atoms and nitrogen atoms.

In some embodiments, a heteroaryl group is a 8-membered aromatic heterocyclic group containing from 1 to 3 heteroatoms selected from the group consisting of sulfur atoms, oxygen atoms and nitrogen atoms.

In some embodiments, a heteroaryl group is a 9-membered aromatic heterocyclic group containing from 1 to 3 heteroatoms selected from the group consisting of sulfur atoms, oxygen atoms and nitrogen atoms.

In some embodiments, a heteroaryl group is a 10-membered aromatic heterocyclic group containing from 1 to 3 heteroatoms selected from the group consisting of sulfur atoms, oxygen atoms and nitrogen atoms.

In some embodiments, a heteroaryl group is selected from those as depicted in Table 2.

As generally defined above, said aryl groups and said heteroaryl groups referred to in the definitions of B' are unsubstituted or are substituted by at least one substituent selected from the group consisting of substituents α.

In some embodiments, an aryl group referred to in the definitions of B' is unsubstituted. In some embodiments, an aryl group referred to in the definitions of B' is substituted by at least one substituent selected from the group consisting of substituents α.

In some embodiments, a heteroaryl group referred to in the definitions of B' is unsubstituted. In some embodiments, a heteroaryl group referred to in the definitions of B' is substituted by at least one substituent selected from the group consisting of substituents α.

In some embodiments, said aryl groups and said heteroaryl groups referred to in the definitions of B' are selected from those as depicted in Table 2.

As defined generally above, said 1,4-phenylene group referred to in the definition of E' is unsubstituted or is substituted by at least one substituent selected from the group consisting of substituents β.

In some embodiments, a 1,4-phenylene group referred to in the definition of E' is unsubstituted. In some embodiments, a 1,4-phenylene group referred to in the definition of E' is substituted by at least one substituent selected from the group consisting of substituents β.

In some embodiments, a 1,4-phenylene group referred to in the definition of E' is a 1,4-phenylene group substituted by at least one substituent selected from the group consisting of halogen atoms and alkyl groups having from 1 to 4 carbon atoms.

In some embodiments, said 1,4-phenylene group referred to in the definition of E' is selected from those as depicted in Table 2.

As defined generally above, said aryl groups and said heteroaryl groups referred to in the definitions of $R^{6'}$ and α are unsubstituted or are substituted by at least one substituent selected from the group consisting of substituents β.

In some embodiments, an aryl group referred to in the definitions of $R^{6'}$ is unsubstituted. In some embodiments, an aryl group referred to in the definitions of $R^{6'}$ is substituted by at least one substituent selected from the group consisting of substituents β.

In some embodiments, an aryl group referred to in the definitions of α is unsubstituted. In some embodiments, an aryl group referred to in the definitions of α is substituted by at least one substituent selected from the group consisting of substituents β.

In some embodiments, a heteroaryl group referred to in the definitions of $R^{6'}$ is unsubstituted. In some embodiments, a heteroaryl group referred to in the definitions of $R^{6'}$ is substituted by at least one substituent selected from the group consisting of substituents β.

In some embodiments, a heteroaryl group referred to in the definitions of α is unsubstituted. In some embodiments, a heteroaryl group referred to in the definitions of α is substituted by at least one substituent selected from the group consisting of substituents β.

In some embodiments, each of said aryl groups and said heteroaryl groups referred to in the definitions of $R^{6'}$ and a is independently selected from those as depicted in Table 2.

As defined generally above, said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent a groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms.

In some embodiments, a substituent α is selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part, and alkylsulfonylamino groups having from 1 to 4 carbon atoms.

In some embodiments, a substituent α is a halogen atom.

In some embodiments, a substituent α is an alkyl group having from 1 to 4 carbon atoms.

In some embodiments, a substituent α is an alkoxy group having from 1 to 4 carbon atoms.

In some embodiments, a substituent α is a haloalkyl group having from 1 to 4 carbon atoms.

In some embodiments, a substituent α is a haloalkoxy group having from 1 to 4 carbon atoms.

In some embodiments, a substituent α is a cyano group.

In some embodiments, a substituent α is an alkynyl group having from 2 to 6 carbon atoms.

In some embodiments, a substituent α is an alkanoyl group having from 1 to 5 carbon atoms.

In some embodiments, a substituent α is a cycloalkyl group having from 3 to 7 ring atoms.

In some embodiments, a substituent α is a heteroaryl group.

In some embodiments, a substituent α is an aryl group.

In some embodiments, a substituent α is an aralkoxy group having from 7 to 10 carbon atoms.

In some embodiments, a substituent α is an arylcarbonyl group.

In some embodiments, a substituent α is an aminocarbonyl group.

In some embodiments, a substituent α is an alkenyl group having from 2 to 5 carbon atoms.

In some embodiments, a substituent α is an alkylthio group having from 1 to 4 carbon atoms.

In some embodiments, a substituent α is an aminosulfinyl group.

In some embodiments, a substituent α is an aminosulfonyl group.

In some embodiments, a substituent α is a hydroxy group.

In some embodiments, a substituent α is a hydroxyalkyl group having from 1 to 4 carbon atoms.

In some embodiments, a substituent α is a nitro group.

In some embodiments, a substituent α is an amino group.

In some embodiments, a substituent α is a carboxy group.

In some embodiments, a substituent α is an alkoxycarbonyl group having from 2 to 5 carbon atom.

In some embodiments, a substituent α is an alkoxyalkyl group having from 1 to 4 carbon atom.

In some embodiments, a substituent α is an alkylsulfonyl group having from 1 to 4 carbon atoms.

In some embodiments, a substituent α is an alkanoylamino group having from 1 to 4 carbon atoms.

In some embodiments, a substituent α is an alkanoyl (alkyl)amino group having from 1 to 6 carbon atoms.

In some embodiments, a substituent α is an alkanoylaminoalkyl group having from 1 to 6 carbon atoms in both the alkanoyl and alkyl part.

In some embodiments, a substituent α is an alkanoyl(alkyl)aminoalkyl group having from 1 to 6 carbon atoms in both the alkanoyl and each alkyl part.

In some embodiments, a substituent α is an alkylsulfonylamino group having from 1 to 4 carbon atoms.

In some embodiments, a substituent α is a mono- or di-alkylaminocarbonyl group having from 1 to 6 carbon atoms.

In some embodiments, a substituent α is a mono- or di-alkylaminosulfinyl group having from 1 to 6 carbon atom.

In some embodiments, a substituent α is a mono- or di-alkylaminosulfonyl group having from 1 to 6 carbon atom.

In some embodiments, a substituent α is an aminoalkyl group having from 1 to 4 carbon atoms.

In some embodiments, a substituent α is a mono- or di-alkylamino group having from 1 to 6 carbon atoms.

In some embodiments, a substituent α is a mono- or di-alkylaminoalkyl group having from 1 to 6 carbon atoms in each alkyl part.

In some embodiments, a substituent α is an aralkyl group having from 7 to 10 carbon atoms.

In some embodiments, a substituent α is a heteroarylalkyl group having from 1 to 4 carbon atoms in the alkyl part.

In some embodiments, a substituent α is a heteroarylalkoxy group having from 1 to 4 carbon atoms in the alkoxy part.

In some embodiments, a substituent α is an alkylsulfonylamino group having from 1 to 4 carbon atoms.

In some embodiments, two adjacent a groups are optionally joined together to form an alkylene or an alkenylene chain having 3 or 4 carbon atoms.

In some embodiments, two adjacent a groups are optionally joined together to form an alkylene chain having 3 or 4 carbon atoms. In some embodiments, two adjacent a groups are optionally joined together to form an alkenylene chain having 3 or 4 carbon atoms.

In some embodiments, said substituents α are selected from the group consisting halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent a groups are optionally joined together to form an alkylene chain having 3 carbon atoms, alkylthio groups having from 1 to 4 carbon atoms, and di-alkylaminoalkyl groups having from 1 to 6 carbon atoms in the alkyl part, said heteroaryl groups referred to in the definitions of a are unsubstituted or are substituted by alkyl groups having from 1 to 4 carbon atoms.

In some embodiments, said substituents α are selected from the group consisting of halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 4 carbon atoms, cycloalkyl groups having from 3 to 7 ring atoms, alkylthio groups having from 1 to 4 carbon atoms, di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups; said thiazolyl groups, isothiazolyl groups, oxazolyl groups, isoxazolyl groups, imidazolyl groups and pyridyl groups referred to in the definitions of a are unsubstituted or are substituted by alkyl groups having from 1 to 4 carbon atoms.

In some embodiments, said substituents α are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups.

In some embodiments, said substituents α are selected from those depicted in Table 2.

As defined generally above, said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups.

In some embodiments, a substituent β is a halogen atoms.

In some embodiments, a substituent β is an alkyl group having from 1 to 4 carbon atoms.

In some embodiments, a substituent β is an alkoxy group having from 1 to 4 carbon atoms.

In some embodiments, a substituent β is a haloalkyl group having from 1 to 4 carbon atoms.

In some embodiments, a substituent β is a haloalkoxy group having from 1 to 4 carbon atoms.

In some embodiments, a substituent β is a cyano group.

In some embodiments, said substituents β are selected from those as depicted in Table 2.

As defined generally above, W' is a pharmaceutically acceptable ester pro-drug group.

In some embodiments, W' is selected from those as depicted in Table 2.

In some embodiments, a compound of formula I' is a compound depicted in Table 2, or a pharmaceutically acceptable salt thereof.

TABLE 2

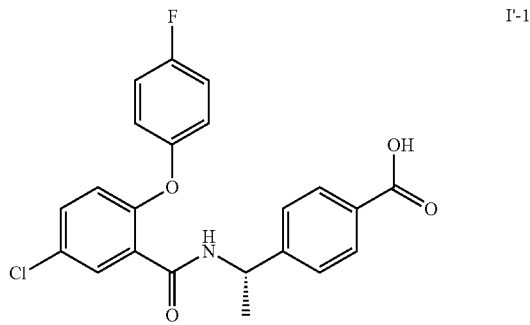

I'-1

TABLE 2-continued
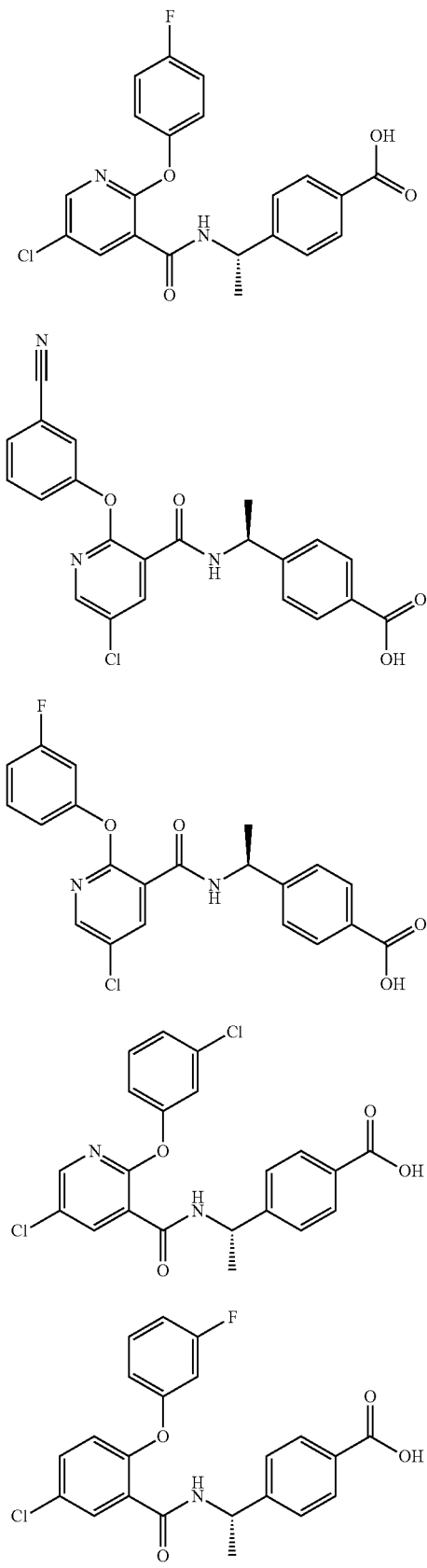
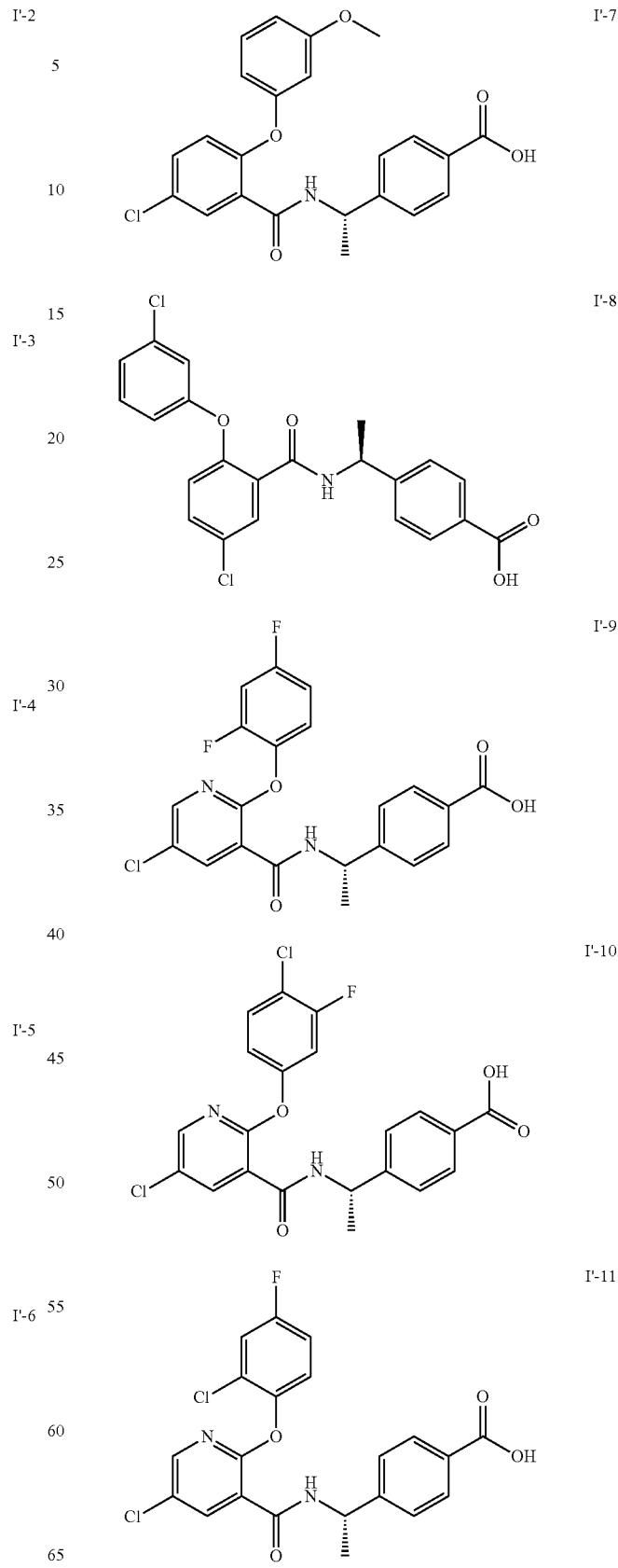

TABLE 2-continued
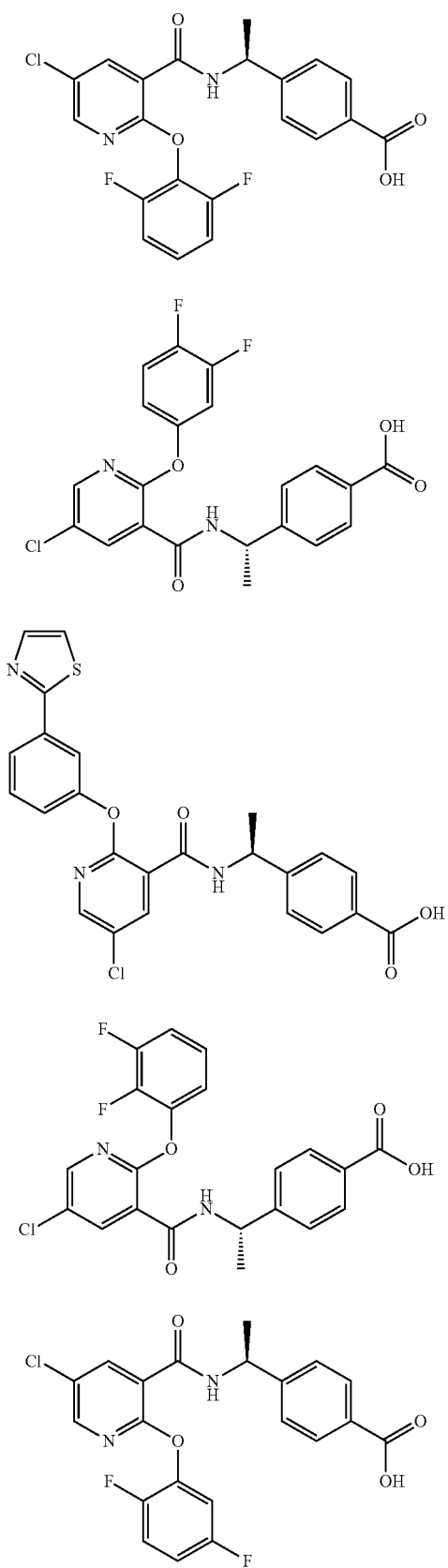
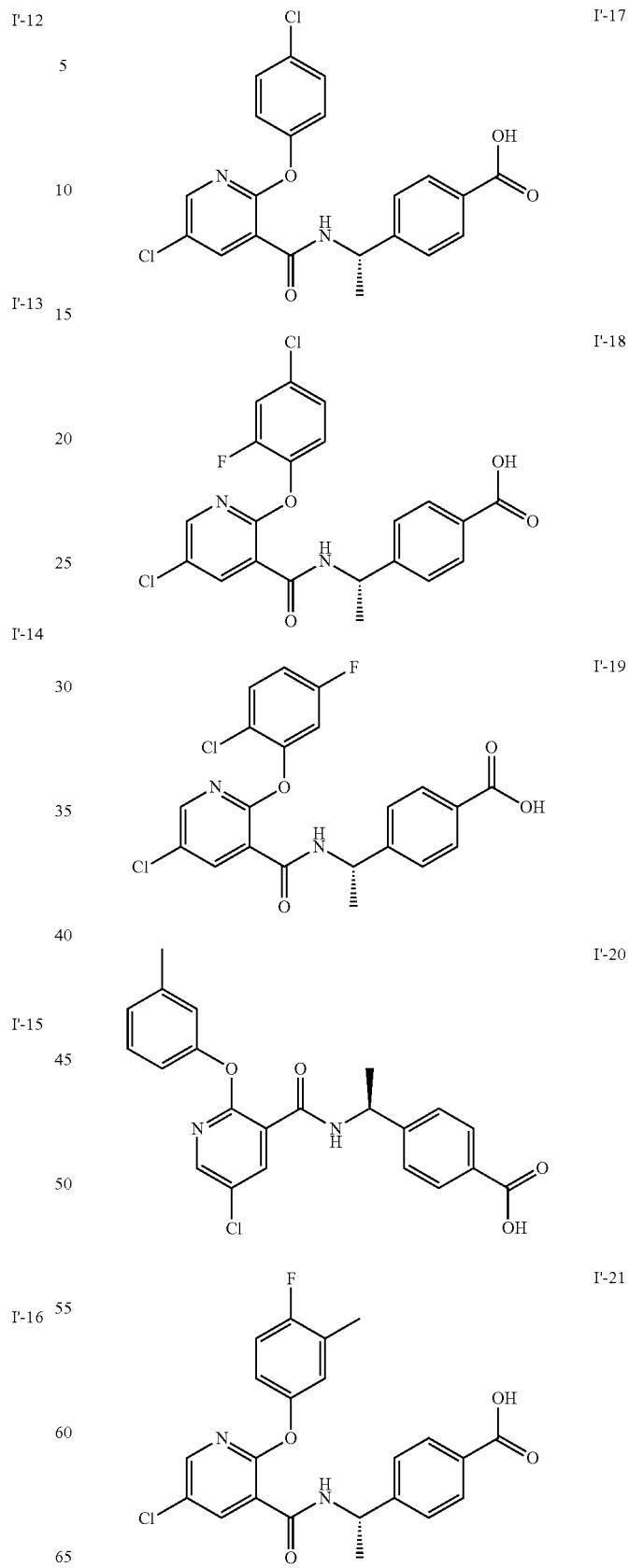

TABLE 2-continued
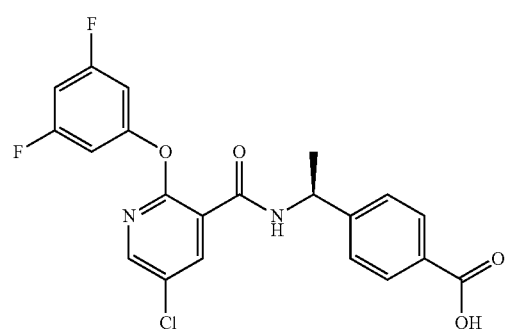 [SMILES: C[C@H](NC(=O)c1cc(Cl)cnc1Oc1cc(F)cc(F)c1)c1ccc(C(=O)O)cc1]
I'-22
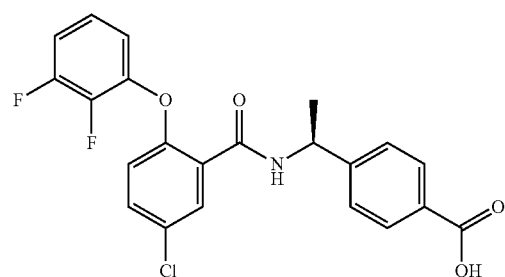 [SMILES: C[C@H](NC(=O)c1cc(Cl)ccc1Oc1cccc(F)c1F)c1ccc(C(=O)O)cc1]
I'-23
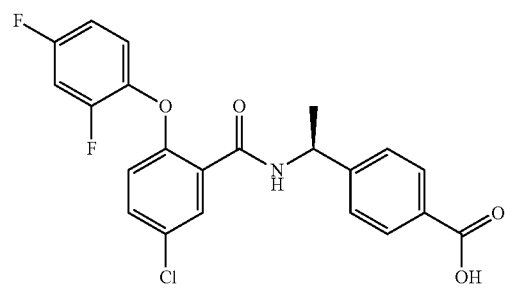 [SMILES: C[C@H](NC(=O)c1cc(Cl)ccc1Oc1ccc(F)cc1F)c1ccc(C(=O)O)cc1]
I'-24
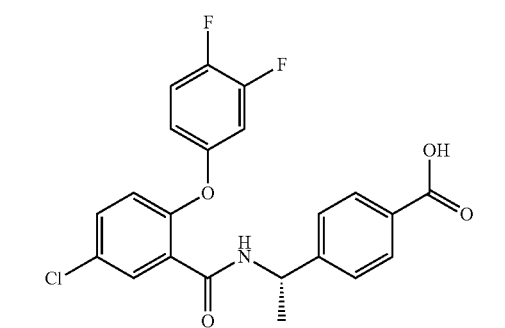 [SMILES: C[C@H](NC(=O)c1cc(Cl)ccc1Oc1ccc(F)c(F)c1)c1ccc(C(=O)O)cc1]
I'-25
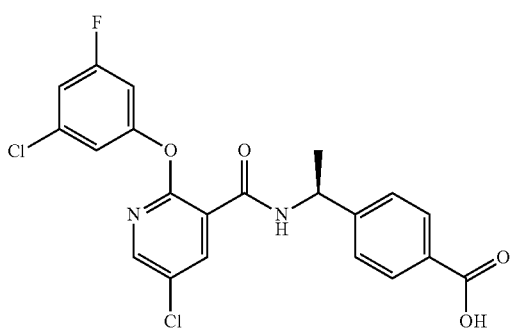 [SMILES: C[C@H](NC(=O)c1cc(Cl)cnc1Oc1cc(F)cc(Cl)c1)c1ccc(C(=O)O)cc1]
I'-26
TABLE 2-continued
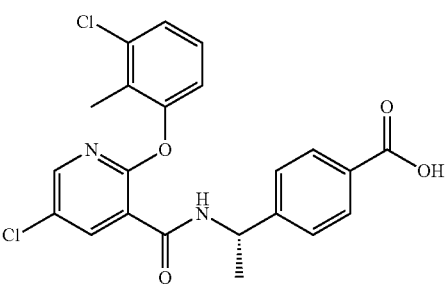 [SMILES: Cc1c(Cl)cccc1Oc1ncc(Cl)cc1C(=O)N[C@@H](C)c1ccc(C(=O)O)cc1]
I'-27
I'-28
I'-29
I'-30

TABLE 2-continued
I'-31
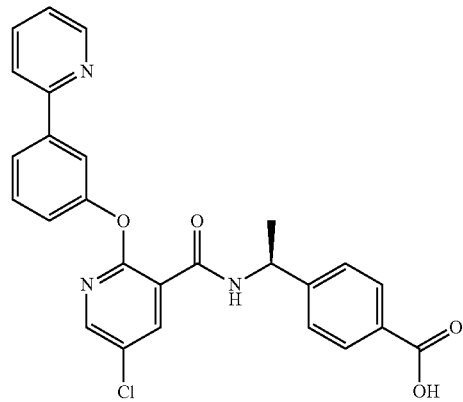 [SMILES: C[C@H](NC(=O)c1cc(Cl)cnc1Oc1cccc(-c2ccccn2)c1)c1ccc(C(=O)O)cc1]
I'-32
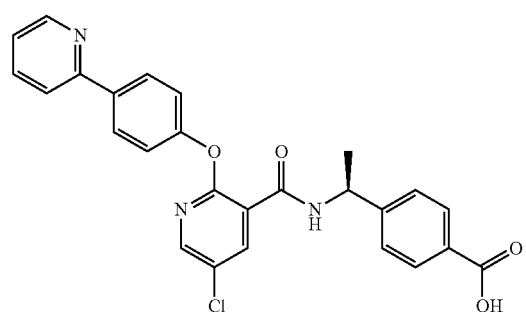 [SMILES: C[C@H](NC(=O)c1cc(Cl)cnc1Oc1ccc(-c2ccccn2)cc1)c1ccc(C(=O)O)cc1]
I'-33
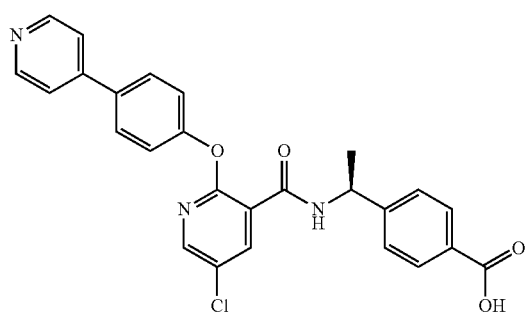 [SMILES: C[C@H](NC(=O)c1cc(Cl)cnc1Oc1ccc(-c2ccncc2)cc1)c1ccc(C(=O)O)cc1]
I'-34
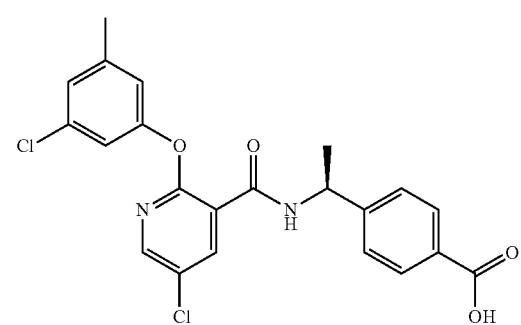 [SMILES: Cc1cc(Cl)cc(Oc2ncc(Cl)cc2C(=O)N[C@@H](C)c2ccc(C(=O)O)cc2)c1]
TABLE 2-continued
I'-35
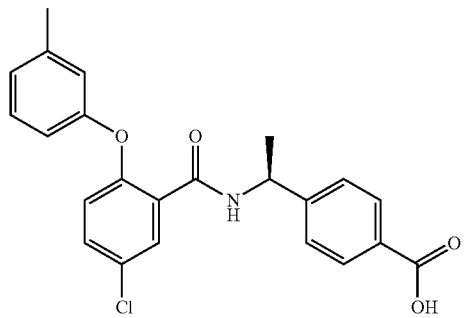 [SMILES: Cc1cccc(Oc2ccc(Cl)cc2C(=O)N[C@@H](C)c2ccc(C(=O)O)cc2)c1]
I'-36
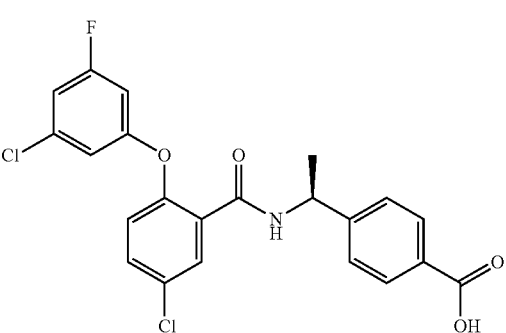 [SMILES: C[C@H](NC(=O)c1cc(Cl)ccc1Oc1cc(F)cc(Cl)c1)c1ccc(C(=O)O)cc1]
I'-37
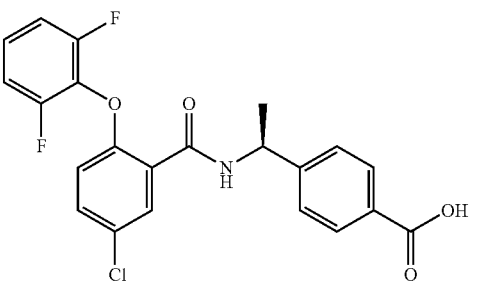 [SMILES: C[C@H](NC(=O)c1cc(Cl)ccc1Oc1c(F)cccc1F)c1ccc(C(=O)O)cc1]
I'-38
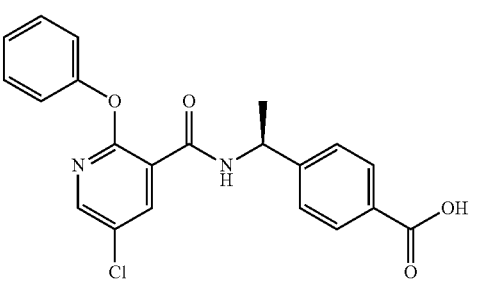 [SMILES: C[C@H](NC(=O)c1cc(Cl)cnc1Oc1ccccc1)c1ccc(C(=O)O)cc1]
I'-39
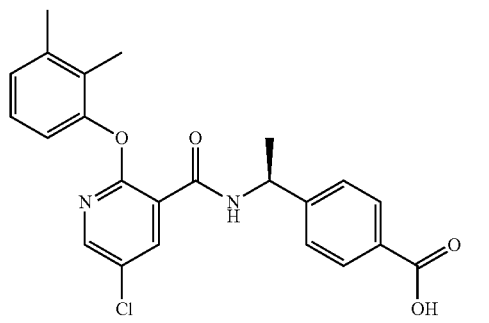 [SMILES: Cc1cccc(Oc2ncc(Cl)cc2C(=O)N[C@@H](C)c2ccc(C(=O)O)cc2)c1C]

TABLE 2-continued

I'-40

I'-41

I'-42

I'-43

In some embodiments, a compound of formula I' is a compound selected from the group consisting of I'-1 to I'-7, I'-8, I'-11 to I'-13, I'-15, I'-16, I'-18, I'-20, I'-22, I'-23, I'-25, I'-26, I'-28, I'-29, I'-34 to I'-38, I'-40 to I'-43, or a pharmaceutically acceptable salt thereof.

In some embodiments, an agent that inhibits EP4 activity is a compound of formula I', or a pharmaceutically acceptable salt thereof, wherein:

A' represents a phenyl group or a pyridyl group;

B' represents an aryl group or a heteroaryl group;

E' represents a 1,4-phenylene group;

$R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 2 to 6 carbon atoms;

$R^{5'}$ represents —$CO_2H$, —$CO_2W'$, or $R^{6'}$ represents an alkyl group having from 1 to 6 carbon atoms, a cycloalkyl group having from 3 to 7 ring atoms, an aryl group or a heteroaryl group;

X' represents a methylene group, an oxygen atom or a sulfur atom;

said aryl groups have from 6 to 10 carbon atoms;

said heteroaryl groups are 5- to 10-membered aromatic heterocyclic groups containing from 1 to 3 heteroatoms selected from the group consisting of sulfur atoms, oxygen atoms and nitrogen atoms; said aryl groups and said heteroaryl groups referred to in the definitions of B' are unsubstituted or are substituted by at least one substituent selected from the group consisting of substituents α;

said 1,4-phenylene group referred to in the definition of E' is unsubstituted or is substituted by at least one substituent selected from the group consisting of substituents β;

said aryl groups and said heteroaryl groups referred to in the definitions of $R^{6'}$ and α are unsubstituted or are substituted by at least one substituent selected from the group consisting of substituents β;

said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W' is a pharmaceutically acceptable ester pro-drug group; with the proviso $R^{1'}$ and $R^{2'}$ do not represent a hydrogen atom simultaneously.

In some embodiments, an agent that inhibits EP4 activity is a compound of formula (I'), or a pharmaceutically acceptable salt thereof, wherein E' represents an unsubstituted 1,4-phenylene group.

In some embodiments, an agent that inhibits EP4 activity is a compound of formula (I'), or a pharmaceutically acceptable salt thereof, wherein E' represents a 1,4-phenylene group substituted by at least one substituent selected from the group consisting of halogen atoms and alkyl groups having from 1 to 4 carbon atoms.

In some embodiments, an agent that inhibits EP4 activity is a compound of formula (I'), or a pharmaceutically acceptable salt thereof, wherein B' represents a phenyl or pyridyl group; said group is unsubstituted or is substituted by at least one substituent selected from the group consisting of substituents α; said substituents α are selected from the group consisting halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent a groups are optionally joined together to form an alkylene chain having 3 carbon atoms, alkylthio groups having from 1 to 4 carbon atoms, and di-alkylaminoalkyl groups having from 1 to 6 carbon atoms in the alkyl part; said heteroaryl groups referred to in the definitions of a are unsubstituted or are substituted by alkyl groups having from 1 to 4 carbon atoms.

In some embodiments, an agent that inhibits EP4 activity is a compound of formula I', or a pharmaceutically acceptable salt thereof, wherein B' represents a phenyl group optionally substituted by substituent selected from the group consisting of substituents α; said substituents α are selected from the group consisting of halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 4 carbon atoms, cycloalkyl groups having from 3 to 7 ring atoms, alkylthio groups having from 1 to 4 carbon atoms, di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups; said thiazolyl groups, isothiazolyl groups, oxazolyl groups, isoxazolyl groups, imidazolyl groups and pyridyl groups referred to in the definitions of a are unsubstituted or are substituted by alkyl groups having from 1 to 4 carbon atom.

In some embodiments, an agent that inhibits EP4 activity is a compound of formula (I'), or a pharmaceutically acceptable salt thereof, wherein B' represents a phenyl group optionally substituted by substituent selected from the group consisting of substituents α; said substituents α are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups.

In some embodiments, an agent that inhibits EP4 activity is a compound of formula (I'), or a pharmaceutically acceptable salt thereof, wherein X' represents a methylene group or an oxygen atom.

In some embodiments, an agent that inhibits EP4 activity is a compound of formula (I'), or a pharmaceutically acceptable salt thereof, wherein $R^{1'}$ represents a halogen atom and $R^{2'}$ represents a hydrogen atom.

In some embodiments, an agent that inhibits EP4 activity is a compound of formula (I'), or a pharmaceutically acceptable salt thereof, wherein $R^{3'}$ and $R^{4'}$ independently represent a hydrogen atom or an alkyl group having from 1 to 4 carbon atoms.

In some embodiments, an agent that inhibits EP4 activity is a compound of formula (I'), or a pharmaceutically acceptable salt thereof, wherein:

In some embodiments, an agent that inhibits EP4 activity is a compound of formula (I'), or a pharmaceutically acceptable salt thereof, wherein $R^{3'}$ represents an alkyl group having from 1 to 4 carbon atoms and $R^{4'}$ represents a hydrogen atom.

In some embodiments, an agent that inhibits EP4 activity is a compound of formula (I'), or a pharmaceutically acceptable salt thereof, wherein $R^{3'}$ represents a methyl group and $R^{4'}$ represents a hydrogen atom.

In some embodiments, an agent that inhibits EP4 activity is a compound of formula (I'), or a pharmaceutically acceptable salt thereof, wherein $R^{5'}$ represents —CO$_2$H,

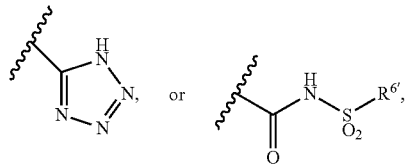

and $R^{6'}$ represents an aryl group optionally substituted by halogen atoms or an heteroaryl group.

In some embodiments, an agent that inhibits EP4 activity is a compound of formula (I'), or a pharmaceutically acceptable salt thereof, wherein $R^{5'}$ represents —CO$_2$H,

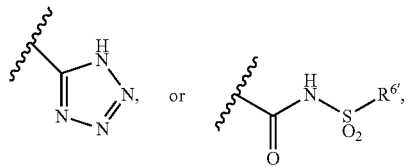

and $R^{6'}$ represents an aryl group optionally substituted by halogen atoms.

In some embodiments, an agent that inhibits EP4 activity is a compound of formula (I'), or a pharmaceutically acceptable salt thereof, wherein $R^{5'}$ represents —$CO_2H$,

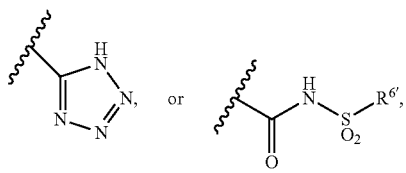

and $R^{6'}$ represents a phenyl group optionally substituted by halogen atoms.

In some embodiments, an agent that inhibits EP4 activity is a compound of formula (I'), or a pharmaceutically acceptable salt thereof, wherein $R^{5'}$ represents —$CO_2H$, or

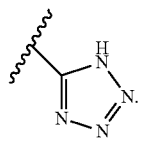

In some embodiments, an agent that inhibits EP4 activity is a compound of formula (II'):

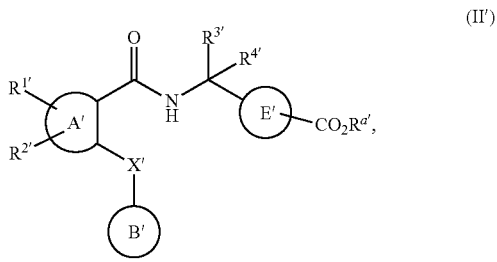

or a pharmaceutically acceptable salt thereof, wherein:
A' represents a phenyl group or a pyridyl group;
B' represents an aryl group or a heteroaryl group;
E' represents a 1,4-phenylene group;
$R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
$R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 2 to 6 carbon atoms;
$R^{a'}$ represents an alkyl groups having from 1 to 6 carbon atoms or an aralkyl group having from 7 to 12 carbon atoms;
X' represents a methylene group, an oxygen atom or a sulfur atom;
said aryl groups have from 6 to 10 carbon atoms;
said heteroaryl groups are 5- to 10-membered aromatic heterocyclic groups containing from 1 to 3 heteroatoms selected from the group consisting of sulfur atoms, oxygen atoms and nitrogen atoms;

said aryl groups and said heteroaryl groups referred to in the definitions of B' are unsubstituted or are substituted by at least one substituent selected from the group consisting of substituents α;
said 1,4-phenylene group referred to in the definition of E' is unsubstituted or is substituted by at least one substituent selected from the group consisting of substituents β; said aryl groups and said heteroaryl groups referred to in the definitions of $R^{6'}$ and α are unsubstituted or are substituted by at least one substituent selected from the group consisting of substituents β;
said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;
said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;
with the proviso $R^{1'}$ and $R^{2'}$ do not represent a hydrogen atom simultaneously.

As defined generally above, $R^{a'}$ represents an alkyl groups having from 1 to 6 carbon atoms or an aralkyl group having from 7 to 12 carbon atoms.

In some embodiments, $R^{a'}$ represents an alkyl groups having from 1 to 6 carbon atoms. In some embodiments, $R^{a'}$ represents an alkyl groups having from 1 to 5 carbon atoms. In some embodiments, $R^{a'}$ represents an alkyl groups having from 1 to 4 carbon atoms. In some embodiments, $R^{a'}$ represents an alkyl groups having from 1 to 3 carbon atoms.

In some embodiments, $R^{a'}$ is methyl. In some embodiments, $R^{a'}$ is ethyl. In some embodiments, $R^{a'}$ is propyl or isopropyl.

In some embodiments, $R^{a'}$ represents an aralkyl group having from 7 to 12 carbon atoms. In some embodiments, $R^{a'}$ represents an aralkyl group having from 7 to 11 carbon atoms. In some embodiments, $R^{a'}$ represents an aralkyl group having from 7 to 10 carbon atoms. In some embodiments, $R^{a'}$ represents an aralkyl group having from 7 to 9 carbon atoms. In some embodiments, $R^{a'}$ represents an aralkyl group having from 8 to 10 carbon atoms.

In some embodiments, $R^{a'}$ is selected from those as depicted in Table 2.

In some embodiments, an agent that inhibits EP4 activity is a compound of the formula (III'):

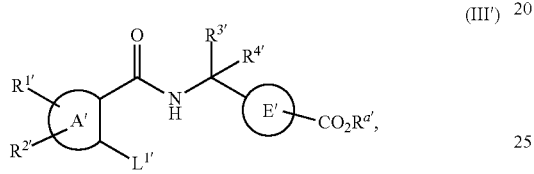

or a pharmaceutically acceptable salt thereof, wherein:

A' represents a phenyl group or a pyridyl group;

E' represents a 1,4-phenylene group;

$R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 2 to 6 carbon atoms;

$R^{a'}$ represents an alkyl groups having from 1 to 6 carbon atoms or an aralkyl group having from 7 to 12 carbon atoms;

$L^{1'}$ represents a halogen atom, an alkanesulfonyloxy group having from 1 to 4 carbon atoms, an arylsulfonyloxy group optionally substituted by an alkyl group having from 1 to 4 carbon atoms, a haloalkanesulfonyloxy group having from 1 to 4 carbon atoms or a boronic acid $(B(OH)_2)$ group;

said 1,4-phenylene group referred to in the definition of E' is unsubstituted or is substituted by at least one substituent selected from the group consisting of substituents β; said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

with the proviso $R^{1'}$ and $R^{2'}$ do not represent a hydrogen atom simultaneously.

In some embodiments, the agent that inhibits EP4 activity is a compound of the formula (I'):

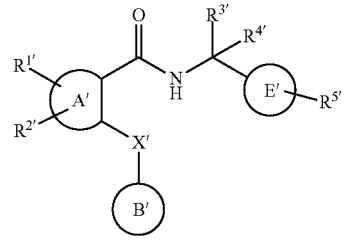

or a pharmaceutically acceptable ester or salt thereof, wherein:

A' represents a phenyl group or a pyridyl group;

B' represents an aryl group or a heteroaryl group;

E' represents a phenylene group;

$R^{1'}$ and $R^{2'}$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^{3'}$ and $R^{4'}$ independently represent a hydrogen atom or an alkyl group having from 1 to 4 carbon atoms; or $R^{3'}$ and $R^{4'}$ groups may be joined together to form an alkylene chain having 3 to 6 carbon atoms;

$R^{5'}$ represents —$CO_2H$,

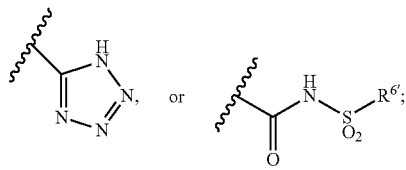

$R^{6'}$ represents an alkyl group having from 1 to 6 carbon atoms, a cycloalkyl group having from 3 to 7 ring atoms, an aryl group or a heteroaryl group;

X' represents a methylene group, an oxygen atom or a sulfur atom;

said aryl groups have from 6 to 10 carbon atoms;

said heteroaryl groups are 5- to 10-membered aromatic heterocyclic groups containing from 1 to 3 heteroatoms selected from the group consisting of sulfur atoms, oxygen atoms and nitrogen atoms;

said aryl groups and said heteroaryl groups referred to in the definitions of B' are unsubstituted or are substituted by at least one substituent selected from the group consisting of substituents;

said phenylene groups referred to in the definitions of E' are unsubstituted or are substituted by at least one substituent selected from the group consisting of substituents β;

said aryl groups and said heteroaryl groups referred to in the definitions of $R^{6'}$ and α are unsubstituted or are substituted by at least one substituent selected from the group consisting of substituents β;

said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in the alkanoyl and alkyl part, alkanoyl (alkyl)aminoalkyl groups having from 1 to 6 carbon atoms in the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in the alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part or alkylsulfonylamino groups having from 1 to 4 carbon atoms;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms or haloalkoxy groups having from 1 to 4 carbon atoms or cyano groups.

In some embodiments, E' represents an unsubstituted 1,4-phenylene group.

In some embodiments, E' represents a 1,4-phenylene group substituted by at least one substituent selected from the group consisting of halogen atoms and alkyl groups having from 1 to 4 carbon atoms.

In some embodiments, the agent that inhibits EP4 activity is compound B:

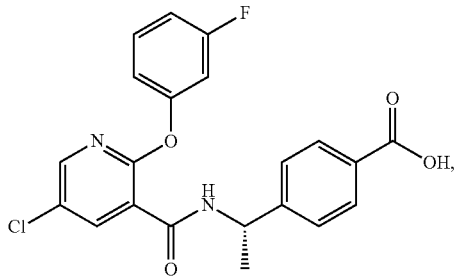 [SMILES: C[C@H](NC(=O)c1cc(Cl)cnc1Oc1cccc(F)c1)c1ccc(C(=O)O)cc1]

or a pharmaceutically acceptable salt thereof.

3. Exemplary Immuno-Oncology Agents

In certain embodiments, an immuno-oncology agent can be administered with an agent that inhibits EP4 activity for treatment of a proliferative disorder as described herein. As used herein, the term "an immuno-oncology agent" refers to an agent which is effective to enhance, stimulate, and/or up-regulate immune responses in a subject. In some embodiments, the administration of an immuno-oncology agent with an agent that inhibits EP4 activity has a synergic effect in treating cancer. In some embodiments, an agent that inhibits EP4 activity is compound A, or a pharmaceutically acceptable salt thereof. In some embodiments, an agent that inhibits EP4 activity is compound B, or a pharmaceutically acceptable salt thereof.

In some embodiments, an agent that inhibits EP4 activity is sequentially administered prior to administration of an immuno-oncology agent. In some embodiments, an agent that inhibits EP4 activity is administered concurrently with an immuno-oncology agent. In some embodiments, an agent that inhibits EP4 activity is sequentially administered after administration of an immuno-oncology agent.

In some embodiments, an agent that inhibits EP4 activity may be co-formulated with an immuno-oncology agent.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/ Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of an agent that inhibits EP4 activity, and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an IDO antagonist. In some embodiments, an IDO antagonist is INCB-024360 (WO2006/122150, WO07/75598, WO08/36653, WO08/36642), indoximod, or NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO006/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated:Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negatgive cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

3.1. Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PDI, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MED14736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MED11873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti- ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

4. Formulation and Administration 4.1. Pharmaceutically Acceptable Compositions

According some embodiments, the invention provides a composition comprising an agent that inhibits EP4 activity, an immuno-oncology agent, and a pharmaceutically acceptable carrier, adjuvant, or vehicle. In certain embodiments, the amount of an agent that inhibits EP4 activity in compositions of this invention is such that is effective to measurably inhibit EP4 activity, or a mutant thereof, in a biological sample or in a patient. In certain embodiments, a composition of this invention is formulated for administration to a patient in need of such composition. In some embodiments, a composition of this invention is formulated for oral administration to a patient. In some embodiments, an agent that inhibits prostaglandin EP4 receptor (EP4) activity is compound A, or a pharmaceutically acceptable salt thereof. In some embodiments, an agent that inhibits prostaglandin EP4 receptor (EP4) activity is compound B, or a pharmaceutically acceptable salt thereof.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

4.2. Administration

In some embodiments, an agent that inhibits EP4 activity and an immuno-oncology agent as described herein are administered in a single composition as a single dosage form. In some embodiments, an agent that inhibits EP4 activity and an immuno-oncology agent as described herein are administered separately as a multiple dosage regimen. If administered as a multiple dosage regime, the two agents may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, the two agents are administerd as a multiple dosage regimen within greater than 24 hours aparts. In some embodiments, an agent that inhibits EP4 activity is compound A, or a pharmaceutically acceptable salt thereof. In some embodiments, an agent that inhibits EP4 activity is compound B, or a pharmaceutically acceptable salt thereof.

As used herein, the term "combination," "combined," and related terms refers to the simultaneous or sequential administration of therapeutic agents in accordance with this invention. For example, an agent that inhibits EP4 activity may be administered with an immuno-oncology agent simultaneously or sequentially in separate unit dosage forms; or an agent that inhibits EP4 activity may be administered with an immuno-oncology agent simultaneously in a single unit dosage form. Accordingly, the present invention provides a single unit dosage form comprising an agent that inhibits EP4 activity, an immuno-oncology agent, and a pharmaceutically acceptable carrier, adjuvant, or vehicle.

The amount of an agent that inhibits EP4 activity and an immuno-oncology agent that may be combined with the carrier materials to produce a single dosage form will vary depending upon the host treated and the particular mode of administration. Preferably, compositions of this invention should be formulated so that a dosage of between 0.01-100 mg/kg body weight/day of each agent can be administered.

In some embodiments, an agent that inhibits EP4 activity and an immuno-oncology agent may act synergistically. Therefore, the amount of each agent will be less than that required in a monotherapy utilizing only that therapeutic agent. In such compositions a dosage of between about 50% to about 100% of the amount normally administered of each agent can be administered. In some embodiments, each agent is administered at a dosage of about 50%, about 55%, about 60%, about 65%, about 70%, about 75%, about 80%, about 85%, about 90%, or about 95% of the amount normally administered of each agent. As used herein, the phrase "normally administered" means the amount an FDA approved therapeutic agent is approvided for dosing per the FDA label insert.

The amount of each agent present in the compositions of this invention will be no more than the amount that would normally be administered in a composition comprising that therapeutic agent as the only active agent. In some embodiments, the amount of each agent in the presently disclosed compositions will range from about 50% to 100% of the amount normally present in a composition comprising that agent as the only therapeutically active agent.

In some embodiments, an agent that inhibits EP4 activity and/or an immuno-oncology agent as described in, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with an agent that inhibits EP4 activity and/or an immuno-oncology agent as described in, or pharmaceutical compositions thereof, are another embodiment of the present invention.

5. Uses

In some embodiments, the present invention provides a method for treating a proliferative disorder in a patient comprising administering to the patient an agent that inhibits prostaglandin EP4 receptor (EP4) activity in combination with an immuno-oncology agent, as described herein. In some embodiments, a proliferative disorder is a cancer selected from those as described herein. In some embodiments, a patient is a cancer patient who has been treated, or is being treated or to be treated, by immunotherapy. In some embodiments, a cancer patient is not pregnant or breastfeeding when receiving the instant treatment. In some embodiments, a cancer patient does not conceive children when receiving the instant treatment. In some embodiments, an agent that inhibits prostaglandin EP4 receptor (EP4) activity is compound A, or a pharmaceutically acceptable salt thereof. In some embodiments, an agent that inhibits prostaglandin EP4 receptor (EP4) activity is compound B, or a pharmaceutically acceptable salt thereof.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the cancer is non-small cell lung cancer (NSCLC). In some embodiments, the cancer is advanced and/or metastatic NSCLC. In some embodiments, the cancer is ovarian cancer. In some embodiments, the cancer is breast cancer. In some embodiments, the cancer is head and neck cancer. In some embodiments, the cancer is colorectal cancer (CRC). In some embodiments, the cancer is advanced or progressive microsatellite stable (MSS) CRC.

NSCLC Patients

In some embodiments, a cancer patient is a NSCLC patient. In some embodiments, a NSCLC patient has been treated by immunotherapy. In some embodiments, a NSCLC patient has been treated by PD-1/L1 immunotherapy. In some embodiments, a NSCLC patient has been treated by PD-1/L1 immunotherapy for a minimum of 12 weeks. In some embodiments, a NSCLC patient has progressed on PD-1/L1 immunotherapy given for a minimum of 12 weeks (aka post-PD-1/L1 NSCLC adenocarcinoma patients).

In some embodiments, a NSCLC patient has pathologically diagnosed adenocarcinoma histology of NSCLC.

In some embodiments, a NSCLC patient is an advanced (stage IIIb) and metastatic (stage IV) patient who has progressed clinically and/or radiographically per RECIST 1.1 (Response Evaluation Criteria in Solid Tumors).

In some embodiments, a NSCLC patient is at least 18 years old.

In some embodiments, a NSCLC patient has known PD-L1 positive status (>1%). In some embodiments, a NSCLC patient has a measurable disease as per RECIST 1.1. In some embodiments, a NSCLC patient has progression from a prior immunotherapy treatment with a PD-1 or PD-L1 antagonist given for a minimum of 12 weeks. In some embodiments, a prior immunotherapy may have been given with or without chemotherapy and may have been used in any line. In some embodiments, a NSCLC patient has one additional line of intervening chemotherapy following progression.

In some embodiments, a NSCLC patient has performance status of ECOG 0-1. In some embodiments, a NSCLC patient has ECOG performance status grade 0. In some embodiments, a NSCLC patient has ECOG performance status grade 1. ECOG performance status is discussed in Oken M, Creech R, Tormey D, et al. "Toxicity and response criteria of the Eastern Cooperative Oncology Group" *Am J Clin Oncol.* 1982; 5:649-655. ECOG performance status grade 0 refers to patients who are fully active, and are able to carry on all pre-disease performance without restriction. ECOG performance status grade 1 refers to patients who are restricted in physically strenuous activity but ambulatory and able to carry out work of a light or sedentary nature, e.g., light house work, office work.

In some embodiments, a NSCLC patient has adequate bone marrow, renal, and hepatic function as follows (within 7 days of starting therapy):

Absolute neutrophil count (ANC)≥1000/μL; and/or
Hemoglobin >9 g/dl; and/or
Platelet Count >75,000/μL; and/or
Serum creatinine ≤1.5× upper limit of normal (ULN) or glomerular filtration rate (GFR)≥40 mL/min for subject with creatinine levels >1.5× institutional ULN (using the Cockcroft-Gault formula); and/or
Serum total bilirubin ≤1.5×ULN or direct bilirubin ≤ULN for subjects with total bilirubin levels >1.5 ULN; and/or
Aspartate aminotransferase (AST) and alanine aminotransferase (ALT)≤2.5×ULN (or ≤5× if liver metastases are present).

In some embodiments, a NSCLC patient has recovered to grade 1 or baseline for all clinically significant on-going adverse events (AEs) from prior therapy.

In some embodiments, a NSCLC patient does not have recent (within the last 12 months) history of inflammatory bowel disease (IBD), including Crohn's disease and ulcerative colitis, or non-infectious interstitial lung disease.

In some embodiments, a NSCLC patient does not have current use of nonsteroidal anti-inflammatory drugs (NSAIDs) or cyclooxygenase-2 (COX-2) inhibitors within 3 days before treatment initiation or at any time during the study unless used for management of adverse events. In some embodiments, a NSCLC patient does not use an aspirin product, or only use it at prophylactic cardiovascular doses.

In some embodiments, a NSCLC patient does not have recent (within the last 12 months) or current gastrointestinal (GI) ulcer or colitis (other than IBD) or clinically significant autoimmune disease (i.e. severe) requiring continuous systemic immunosuppressive therapy.

In some embodiments, a NSCLC patient does not have a history of severe hypersensitivity reactions to PD-1 antibodies.

In some embodiments, a NSCLC patient has not received a live vaccine within 30 days prior to the planned first dose of the instant treatment.

In some embodiments, a NSCLC patient does not have any condition requiring continuous systemic treatment with either corticosteroids (>10 mg daily prednisone equivalents) or other immunosuppressive medications within 2 weeks prior to first dose of the instant treatment. In some embodiments, a NSCLC patient has inhaled or topical steroids and physiological replacement doses of up to 10 mg daily prednisone equivalent in the absence of active autoimmune disease.

In some embodiments, a NSCLC patient does not have a known EGFR, ALK, or ROS gene alteration.

In some embodiments, a NSCLC patient has a history of smoking.

In some embodiments, a NSCLC patient does not have uncontrolled or life-threatening symptomatic concomitant disease (including known symptomatic HIV, symptomatic Hepatitis B and C, or active tuberculosis [TB]).

In some embodiments, a NSCLC patient has not received chemotherapy or an investigational agent or device, or undergone a major surgery or systemic radiation within 3 weeks of starting the instant treatment, or had inadequate healing or recovery from complications of any of these prior to starting the instant treatment.

In some embodiments, a NSCLC patient has not had potentially life-threatening second malignancy within 3 years before starting the instant treatment.

In some embodiments, a NSCLC patient does not have clinically unstable central nervous system (CNS)/brain metastasis (treated or stable CNS metastases allowed).

In some embodiments, a NSCLC patient does not have any other concurrent antineoplastic treatment except for allowed local radiation of lesions for palliation (to be considered non-target lesions after treatment).

In some embodiments, a NSCLC patient does not have clinically significant (i.e., active) cardiovascular disease, including but not being limited to:

cerebral vascular accident/stroke (<6 months prior to enrollment); and/or
myocardial infarction (<6 months prior to enrollment); and/or
unstable angina; and/or
congestive heart failure (≥New York Heart Association Classification Class II); and/or
serious cardiac arrhythmia requiring medication.

In some embodiments, a NSCLC patient does not have medical conditions requiring concomitant administration of strong CYP3A4 or P-glycoprotein inhibitors or inducers.

In some embodiments, a NSCLC patient is not pregnant or breastfeeding, or expecting to conceive children during the instant treatment.

In some embodiments, a NSCLC patient is with advanced or metastatic Post-PD-1/L1 Non-Small Cell Lung Cancer (NSCLC) adenocarcinoma.

In some embodiments, a NSCLC patient is an adult patient diagnosed with NSCLC who has been previously treated for a minimum of 12 weeks with any PD-1 or PD-L1 checkpoint inhibitor.

In some embodiments, a NSCLC patient is treated with grapiprant at a starting dose level of 300 mg twice a day (BID). In some embodiments, a NSCLC patient is treated with grapiprant and pembrolizumab for up to 2 years.

In some embodiments, a NSCLC patient is an adult patient with a histologically confirmed non-small cell lung cancer (NSCLC) adenocarcinoma.

In some embodiments, a NSCLC patient has an advanced (stage IIIb) disease that is not amenable to curative intent treatment with concurrent chemoradiation and metastatic (stage IV) patients.

In some embodiments, a NSCLC patient has progressed clinically and/or radiographically per RECIST v1.1 after receiving a PD-1 or PD-L1 antagonist for a minimum of 12 weeks. In some embodiments, a NSCLC patient has received Immunotherapy with chemotherapy. In some embodiments, a NSCLC patient has received Immunotherapy without chemotherapy. In some embodiments, a NSCLC patient has received Immunotherapy in any line. In some embodiments, a NSCLC patient has received no more than one prior regimen of immunotherapy.

In some embodiments, a NSCLC patient has measurable disease per RECIST v1.1 as assessed by the local site investigator/radiology. In some embodiments, lesions situated in a previously irradiated area are considered measurable if progression has been demonstrated in such lesions.

In some embodiments, a NSCLC patient has a disease that can be safely accessed via bronchoscopic, thoracoscopic or percutaneous biopsy for multiple core biopsies (minimum of 3 passes per biopsy).

In some embodiments, a NSCLC patient has an Eastern Cooperative Oncology Group (ECOG) performance status of 0 to 1.

In some embodiments, a NSCLC patient has adequate organ function as defined in Table A below.

In some embodiments, a NSCLC patient does not use NSAIDs (eg, ibuprophen, naproxen), COX-2 inhibitors (eg, celecoxib) within 3 days before treatment initiation or at any time during the treatment. In some embodiments, a NSCLC patient uses NSAIDs (eg, ibuprophen, naproxen), COX-2 inhibitors (eg, celecoxib) within 3 days before treatment initiation or at any time during the treatment for management of AE. In some embodiments, a NSCLC patient uses Aspirin products that is limited to prophylactic cardiovascular doses.

In some embodiments, a NSCLC patient does not have a known epidermal growth factor receptor (EGFR), anaplastic lymphoma kinase (ALK), or ROS gene alteration.

In some embodiments, a NSCLC patient does not have a known BRAF gene mutation.

In some embodiments, a NSCLC patient has a history of smoking (>100 cigarettes lifetime).

In some embodiments, a NSCLC patient does not have a history of severe hypersensitivity reactions to a PD-1/L1 antibody.

In some embodiments, a NSCLC patient has not received prior systemic anti-cancer therapy including investigational agents within 4 weeks prior to treatment. In some embodiments, a NSCLC patient has recovered from all AEs due to previous therapies to ≤Grade 1 or baseline. In some embodiments, a NSCLC patient has ≤Grade 2 neuropathy.

In some embodiments, a NSCLC patient has not received prior radiotherapy within 2 weeks of start of a treatment of the invention. In some embodiments, a NSCLC patient has recovered from all radiation-related toxicities, not require corticosteroids, and not have had radiation pneumonitis. In some embodiments, a NSCLC patient has a 1-week washout for palliative radiation (≤2 weeks of radiotherapy) to non-central nervous system (CNS) disease. In some embodiments, a NSCLC patient does not receive any antineoplastic treatment during a treatment of the invention, except for allowed local radiation of lesions for palliation only (to be considered non-target lesions after treatment). In some embodiments, a NSCLC patient has received a surgery, and recovered fully from the toxicity and/or complications from the intervention prior to starting a treatment of the invention.

In some embodiments, a NSCLC patient has not received a live vaccine within 30 days prior to the first dose of study treatment.

In some embodiments, a NSCLC patient has not taken strong CYP3A4 or P-glycoprotein inhibitors or inducers prior to and during a treatment of the invention. In some embodiments, a NSCLC patient has taken strong CYP3A4 or P-glycoprotein inhibitors or inducers, but transferred to other medications within ≥5 half-lives prior to dosing of a treatment of the invention.

In some embodiments, a NSCLC patient does not participate in or has not participated in a study of an investigational agent within 4 weeks prior to the first dose of a treatment of the invention. In some embodiments, a NSCLC patient has not used an investigational device within 4 weeks prior to the first dose of a treatment of the invention.

In some embodiments, a NSCLC patient does not have a diagnosis of immunodeficiency. In some embodiments, a NSCLC patient is not receiving chronic systemic steroid therapy (in dosing exceeding 10 mg daily of prednisone equivalent), or any other form of immunosuppressive therapy, within 7 days prior the first dose of a treatment of the invention.

In some embodiments, a NSCLC patient does not have a known additional potentially life-threatening malignancy that is progressing or has required active treatment within 3 years prior to the first dose of a treatment of the invention. In some embodiments, a NSCLC patient has a basal cell carcinoma of the skin. In some embodiments, a NSCLC patient has squamous cell carcinoma of the skin. In some embodiments, a NSCLC patient has carcinoma in situ (eg, breast carcinoma, cervical cancer in situ) that have undergone potentially curative therapy.

In some embodiments, a NSCLC patient does not have known active CNS metastases and/or carcinomatous meningitis (clinically stable and/or previously treated inactive CNS metastases allowed).

In some embodiments, a NSCLC patient does not have an active autoimmune disease that has required systemic treatment in past 2 years (ie, with use of disease modifying agents, corticosteroids or immunosuppressive drugs). In some embodiments, a systemic treatment is not replacement therapy (eg, thyroxine, insulin, or physiologic corticosteroid replacement therapy for adrenal or pituitary insufficiency). In some embodiments, an autoimmune disease is inflammatory bowel disease (IBD) such as Crohn's disease and ulcerative colitis.

In some embodiments, a NSCLC patient does not have a history of (non-infectious) pneumonitis that required steroids or has current pneumonitis.

In some embodiments, a NSCLC patient does not have an active infection requiring systemic therapy.

In some embodiments, a NSCLC patient does not have recent (within the last 12 months) or current GI ulcer or colitis or non-immune colitis.

In some embodiments, a NSCLC patient does not have a known history of human immunodeficiency virus (HIV) infection.

In some embodiments, a NSCLC patient does not have a known history of Hepatitis B or known active Hepatitis C virus infection.

In some embodiments, a NSCLC patient does not have clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.

In some embodiments, a NSCLC patient does not have a known psychiatric or substance abuse disorder that would interfere with cooperating with a treatment of the invention.

In some embodiments, a NSCLC patient is not a woman of childbearing potential (WOCBP) who has a positive pregnancy test prior to a treatment of the invention.

In some embodiments, a NSCLC patient is not breastfeeding or expecting to conceive or father children within the projected duration of a treatment of the invention.

CRC Patients

In some embodiments, a CRC patient is histologically confirmed advanced, metastatic, or progressive colorectal cancer (CRC). In some embodiments, microsatellite stable disease (MSS) is based on prior PCR or immunohistochemistry results.

In some embodiments, a CRC patient is at least 18 years old.

In some embodiments, a CRC patient has progressed on first line 5-FU based therapy, refused therapy or is intolerable to 5-FU based therapy.

In some embodiments, a CRC patient has a measurable disease as per RECIST 1.1 (Response Evaluation Criteria in Solid Tumors).

In some embodiments, a CRC patient has a performance status of ECOG 0-1. In some embodiments, a CRC patient has ECOG performance status grade 0. In some embodiments, a CRC patient has ECOG performance status grade 1.

In some embodiments, a CRC patient has adequate bone marrow, renal, and hepatic function as follows (within 7 days of starting therapy):
  Absolute neutrophil count (ANC)≥1000/µL; and/or
  Hemoglobin >9 g/dl; and/or
  Platelet Count >75,000/l; and/or
  Serum creatinine ≤1.5× upper limit of normal (ULN) or glomerular filtration rate (GFR) ≥40 mL/min for subject with creatinine levels >1.5× institutional ULN (using the Cockcroft-Gault formula); and/or
  Serum total bilirubin ≤1.5×ULN or direct bilirubin ≤ULN for subjects with total bilirubin levels >1.5 ULN; and/or
  Aspartate aminotransferase (AST) and alanine aminotransferase (ALT)≤2.5×ULN (or ≤5× if liver metastases are present).

In some embodiments, a CRC patient has recovered to Grade 1 or baseline for all clinically significant on-going adverse events (AEs) from prior therapy.

In some embodiments, a CRC patient has completed previous treatment (including other investigational therapy) at least 3 weeks before initiation of the instant treatment.

In some embodiments, a CRC patient has not been treated with an anti-PD-1, anti-PD-L1, or anti-PD-L2 therapeutic antibody.

In some embodiments, a CRC patient has not used non-steroidal anti-inflammatory drugs (NSAIDs) or cyclooxygenase-2 (COX-2) inhibitors within 3 days before initiation of the instant treatment, or at any time during the instant treatment, unless used for management of AE. In some embodiments, a CRC patient does not use any aspirin product, or only use it at prophylactic cardiovascular doses.

In some embodiments, a CRC patient does not have a recent (within the last 12 months) history of inflammatory bowel disease (IBD), including Crohn's disease and ulcerative colitis, or non-infectious interstitial lung disease.

In some embodiments, a CRC patient does not have recent (within the last 12 months) or current gastrointestinal (GI) ulcer or colitis (other than IBD) or clinically significant autoimmune disease (i.e. severe) requiring continuous systemic immunosuppressive therapy.

In some embodiments, a CRC patient does not have any condition requiring continuous systemic treatment with either corticosteroids (>10 mg daily prednisone equivalents) or other immunosuppressive medications within 2 weeks prior to first dose of the instant treatment. In some embodiments, a CRC patient takes inhaled or topical steroids and physiological replacement doses of up to 10 mg daily prednisone equivalent in the absence of active clinically significant (severe) autoimmune disease.

In some embodiments, a CRC patient does not have a history of severe hypersensitivity reactions to chimeric or humanized antibodies.

In some embodiments, a CRC patient has not received a live vaccine within 30 days prior to the first dose of the instant treatment.

In some embodiments, a CRC patient does not receive any other concurrent antineoplastic treatment except for allowed local radiation of lesions for palliation only (to be considered non-target lesions after treatment).

In some embodiments, a CRC patient does not have uncontrolled or life-threatening symptomatic concomitant disease (including known symptomatic HIV, symptomatic Hepatitis B and C, or active tuberculosis [TB]).

In some embodiments, a CRC patient has not undergone a major surgery or systemic radiation within 3 weeks of starting the instant treatment or has inadequate healing or recovery from complications of surgery or radiation prior to starting the instant treatment.

In some embodiments, a CRC patient has not had a potentially life-threatening second malignancy within the last 3 years.

In some embodiments, a CRC patient does not have clinically unstable central nervous system (CNS)/brain metastasis (treated or stable CNS metastases allowed).

In some embodiments, a CRC patient has not had a clinically significant (i.e., active) cardiovascular disease, including but not being limited to:
  cerebral vascular accident/stroke (<6 months prior to enrollment); and/or
  myocardial infarction (<6 months prior to enrollment); and/or
  unstable angina; and/or
  congestive heart failure (≥New York Heart Association Classification Class II); and/or
  serious cardiac arrhythmia requiring medication.

In some embodiments, a CRC patient does not have medical conditions requiring concomitant administration of strong CYP3A4 or P-glycoprotein inhibitors or inducers.

In some embodiments, a CRC patient is with advanced or progressive MSS CRC.

In some embodiments, a CRC patient is treated at a starting dose of Grapiprant 300 mg administered orally twice a day (BID).

In some embodiments, a CRC patient is treated with grapiprant 300 mg administered orally BID, and pembrolizumab administered 200 mg IV every 3 weeks (Q3W).

In some embodiments, a CRC patient is an adult patient with a histologically confirmed advanced, metastatic, or progressive CRC that is MSS. In some embodiments, microsatellite stability is based on prior polymerase chain reaction (PCR), Next-Gen sequencing, or immunohistochemistry results per institutional standards.

In some embodiments, a CRC patient has received at least two prior lines of therapy for advanced or metastatic CRC, at least one of which included fluorouracil. In some embodiments, a CRC patient has received adjuvant therapy, and progression occurs within 6 months of its completion.

In some embodiments, a CRC patient has measurable disease per RECIST v1.1 as assessed by the local site investigator/radiology. In some embodiments, lesions situated in a previously irradiated area are considered measurable if progression has been demonstrated in such lesions.

In some embodiments, a CRC patient has an accessible tumor that can be safely accessed for multiple core biopsies.

In some embodiments, a CRC patient has an Eastern Cooperative Oncology Group (ECOG) performance status of 0 to 1.

In some embodiments, a CRC patient has adequate organ function as defined in Table A below.

In some embodiments, a CRC patient is able to swallow and absorb oral tablets.

In some embodiments, a CRC patient is a woman who is not postmenopausal and uses contraception, or a man.

In some embodiments, a CRC patient has not received prior therapy with an anti-PD-1, anti-PD-L1, or anti-PD-L2 agent or with an agent directed to another stimulatory or co-inhibitory T-cell receptor (eg, CTLA-4, OX 40, CD137).

In some embodiments, a CRC patient does not use NSAIDs (eg, ibuprophen, naproxen), COX-2 inhibitors (eg, celecoxib) within 3 days before initiation of a treatment of the invention, or at any time during a treatment of the invention. In some embodiments, a CRC patient uses NSAIDs (eg, ibuprophen, naproxen), COX-2 inhibitors (eg, celecoxib) for management of AE of a treatment of the invention. In some embodiments, a CRC patient uses an aspirin product that is limited to prophylactic cardiovascular doses.

In some embodiments, a CRC patient does not have history of severe hypersensitivity reactions to chimeric or humanized antibodies.

In some embodiments, a CRC patient has not received prior systemic anti-cancer therapy including investigational agents within 4 weeks (or 5 half-lives, whichever is shorter) prior to a treatment of the invention. In some embodiments, a CRC patient has recovered from all AEs due to previous therapies to ≤Grade 1 or baseline. In some embodiments, a CRC patient is with ≤Grade 2 neuropathy. In some embodiments, a CRC patient has received major surgery, and has fully recovered from the toxicity and/or complications from the intervention prior to starting a treatment of the invention.

In some embodiments, a CRC patient has not received prior radiotherapy within 2 weeks of start of a treatment of the invention. In some embodiments, a CRC patient has recovered from all radiation-related toxicities, does not require corticosteroids, and has not had radiation pneumonitis. In some embodiments, a CRC patient has a 1-week washout for palliative radiation (≤2 weeks of radiotherapy) to non-central nervous system (CNS) disease. In some embodiments, a CRC patient does not receive antineoplastic treatment concurrently with a treatment of the invention. In some embodiments, a CRC patient receives antineoplastic treatment for local radiation of lesions for palliation only (to be considered non-target lesions after treatment).

In some embodiments, a CRC patient has not received a live vaccine within 30 days prior to the first dose of a treatment of the invention.

In some embodiments, a CRC patient does not take strong CYP3A4 or P-glycoprotein inhibitors or inducers. In some embodiments, a CRC patient has taken strong CYP3A4 or P-glycoprotein inhibitors or inducers, but transferred to other medications within >5 half-lives prior to dosing of a treatment of the invention.

In some embodiments, a CRC patient does not participate in, or has not participated in, a study of an investigational agent within 4 weeks prior to the first dose of a treatment of the invention. In some embodiments, a CRC patient has not used an investigational device within 4 weeks prior to the first dose of a treatment of the invention.

In some embodiments, a CRC patient does not have a diagnosis of immunodeficiency. In some embodiments, a CRC patient does not receive chronic systemic steroid therapy (in dosing exceeding 10 mg daily of prednisone equivalent), or any other form of immunosuppressive therapy, within 7 days prior to the first dose of a treatment of the invention.

In some embodiments, a CRC patient does not have a known additional potentially life-threatening malignancy that is progressing or has required active treatment within 3 years prior to start of a treatment of the invention. In some embodiments, a CRC patient has basal cell carcinoma of the skin. In some embodiments, a CRC patient has squamous cell carcinoma of the skin. In some embodiments, a CRC patient has carcinoma in situ (eg, breast carcinoma, cervical cancer in situ) that has undergone potentially curative therapy.

In some embodiments, a CRC patient does not have known active CNS metastases and/or carcinomatous meningitis. In some embodiments, a CRC patient is with previously treated brain metastases and is radiologically stable, ie, without evidence of progression for at least 4 weeks by repeat imaging (note that the repeat imaging should be performed during study screening), and/or clinically stable and without requirement of steroid treatment for at least 14 days prior to first dose of a treatment of the invention.

In some embodiments, a CRC patient does not have an active autoimmune disease that has required systemic treatment (ie, with use of disease modifying agents, corticosteroids or immunosuppressive drugs) in 2 years prior to start of a treatment of the invention. In some embodiments, a CRC patient has received replacement therapy (eg, thyroxine, insulin, or physiologic corticosteroid replacement therapy for adrenal or pituitary insufficiency) in 2 years prior to start of a treatment of the invention. In some embodiments, an autoimmune disease includes but is not limited to inflammatory bowel disease (IBD) such as Crohn's disease and ulcerative colitis.

In some embodiments, a CRC patient does not have a history of (non-infectious) pneumonitis that required steroids or has current pneumonitis.

In some embodiments, a CRC patient does not have an active infection requiring systemic therapy.

In some embodiments, a CRC patient does not have recent (within 12 months from start of a treatment of the invention) or current GI ulcer or non-immune colitis.

In some embodiments, a CRC patient does not have a known history of human immunodeficiency virus (HIV) infection.

In some embodiments, a CRC patient does not have a known history of Hepatitis B or known active Hepatitis C virus infection.

In some embodiments, a CRC patient does not have clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.

In some embodiments, a CRC patient does not have a known psychiatric or substance abuse disorder that would interfere with cooperating with a treatment of the invention.

In some embodiments, a CRC patient is not a woman of childbearing potential (WOCBP) who has a positive pregnancy test prior to a treatment of the invention.

In some embodiments, a CRC patient does not breastfeed or expect to conceive or father children within a treatment of the invention.

Cancer

Cancer includes, in some embodiments, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrom Macroglobulinemia, or Wilms Tumor.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

In some embodiments, the cancer is small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In some embodiments, the cancer is small cell lung cancer, non-small cell lung cancer, colorectal cancer, multiple myeloma, or AML.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a tumor in a patient in need thereof, comprising administering to the patient an agent that inhibits prostaglandin EP4 receptor (EP4) activity and an immuno-oncology agent as described herein, or pharmaceutical compositions thereof described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments, the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

The compounds and compositions, according to the method of the present invention, may be administered using any amount and any route of administration effective for treating or lessening the severity of a cancer. The exact amount required will vary from subject to subject, depending on the species, age, and general condition of the subject, the severity of the disease or condition, the particular agent, its mode of administration, and the like. The compounds and compositions, according to the method of the present invention, are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

EXEMPLIFICATION

The following examples are intended to illustrate the invention and are not to be construed as being limitations thereon.

The agents that inhibit EP4 activity and immuno-oncology agents can be prepared by methods known to one of ordinary skill in the art. For example, the agents that inhibit EP4 activity can be synthesized as described in WO 2002/032900, WO 2005/021508, and U.S. Pat. Nos. 6,710,054 and 7,960,407, the contents of which are incorporated herein by reference in their entireties. Exemplary protocols for preparing polymorph form A of compound A are described in U.S. Pat. Nos. 7,960,407 and 9,265,756, the contents of which are incorporated herein by reference in their entireties. Unless otherwise stated, one or more tautomeric forms of compounds of the examples described hereinafter may be prepared in situ and/or isolated. All tautomeric forms of compounds of the examples described hereafter should be considered to be disclosed.

Example 1: Protocols for Preparing Polymorph Form A of Compound A 1.1 Protocol 1 (as Described in U.S. Pat. No. 7,960,407)

Step 1: Crude Amorphous Product

In a 4-necked round bottom flask equipped with a mechanical stirrer, thermometer, and two dropping funnels is immersed in a water bath (water bath temperature 18° C.). In the flask, to a solution of 2-[4-(2-ethyl-4,6-dimethyl-1H-imidazo[4,5-c]pyridin-1-yl)phenyl]ethanamine and triethylamine in $CH_2Cl_2$ is added p-tosyl isocyanate dropwise slowly from one of the dropping funnel maintaining the internal temperature below 28° C. The resulting solution is stirred at room temperature, then aqueous citric acid solution is added dropwise maintaining the internal temperature below 22° C. The resulting mixture is stirred vigorously at room temperature, then aqueous NaOH solution is added dropwise. After the completion of the addition, pH value of the solution is confirmed to be 5-5.5. The layers are then separated, and the aqueous layer is re-extracted with $CH_2Cl_2$ and the organic layer is combined. The organic layer is washed with the mixture of aqueous solution of citric acid and aqueous NaOH solution. After layers are separated, the aqueous layer is re-extracted with $CH_2Cl_2$ and the organic layer is combined. The resulting organic layer is added $Na_2SO_4$ and of charcoal, and the mixture is stirred gently at room temperature. After the mixture is filtered through celite pad, it is concentrated to give the crude product.

Step 2: Conversion to, and Purification of Polymorph Form A

In a round bottom, 4-necked flask equipped with a mechanical stirrer, thermometer and reflux condenser is immersed in a water bath. In the flask, hot (40° C.) acetone is added to the crude N-[({2-[4-(2-ethyl-4,6-dimethyl-1H-imidazo[4,5-c]pyridin-1-yl)phenyl]ethyl}amino) carbonyl]-4-methylbenzenesulfonamide (Step 1). The mixture is stirred at 50° C. under nitrogen atmosphere, then cooled slowly to room temperature. Acetone is added and the mixture is stirred at room temperature under nitrogen atmosphere. The crystals are filtered through paper filter, washed with acetone and dried by flowing nitrogen gas to give crystals of the title compound, which are further purified by the following procedure.

In a stainless 3-necked reactor equipped with a mechanical stirrer, thermometer and reflux condenser is immersed in a water bath. In the flask, a mixture (suspension) of the above compound in acetone is stirred at 50° C., then cooled to room temperature. Aliquot is taken out and crystals are collected by suction to prepare a sample for the HPLC analysis to determine the purity of the crystal. The mixture is stirred at room temperature under nitrogen atmosphere. The crystals are filtered off using a paper filter, washed with acetone, dried by flowing nitrogen gas and dried under reduced pressure at 40° C. The product is further purified by the following procedure.

In a round bottom, 4-necked flask equipped with a mechanical stirrer, thermometer and reflux condenser is immersed in a water bath. In the flask, acetone is added to the aforementioned crystals. The mixture is stirred at 50° C. under nitrogen atmosphere, then, cooled slowly to room temperature. Aliquot is taken out and crystals are collected by suction to prepare a sample for the HPLC analysis to determine the purity of the crystal. The mixture is stirred at room temperature under nitrogen atmosphere. The crystals are filtered through paper filter, washed with acetone, dried by flowing nitrogen gas, and dried under reduced pressure at 40° C. to give the title compound, Polymorph Form A.

1.2 Protocol 2 (as Described in U.S. Pat. No. 7,960,407)

To a clean and dry 3-neck round-bottom flask are charged 2-[4-(2-ethyl-4,6-dimethyl-1H-imidazo[4,5-c]pyridin-1-yl) phenyl]ethanamine and $CH_2Cl_2$. Tosyl isocyanate dissolved in $CH_2Cl_2$ is added to the reaction keeping the temperature below 21° C. and is stirred. The reaction is deemed complete by HPLC, and activated charcoal is added. The resulting slurry is filtered through a 0.5-micron filter into a speck free 3-neck round-bottom flask and the filter washed with $CH_2Cl_2$. The reaction is atmospherically concentrated to a minimum stirable volume and displacement continued with speck freed acetone until an internal temperature of 58° C. to 62° C. is achieved. The reaction is cooled to at least 30° C. and seed of N-[({2-[4-(2-Ethyl-4,6-dimethyl-1H-imidazo[4,5-c]pyridin-1-yl)phenyl]ethyl}amino)carbonyl]-4-methylbenzenesulfonamide Polymorph Form A is added. The reaction is allowed to granulate between 20° C. and 25° C. After cooling reaction to 0° C. to 5° C. and granulating, the reaction is filtered on a speck free filter. The solids are washed two times with speck free acetone cooled to 0° C. to 5° C. The wet-cake is returned to a speck free 3-neck round-bottom flask and speck free ethyl acetate is added. The slurry is heated to at least 75° C. and held for some time. The reaction is cooled to at least 30° C. and the solids are filtered on a speck free filter. The solids are washed with speck free ethyl acetate. The wet-cake is returned to the same speck free 3-neck round-bottom flask and speck free ethyl acetate is added. The slurry is heated to at least 75° C. and held for some time. The reaction is cooled to at least 30° C. and the solids are filtered on a speck free filter. The solids are washed with speck free ethyl acetate. The product is dried at 45° C. to 50° C. to yield the title product, Polymorph Form A.

The particle size generated by the above methodology generates a particle size that does not require milling. A simple hand-sieving process removes any lumps. The product is hand sieved through a speck free #25 hand sieve with 0.0278-inch openings.

1.3 Protocol 3 (as Described in U.S. Pat. No. 9,265,756)

Polymorph form A of compound A is prepared by slurry of Form J of compound A in 1:2 dichloromethane/acetone (v/v) at 25° C. Form J of compound A is a dichloromethane (DCM) solvate, having an unidentified amount of water. Form J crystals are prepared by precipitating compound A in 2:1 dichloromethane/n-heptane (2:1).

Example 2. A Phase 1b/2 Study of Grapiprant, an EP4 Inhibitor, and Pembrolizumab, a PD-1 Checkpoint Inhibitor, in Patients with Advanced or Metastatic Post-PD-1/L1 Non-Small Cell Lung Cancer (NSCLC) Adenocarcinoma Overall Design:

This study is a multi-center, open-label, single-arm, Phase 1b/2 study to evaluate the safety and efficacy of grapiprant in combination with pembrolizumab in adult patients diagnosed with NSCLC who have been previously treated for a minimum of 12 weeks with any PD-1 or PD-L1 checkpoint inhibitor. Participant enrollment and continuous safety assessment will be dictated by an mTPI model. Decisions for dose escalation and de-escalation will be made by a safety review board (SRB) comprised of enrolling study investigators and the Sponsor. The starting grapiprant dose will be 300 mg twice a day (BID) unless lowered at the study initiation by the SRB. Dose escalation and confirmation will end after 14 participants have been treated at any of the selected doses found to be acceptable. Following the continuous safety assessment phase, additional participants up to a total trial size of 25 will be enrolled to assess efficacy. Participants, including those who achieve a complete response (CR), may receive treatment with grapiprant and pembrolizumab for up to 2 years or until they experience disease progression with clinical deterioration, unacceptable toxicity, or consent withdrawal, followed by 30- and 90-Day End of Treatment Follow-up visits after their last day of study treatment.

- Participants will be treated with grapiprant and pembrolizumab on Cycle 1 Day 1.
- PK samples will be taken as indicated on the Schedule of Events (SoE).
- Scans for tumor assessment will be assessed for all participants every 8 weeks (+/−7 days) from treatment initiation for the first 3 cycles, and then every 12 weeks (+/−7 days) thereafter, and at the discretion of the investigator.
- Participants will be instructed to maintain a normal diet during the Combination Treatment and will be encouraged to take grapiprant with food regularly as food is known to decrease common mild GI AEs in drugs of a similar class (COX-2 inhibitors). Morning food intake will be recorded in the medication administration diary on days when post-dose PK samples are drawn.
- Mandatory tumor biopsies will be collected in a subset of up to 10 evaluable participants deemed safe for repeated biopsies before Cycle 1 Day 1 and between the end of Cycle 1 and end of Cycle 3, ideally from the same tumor. A third tumor biopsy will be collected in any participant in the biopsy subgroup who has a partial response on tumor assessment, within a month of RECIST v1.1 response documentation, if safe to access, and discussed with the Sponsor.

Main Inclusion Criteria:

1. Male and female adult patients (≥18 years of age on day of signing informed consent) with a histologically confirmed non-small cell lung cancer (NSCLC) adenocarcinoma.
2. Advanced (stage IIIb) disease that is not amenable to curative intent treatment with concurrent chemoradiation and metastatic (stage IV) patients. There is no limit to the number of prior treatment regimens.
3. Patients must have progressed clinically and/or radiographically per RECIST v1.1 after receiving a PD-1 or PD-L1 antagonist for a minimum of 12 weeks. Note: Immunotherapy may have been given with or without chemotherapy and may have been used in any line, however no more than one prior regimen of immunotherapy is allowed.
4. Have measurable disease per RECIST v1.1 as assessed by the local site investigator/radiology. Lesions situated in a previously irradiated area are considered measurable if progression has been demonstrated in such lesions.
5. For biopsy subgroup (10 participants), disease that can be safely accessed via bronchoscopic, thoracoscopic or percutaneous biopsy for multiple core biopsies (minimum of 3 passes per biopsy) and participant is willing to provide tissue from newly obtain biopsies on study.
6. Have an Eastern Cooperative Oncology Group (ECOG) performance status of 0 to 1.
7. Have adequate organ function as defined in Table A below.
8. Willing to use contraception for women who are not postmenopausal and all men.
9. Be willing and able to provide written informed consent for the trial.

TABLE A

| Adequate Organ Function Laboratory Values | |
| --- | --- |
| System | Laboratory Value |
| Hematological | |
| ANC | ≥1500/µL |
| Platelets | ≥75,000/µL |
| Hemoglobin | ≥9.0 g/dL or ≥5.6 mmol/L[1] |
| Renal | |
| Creatinine OR Measured or calculated[2] creatinine clearance in mL/min (GFR can also be used in place of creatinine or CrCl) | ≤1.5 × ULN OR ≥40 mL/min for participant with creatinine levels >1.5 × institutional ULN |
| Hepatic | |
| Total bilirubin | ≤1.5 × ULN OR direct bilirubin ≤ULN for participants with total bilirubin levels >1.5 × ULN |
| AST (SGOT) and ALT (SGPT) | ≤2.5 × ULN (≤5 × ULN for participants with liver metastases) |

TABLE A-continued

| Adequate Organ Function Laboratory Values | |
| --- | --- |
| System | Laboratory Value |
| Coagulation | |
| INR OR PT aPTT | ≤1.5 × ULN unless participant is receiving anticoagulant therapy as long as PT or aPTT is within therapeutic range of intended use of anticoagulants |

ALT (SGPT) = alanine aminotransferase (serum glutamic pyruvic transaminase); ANC = absolute neutrophil count; aPTT = activated partial thromboplastin time; AST (SGOT) = aspartate aminotransferase (serum glutamic oxaloacetic transaminase); CrCl = creatinine clearance; GFR = glomerular filtration rate; INR = international normalized ratio; PT = prothrombin time; ULN = upper limit of normal.
[1]Criteria must be met without erythropoietin dependency and without packed red blood cell (pRBC) transfusion within last 2 weeks.
[2]Creatinine clearance in ml/min should be estimated by Cockcroft-Gault formula.
Note:
This table includes eligibility-defining laboratory value requirements for treatment; laboratory value requirements should be adapted according to local regulations and guidelines for the administration of specific chemotherapies.

Main Exclusion Criteria:

1. Current use of NSAIDs (eg, ibuprophen, naproxen), COX-2 inhibitors (eg, celecoxib) within 3 days before treatment initiation or at any time during the study unless used for management of AE or otherwise authorized by the medical director. Aspirin products should be limited to prophylactic cardiovascular doses unless discussed with the Sponsor.
2. Any patient with a known epidermal growth factor receptor (EGFR), anaplastic lymphoma kinase (ALK), or ROS gene alteration.
3. Any patient with a known BRAF gene mutation.
4. Any patient without a history of smoking (≤100 cigarettes lifetime) should be discussed with the Sponsor before enrolling.
5. History of severe hypersensitivity reactions to a PD-1/L1 antibody.
6. Has received prior systemic anti-cancer therapy including investigational agents within 4 weeks prior to treatment. Note: Participants must have recovered from all AEs due to previous therapies to ≤Grade 1 or baseline. Participants with ≤Grade 2 neuropathy may be eligible after discussion with the Sponsor.
7. Has received prior radiotherapy within 2 weeks of start of study treatment. Participants must have recovered from all radiation-related toxicities, not require corticosteroids, and not have had radiation pneumonitis. A 1-week washout is permitted for palliative radiation (≤2 weeks of radiotherapy) to non-central nervous system (CNS) disease.
   Note: No other concurrent antineoplastic treatment is permitted on study except for allowed local radiation of lesions for palliation only (to be considered non-target lesions after treatment)
   Note: If participant received surgery, they must have recovered fully from the toxicity and/or complications from the intervention prior to starting study treatment.
8. Has received a live vaccine within 30 days prior to the first dose of study treatment.
9. Participants taking strong CYP3A4 or P-glycoprotein inhibitors or inducers are excluded from the study unless they can be transferred to other medications within ≥5 half-lives prior to dosing.
10. Is currently participating in or has participated in a study of an investigational agent or has used an investigational device within 4 weeks prior to the first dose of study treatment. Note: Participants who have entered the follow-up phase of an investigational study may participate as long as it has been 4 weeks after the last dose of the previous investigational agent.
11. Has a diagnosis of immunodeficiency or is receiving chronic systemic steroid therapy (in dosing exceeding 10 mg daily of prednisone equivalent) or any other form of immunosuppressive therapy within 7 days prior the first dose of study treatment.
12. Has a known additional potentially life-threatening malignancy that is progressing or has required active treatment within the past 3 years. Note: Participants with basal cell carcinoma of the skin, squamous cell carcinoma of the skin, or carcinoma in situ (eg, breast carcinoma, cervical cancer in situ) that have undergone potentially curative therapy are not excluded.
13. Has known active CNS metastases and/or carcinomatous meningitis (clinically stable and/or previously treated inactive CNS metastases allowed).
14. Has an active autoimmune disease that has required systemic treatment in past 2 years (ie, with use of disease modifying agents, corticosteroids or immunosuppressive drugs). Replacement therapy (eg, thyroxine, insulin, or physiologic corticosteroid replacement therapy for adrenal or pituitary insufficiency) is not considered a form of systemic treatment and is allowed. Autoimmune diseases include but are not limited to inflammatory bowel disease (IBD) such as Crohn's disease and ulcerative colitis.
15. Has a history of (non-infectious) pneumonitis that required steroids or has current pneumonitis.
16. Has an active infection requiring systemic therapy.
17. Recent (within the last 12 months) or current GI ulcer or colitis or non-immune colitis.
18. Has a known history of human immunodeficiency virus (HIV) infection.
19. Has a known history of Hepatitis B or known active Hepatitis C virus infection.
20. Clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.
21. Has a history or current evidence of any condition, therapy, or laboratory abnormality that might confound the results of the study, interfere with the participant's participation for the full duration of the study, or is not in the best interest of the participant to participate, in the opinion of the treating investigator.
22. Has known psychiatric or substance abuse disorders that would interfere with cooperating with the requirements of the study.
23. A woman of childbearing potential (WOCBP) who has a positive pregnancy test prior to treatment.
24. Is breastfeeding or expecting to conceive or father children within the projected duration of the study.
Number of Participants:
Approximately 30 patients from approximately 3 to 6 study centers in the United States will be screened to enroll 25 participants in this study. Enrollment is defined as the time of initiation of the first dose of study treatment.
Participants who are withdrawn from treatment during the first cycle (ie, dose-limiting toxicity [DLT] period) for reasons other than AEs will be replaced
Intervention Groups and Duration:
A cycle of treatment will be defined as every 3 weeks (Q3W).

Participants will receive the combination of grapiprant and pembrolizumab beginning on Cycle 1 Day 1.
The dose of grapiprant will be 300 mg administered orally BID (daily dose taken at 8- to 12-hour intervals, preferably with food).
The pembrolizumab dose will be 200 mg IV Q3W.
Dose and schedule adjustments, corticosteroid administration, and monitoring plan are described in the protocol.
Participants with a DLT within the first cycle will have their dose of both grapiprant and pembrolizumab held until amelioration of their toxicities and be reduced from their existing dose of grapiprant by either 50 mg BID or 100 mg BID unless discussed with the Sponsor.
Participants who experience a first intolerable treatment-emergent adverse event (TEAE) after the first cycle will have their dose of grapiprant and pembrolizumab held until amelioration of their toxicities and be reduced from their existing grapiprant dose by 50 mg BID increments. Switching grapiprant administration to a 2 week on/1 week off schedule is also to be considered by the investigator depending on the nature of the TEAE.
Any participant who requires a decrease in the grapiprant dose below 150 mg BID will have grapiprant treatment discontinued, but may continue to receive pembrolizumab if clinical benefit has been demonstrated.
Participants with Grade 2 or greater dyspepsia for 5 or more days may, at the judgment of the investigator, institute ranitidine at 75 mg orally BID, to be taken 2 hours after the dose of grapiprant, until symptoms abate.
Additional dose adjustment and monitoring plan is described in the protocol.
Participants, including those who achieve a CR, may receive grapiprant and pembrolizumab until they experience disease progression with clinical deterioration, unacceptable toxicity, or consent withdrawal, followed by 30- and 90-Day End of Treatment Follow-up visits after their last day of study treatment.
The duration of the study for each participant will include a Screening period for inclusion in the study of up to 28 days, courses of Combination Treatment cycles repeated every 21 days for a maximum of 35 cycles (up to 2 years), and End of Treatment Follow-up visits at 30 and 90 days following the last day of study treatment administration. The End of Treatment 90-Day Follow-up visit will be considered as the End of Study visit.
Dose de-escalation for all participants will take place any time safety rules indicate (eg, if 4 participants or more participants out of the first 6 participants experiences a DLT). Participants already enrolled and receiving drug without severe AEs may be permitted to receive additional doses at the original dose level after discussion with the Sponsor.
The expected enrollment period is 15 months. The study cut-off date is defined as the date when all the participants have either completed 16 weeks of treatment (ie, until the second tumor assessment) or discontinued the study treatment. The participants who continue to receive the study treatment after the study cut-off date will be followed and appropriate statistical analysis (listings or updated tables for safety, drug exposure and activity) will be performed when all the participants have discontinued the study treatment.
Statistical Considerations:
Determination of the sample size: The combination side-effect profile is expected to be similar to pembrolizumab alone.

The recommend sample size for the mTPI design is n=k*(d+1) (Ji and Wang, J Clin Oncol. 2013; 31(14):1785-91). If 8 subjects are dosed per dose level (k=8) and there are 2 doses tested (d=2), then it is anticipated that 24 subjects will be required. If 1 dose is tested, then it is anticipated that n=16 subjects will be needed. Dose escalation and confirmation will end after 14 participants have been treated at any of the selected doses found to be acceptable. Following the continuous safety assessment phase, additional subjects up to a total trial size of 25 will be assessed to establish an estimate of efficacy. There is no formal hypothesis testing or adjustment for multiplicity.

General statistical approach: Descriptive analysis of safety parameters will be performed on the whole treated population, defined as all participants exposed to at least one dose of grapiprant. Type, frequency, seriousness and relatedness of TEAEs will be analyzed according to Medical Dictionary for Regulatory Activities (MedDRA). Laboratory abnormalities will be analyzed according to National Cancer Institute Common Terminology Criteria for Adverse Events (NCI-CTCAE v5.0).

Pharmacokinetic Analyses: PK parameters of grapiprant will be summarized using descriptive statistics by dose level and time since last dose. The plasma PK of grapiprant will be described for the Cmax and AUC PK parameters. Any additional PK analyses will be described in the statistical analysis plan (SAP).

Population PK and Exposure-Response Analyses: Data from this study will be included with data collected from previous studies in a population PK analysis. The influence of covariates (eg, body weight, age, sex, race, and concomitant medications) on PK parameters will be investigated, if necessary and appropriate.

Additional exploratory PK and/or exposure-response modeling may be applied to the data, as appropriate.

Results of PK and/or any population PK or exposure-response analyses may be reported outside the clinical study report.

Efficacy analysis: Anti-tumor efficacy data will be descriptively presented on the evaluable response population including participants who had a disease assessment at screening and at a minimum one other time point during the study treatment.

The following estimate and confidence intervals (CIs) are meant to provide an overview of the precision of the ORR estimate under several scenarios.

If 1/25 subjects respond, the mean (95% CI) is 0.04 (0.0020, 0.1761).

If 2/25 subjects respond, the mean (95% CI) is 0.08 (0.0144, 0.2310).

If 3/25 subjects respond, the mean (95% CI) is 0.12 (0.0335, 0.2817).

If 4/25 subjects respond, the mean (95% CI) is 0.16 (0.0566, 0.3296).

If 5/25 subjects respond, the mean (95% CI) is 0.20 (0.0823, 0.3754).

If 8/25 subjects respond, the mean (95% CI) is 0.32 (0.1703, 0.5036)

Example 3. A Phase 1b Study of Grapiprant, an EP4 Inhibitor, and Pembrolizumab, a PD-1 Checkpoint Inhibitor in Patients with Advanced or Progressive Microsatellite Stable (MSS) Colorectal Cancer (CRC)

Overall Design: The study is a multi-center, open-label, single-arm, Phase 1b, safety, and efficacy study of grapiprant in combination with pembrolizumab in adult patients with advanced or progressive MSS CRC. This is the first study combining grapiprant with a PD-1 antibody (pembrolizumab), therefore, participant enrollment and continuous safety assessment will be dictated by an mTPI model. The Combination Treatment period will consist of 35 cycles (up to 2 years). The study also includes a one-week Single Agent Run-in period for the purpose of assessing pharmacodynamics of grapiprant as a single agent, as well as in combination with pembrolizumab in the following Combination Treatment period. Participants enrolled into Cohort 1 will be treated with grapiprant during the Single Agent Run-in period and all participants enrolled into Cohort 1 and Cohort 2 will receive treatment with grapiprant and pembrolizumab during the Combination Treatment period. Approximately 30 patients are planned to be screened for this study to allow up to 15 participants for enrollment into Cohort 1 and up to 10 participants for enrollment into Cohort 2. Cohort 1 will enroll participants prior to enrollment of participants into Cohort 2. Following the continuous safety assessment phase, enrollment of additional participants, up to a total trial size of 25 participants, will be assessed to establish an estimate of efficacy.

Single Agent Run-in Period: Cohort 1

Participants will be treated for 1 week with the pharmacologically active dose of grapiprant as a single agent. A starting dose of Grapiprant 300 mg will be administered orally twice a day (BID).

Participants will be instructed to maintain a normal diet during the Single Agent Runin and will be encouraged to take grapiprant with food regularly as food is known to decrease common mild GI AEs in drugs of a similar class (COX-2 inhibitors).

A mandatory pre-treatment tumor biopsy will be collected for participants who are deemed safe for repeated biopsies in Cohort 1 before the first dose of grapiprant on Day 1 and a mandatory post-treatment tumor biopsy will be obtained between Day 5 of the Single Agent Run-in period and pre-dose of pembrolizumab on Cycle 1 Day 1 of the Combination Treatment period, ideally from the same tumor.

PK samples will be taken as indicated on the Schedule of Events (SoE).

Combination Treatment Period: Cohorts 1 and 2

All participants in Cohorts 1 and 2 will be treated with a starting dose of grapiprant 300 mg administered orally BID unless a dose de-escalation occurs and a fixed dose of pembrolizumab administered 200 mg IV every 3 weeks (Q3W) beginning on Cycle 1 Day 1.

PK samples will be taken as indicated on the SoE.

For participants deemed safe for repeated biopsies in Cohort 2, a mandatory pretreatment tumor biopsy will be collected during screening prior to receiving the first dose of either agent on Cycle 1 Day 1 and a mandatory second tumor biopsy will be collected between the end of Cycle 1 and the end of Cycle 3, ideally from the same tumor. A third tumor biopsy will be collected for any participant who has a partial response (PR) on tumor assessment, within a month of Response Evaluation Criteria in Solid Tumors version 1.1 (RECIST v1.1) response documentation, unless a biopsy has already been obtained within a month of the response or otherwise discussed with the medical director.

Scans for tumor assessment will be assessed for all participants (Cohorts 1 and 2) every 8 weeks (+/−7 days) from treatment initiation for the first 3 cycles, and then every 12 weeks (+/−7 days) thereafter, and at the discretion of the investigator.

Participants will be instructed to maintain a normal diet during the Combination Treatment and will be encouraged to take grapiprant with food regularly as food is known to decrease common mild GI AEs in drugs of a similar class (COX-2 inhibitors). Morning food intake will be recorded in the medication administration diary on days when post-dose PK samples are drawn.

Main Inclusion Criteria:

1. Male and female adult patients (≥18 years of age on day of signing informed consent) with a histologically confirmed advanced, metastatic, or progressive CRC that is MSS. Microsatellite stability is based on prior polymerase chain reaction (PCR), Next-Gen sequencing, or immunohistochemistry results per institutional standards.

2. Patient has received at least two prior lines of therapy for advanced or metastatic CRC, at least one of which included fluorouracil. Adjuvant therapy will be counted as a line of therapy only if progression occurs within 6 months of its completion. There is no limit to the number of prior treatment regimens.

3. Have measurable disease per RECIST v1.1 as assessed by the local site investigator/radiology. Lesions situated in a previously irradiated area are considered measurable if progression has been demonstrated in such lesions.

4. Accessible tumor that can be safely accessed for multiple core biopsies and patient is willing to provide tissue from newly obtain biopsies before and during treatment.

5. Have an Eastern Cooperative Oncology Group (ECOG) performance status of 0 to 1.

6. Have adequate organ function as defined in Table A above.

7. Be able to swallow and absorb oral tablets

8. Willing to use contraception for women who are not postmenopausal and all men.

9. Be willing and able to provide written informed consent for the trial.

Main Exclusion Criteria:

1. Has received prior therapy with an anti-PD-1, anti-PD-L1, or anti-PD-L2 agent or with an agent directed to another stimulatory or co-inhibitory T-cell receptor (eg, CTLA-4, OX 40, CD137).

2. Current use of NSAIDs (eg, ibuprophen, naproxen), COX-2 inhibitors (eg, celecoxib) within 3 days before treatment initiation or at any time during the study unless used for management of AE or otherwise authorized by the Sponsor. Aspirin products should be limited to prophylactic cardiovascular doses unless discussed with the Sponsor.

3. History of severe hypersensitivity reactions to chimeric or humanized antibodies.

4. Has received prior systemic anti-cancer therapy including investigational agents within 4 weeks prior to treatment, or 5 half-lives, whichever is shorter. Participants must have recovered from all AEs due to previous therapies to ≤Grade 1 or baseline. Participants with ≤Grade 2 neuropathy may be eligible after discussion with the Sponsor. If participant received major surgery, they must have fully recovered from the toxicity and/or complications from the intervention prior to starting study treatment.

5. Has received prior radiotherapy within 2 weeks of start of study treatment. Participants must have recovered from all radiation-related toxicities, not require corticosteroids, and not have had radiation pneumonitis. A 1-week washout is permitted for palliative radiation (≤2 weeks of radiotherapy) to non-central nervous system (CNS) disease. No other concurrent antineoplastic treatment is permitted on study except for allowed local radiation of lesions for palliation only (to be considered non-target lesions after treatment).

6. Has received a live vaccine within 30 days prior to the first dose of study drug.

7. Participants taking strong CYP3A4 or P-glycoprotein inhibitors or inducers are excluded from the study unless they can be transferred to other medications within ≥5 half-lives prior to dosing.

8. Is currently participating in or has participated in a study of an investigational agent or has used an investigational device within 4 weeks prior to the first dose of study treatment. Participants who have entered the follow-up phase of an investigational study may participate as long as it has been 4 weeks after the last dose of the previous investigational agent.

9. Has a diagnosis of immunodeficiency or is receiving chronic systemic steroid therapy (in dosing exceeding 10 mg daily of prednisone equivalent) or any other form of immunosuppressive therapy within 7 days prior the first dose of study drug.

10. Has a known additional potentially life-threatening malignancy that is progressing or has required active treatment within the past 3 years. Participants with basal cell carcinoma of the skin, squamous cell carcinoma of the skin, or carcinoma in situ (eg, breast carcinoma, cervical cancer in situ) that have undergone potentially curative therapy are not excluded.

11. Has known active CNS metastases and/or carcinomatous meningitis. Participants with previously treated brain metastases may participate provided they are radiologically stable, ie, without evidence of progression for at least 4 weeks by repeat imaging (note that the repeat imaging should be performed during study screening), and/or clinically stable and without requirement of steroid treatment for at least 14 days prior to first dose of study treatment.

12. Has an active autoimmune disease that has required systemic treatment in past 2 years (ie, with use of disease modifying agents, corticosteroids or immunosuppressive drugs). Replacement therapy (eg, thyroxine, insulin, or physiologic corticosteroid replacement therapy for adrenal or pituitary insufficiency) is not considered a form of systemic treatment and is allowed. Autoimmune diseases include but are not limited to inflammatory bowel disease (IBD) such as Crohn's disease and ulcerative colitis.

13. Has a history of (non-infectious) pneumonitis that required steroids or has current pneumonitis.

14. Has an active infection requiring systemic therapy.

15. Recent (within the last 12 months) or current GI ulcer or non-immune colitis.

16. Has a known history of human immunodeficiency virus (HIV) infection.

17. Has a known history of Hepatitis B or known active Hepatitis C virus infection.

18. Clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.

19. Has a history or current evidence of any condition, therapy, or laboratory abnormality that might confound the results of the study, interfere with the participant's participation for the full duration of the study, or is not in the best interest of the participant to participate, in the opinion of the treating investigator.

20. Has known psychiatric or substance abuse disorders that would interfere with cooperating with the requirements of the study.

21. A woman of childbearing potential (WOCBP) who has a positive pregnancy test prior to treatment.

22. Is breastfeeding or expecting to conceive or father children within the projected duration of the study.

Number of Participants:

Approximately 30 patients from approximately 3 to 5 study centers in the United States will be screened to enroll 25 participants (15 participants in Cohort 1 and 10 participants in Cohort 2) in this study. Enrollment is defined as the time of initiation of the first dose of study drug. Participants who are withdrawn from treatment during the Single-Agent Run-in (Cohort 1) or the first cycle of combination (ie, dose-limiting toxicity [DLT] period) for reasons other than AEs will be replaced.

Treatment Groups and Duration:

A cycle of treatment will be defined as Q3W.

The pembrolizumab dose will be 200 mg IV Q3W.

Dose and schedule adjustments, corticosteroid administration, and monitoring plan are described in the protocol.

The dose of grapiprant will be 300 mg administered orally BID (daily dose taken at 8- to 12-hour intervals, preferably with food).

Participants with a DLT within the first cycle will have their dose held until amelioration of their toxicities and be reduced from their existing dose by 50 mg BID or 100 mg BID unless discussed with the Sponsor.

Participants who experience a first intolerable treatment-emergent adverse event (TEAE) after the first cycle will have their dose held until amelioration of their toxicities and be reduced from their existing dose at 50 mg BID increments. Switching grapiprant administration to a 2 week on/1 week off schedule is also to be considered by the investigator depending on the nature of the TEAE.

Any participant who requires a decrease in the grapiprant dose below 150 mg BID will have grapiprant treatment discontinued, but may continue to receive pembrolizumab if clinical benefit has been demonstrated.

Participants with Grade 2 or greater dyspepsia for 5 or more days may, at the judgment of the investigator, institute ranitidine at 75 mg orally BID, to be taken 2 hours after the dose of grapiprant, until abdominal discomfort abates.

Additional dose adjustment and monitoring plan is described in the protocol.

Participants, including those who achieve a complete response (CR), may receive treatment with grapiprant and pembrolizumab for up to 2 years or until they experience disease progression, unacceptable toxicity, or consent withdrawal, followed by 30- and 90-Day End of Treatment Follow-up visits after their last day of study drug.

The duration of the study for each participant will include a screening period for inclusion in the study of up to 28 days, a 7-day Single Agent Run-in (for Cohort 1 only), courses of Combination Treatment cycles repeated every 21 days, and End of Treatment Follow-up visits at 30 and 90 days following the last study drug administration for all participants. Participants may continue to receive the study drugs for a maximum of 35 cycles (up to 2 years).

Dose de-escalation for all participants will take place any time safety rules indicate (eg, if 3 or more participants out of the first 5 participants experiences a DLT). Participants already enrolled and receiving drug without severe AEs may be permitted to receive additional doses at the original dose level after discussion with the Sponsor.

The expected enrollment period is 10 months. The study cut-off date is defined as the date when all the participants have either completed 16 weeks of treatment (ie., until the second tumor assessment) or discontinued the study drug. The participants who continue to receive the study drug after the study cut-off date will be followed and appropriate statistical analysis (listings or updated tables for safety, drug exposure and activity) will be performed when all the participants have discontinued the study drug.

Statistical Considerations:

Determination of the sample size: The combination side-effect profile is expected to be similar to pembrolizumab alone.

The recommend sample size for the mTPI design is $n=k*(d+1)$ (Ji and Wang, J Clin Oncol. 2013; 31(14):1785-91). If 8 subjects are dosed per dose level (k=8) and there are 2 doses tested (d=2), then it is anticipated that 24 subjects will be required. If 1 dose is tested, then it is anticipated that n=16 subjects will be needed. Following the continuous safety assessment phase, additional subjects up to a total trial size of 25 will be assessed to establish an estimate of efficacy. There is no formal hypothesis testing or adjustment for multiplicity.

General statistical approach: Descriptive analysis of safety parameters will be performed on the whole treated population, defined as all participants exposed to at least one dose of grapiprant. Specifically, both study cohorts will be pooled, and by-cohort analyses will not be performed. Type, frequency, seriousness and relatedness of TEAEs will be analyzed according to Medical Dictionary for Regulatory Activities (MedDRA). Laboratory abnormalities will be analyzed according to National Cancer Institute Common Terminology Criteria for Adverse Events (NCI-CTCAE) v5.0.

Pharmacokinetic Analyses: PK parameters of grapiprant will be summarized using descriptive statistics by dose level and time since last dose. The plasma PK of grapiprant will be described for the Cmax and AUC PK parameters. Any additional PK analyses will be described in the statistical analysis plan (SAP).

Population PK and Exposure-Response Analyses: Data from this study will be included with data collected from previous studies in a population PK analysis. The influence of covariates (eg, body weight, age, sex, race, and concomitant medications) on PK parameters will be investigated, if necessary and appropriate.

Additional exploratory PK and/or exposure-response modeling may be applied to the data, as appropriate.

Results of PK and/or any population PK or exposure-response analyses may be reported outside the clinical study report.

Efficacy analysis: Anti-tumor efficacy data will be descriptively presented on the evaluable response population including participants who had a disease assessment at screening and at a minimum one other time point during the study treatment.

An informal interim analysis will be conducted to enable future trial planning at the Sponsor's discretion and data will be examined on a continuous basis to allow for dose finding decisions.

Example 4. Anti-Tumor Activity of Compound B in the CT-26 Colon Adenocarcinoma Mouse Model The antitumor activity of Compound B as a single agent and combined with a mouse anti-PD-1 antibody was evaluated in the CT-26 mouse colon adenocarcinoma model grown in BALB/c mice. Mice were inoculated subcutaneously in the right flank with $5 \times 10^5$ tumor cells. When tumors reached an average size of 71 mm$^3$ (6 days after tumor cell inoculation) dosing was initiated. The dosing regimens in the 8 separate cohorts comprising 10 mice each are as follows:

| Group | Treatment | Dose per administration | Dose volume per administration | Dosing Schedule/Days | Administration route |
|---|---|---|---|---|---|
| 1 | Vehicle(0.5% MC) | — | 10 ul/g | BID × 3+ weeks | p.o. |
|   | Rat IgG2(Isotype matched) | 10 mg/kg | 10 ul/g | Day 1, 4, 8, 11, 15 | i.p. |
| 2 | Anti-PD1 | 10 mg/kg | 10 ul/g | Day 1, 4, 8, 11, 15 | i.p. |
| 3 | Compound B | 15 mg/kg | 10 ul/g | QD × 3+ weeks | p.o. |
| 4 | Compound B | 15 mg/kg | 10 ul/g | BID × 3+ weeks | p.o. |
| 5 | Compound B | 15 mg/kg | 10 ul/g | QD × 3+ weeks | p.o. |
|   | Anti-PD1 | 10 mg/kg | 10 ul/g | Day 1, 4, 8, 11, 15 | i.p. |
| 6 | Compound B | 15 mg/kg | 10 ul/g | BID × 3+ weeks | p.o. |
|   | Anti-PD1 | 10 mg/kg | 10 ul/g | Day 1, 4, 8, 11, 15 | i.p. |

During the period of dosing, the tumor growth kinetics in mice treated with Compound B dosed at 15 mg/kg once daily (QD) and BID were not notably different from the vehicle treated mice (FIG. 1). The tumor growth kinetics in mice treated with Compound B dosed at 15 mg/kg QD and BID combined with anti-PD-1 were also not notably different mice treated with single agent anti-PD-1 during the treatment period. Each dosing regimen was tolerated by the mice as indicated by an average increase in body weight in each cohort during the treatment period and after treatment was discontinued.

Figure 2:
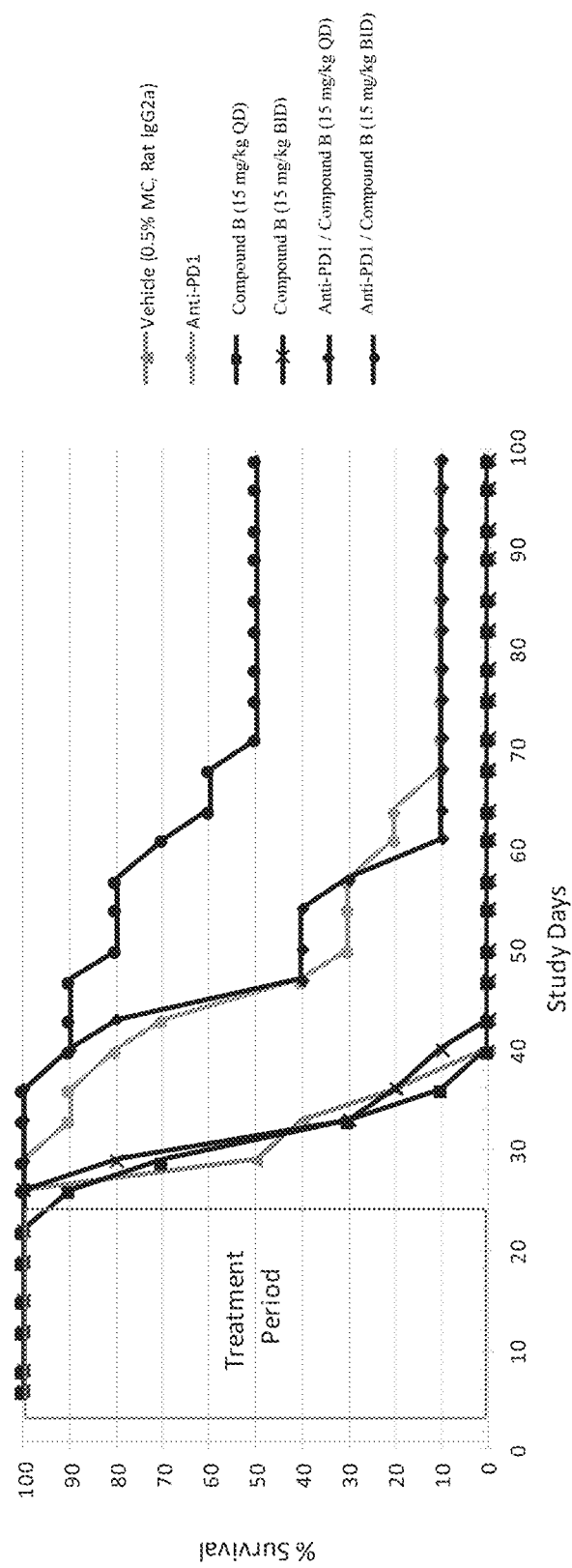
FIG. 2 depicts Kaplan-Meier Curve of Tumor Bearing Mice. Kaplan-Meier curve of tumor-bearing mice treated with vehicle (0.5% methylcellulose and IgG2a), anti-PD-1, or Compound B at 15 mg/kg QD and BID alone or in combination with anti-PD-1. Mice were monitored out 99 days after tumor inoculation, and animals were sacrificed when tumor sizes exceeded 3000 $mm^3$.

After treatment was discontinued, mice treated with Compound B at 15 mg/kg BID in combination with anti-PD-1 demonstrated decreased growth kinetics relative to anti-PD-1 (FIG. 1) and improved survival (FIG. 2). After continuing to monitor the mice for 99 days after tumor inoculation, 5 out of 10 mice were still alive (4 tumor free) whereas only 1 out of 10 mice treated with anti-PD-1 as a single agent and 1 out of 10 mice in the Compound B was still alive and tumor free. These data suggest that Compound B when combined with anti-PD-1 leads to an improved long term antitumor response.

CT26 tumor cells were inoculated into 6 tumor-naive mice or complete responders of CT26 tumor-bearing mice previously treated with Compound B and anti-PD-1 alone or in combination. The data show that the mice with a complete response decreased the growth of CT26 relative to naive mice suggesting there was a vaccinal effect in the cured mice.

The antitumor activity of Compound B as a single agent and combined with a mouse anti-PD1 antibody was evaluated in the CT-26 mouse colon adenocarcinoma model grown in BALB/c mice in an additional experiment. Mice were inoculated subcutaneously in the right flank with $5 \times 10^5$ tumor cells. When tumors reached an average size of 91 mm$^3$ dosing was initiated. The dosing regimens in the 4 separate cohorts comprising 7 mice each are as follows:

| Group | Treatment | Dose per administration | Dose volume per administration | Dosing Schedule/Days | Administration route |
|---|---|---|---|---|---|
| 1 | Vehicle (0.5&MC) | — | 10 ul/g | BID × 17 days | po |
|   | PBS | — | 10 ul/g | BIW × 4 doses | ip |
| 2 | Compound B | 15 mg/kg | 10 ul/g | BID × 17 days | po |
|   | PBS | — | 10 ul/g | BIW × 4 doses | ip |
| 3 | Anti-PD1 | 10 mg/kg | 10 ul/g | BIW × 5 doses | ip |
|   | Vehicle | — | 10 ul/g | BID × 16 days | po |
| 4 | Compound B | 15 mg/kg | 10 ul/g | BID × 17 days | po |
|   | Anti-PD1 | 10 mg/kg | 10 ul/g | BIW × 5 doses | ip |

Figure 5:
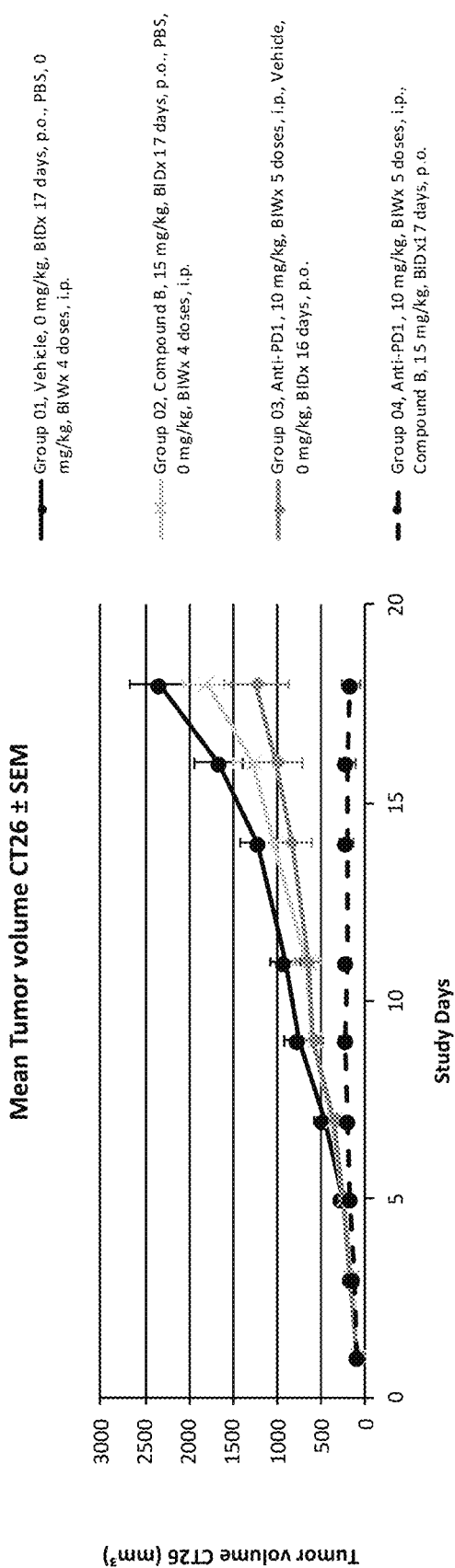
FIG. 5 depicts BALB/C mice bearing CT-26 tumors treated with vehicle (0.5% methylcellulose and PBS), anti-PD1, or Compound B at 15 mg/kg BID alone or in combination with anti-PD1. Mean tumor volumes ($mm^3$) and standard error of the mean (n=7/group) are shown.

During the period of dosing, the tumor growth kinetics in mice treated with Compound B dosed at 15 mg/kg twice daily (BID) and anti-PD1 were less than that of the vehicle group (FIG. 5). The tumor growth kinetics in mice treated with Compound B dosed at 15 mg/kg BID combined with anti-PD1 were lower than mice treated with either single agent. Each dosing regimen was tolerated by the mice as indicated by an average increase in body weight in each cohort during the treatment period.

Example 5. Anti-Tumor Activity of Compound B in the 4T1 Breast Cancer Mouse Model The antitumor activity of Compound B as a single agent and combined with a mouse anti-CTLA4 antibody was evaluated in the 4T1 mouse breast cancer model grown in BALB/c mice. Mice were inoculated subcutaneously in the right flank with $3 \times 10^5$ tumor cells. When tumors reached an average size of 100 mm$^3$ (7 days after tumor cell inoculation) dosing was initiated.

Figure 3:
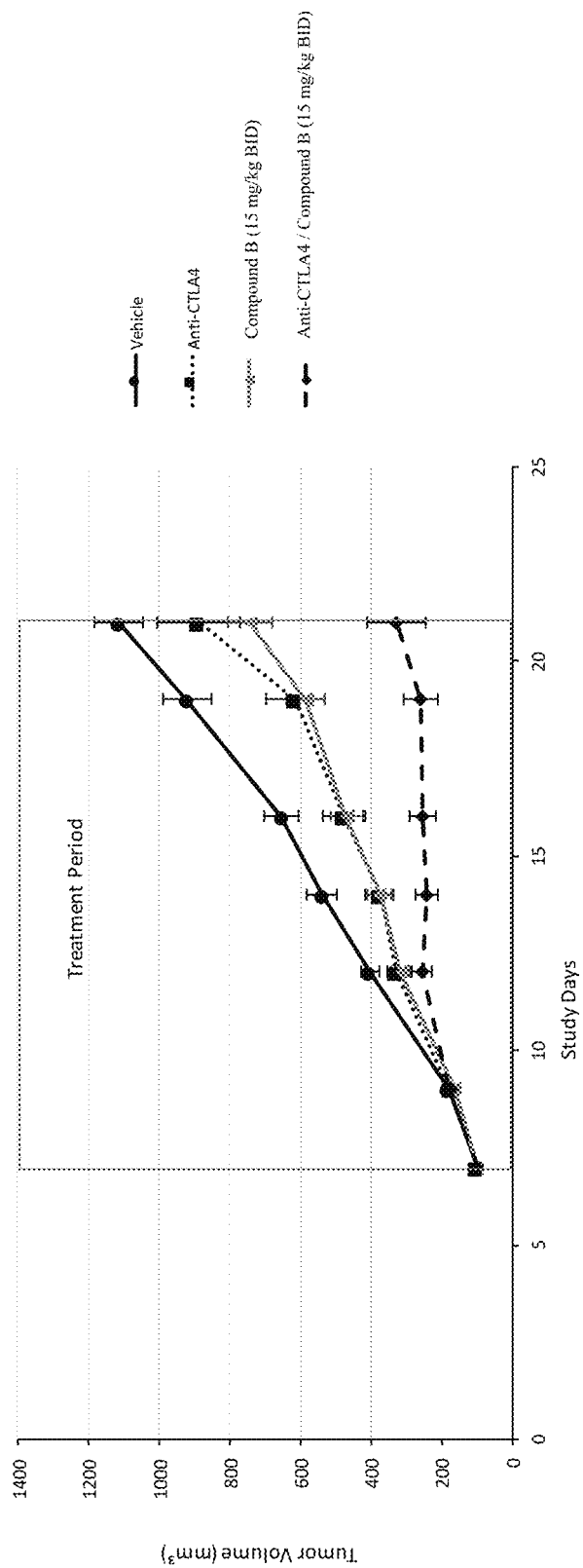
FIG. 3 depicts Tumor Growth Kinetics in BALB/C Mice Bearing 4T1 Tumors. BALB/C mice bearing 4T1 tumors were treated with vehicle, anti-CTLA4, or Compound B at 15 mg/kg BID alone or in combination with anti-CTLA41. Mean tumor volumes ($mm^3$) and standard error of the mean (n=10/group) are shown.

During the period of dosing, the tumor growth kinetics in mice treated with Compound B dosed at 15 mg/kg BID and anti-CTLA4 were decreased relative to the vehicle treated mice (FIG. 3). Moreover, the tumor growth kinetics in mice treated with Compound B and anti-CTLA4 combined was decreased relative to either agent when dosed alone. Each dosing regimen was tolerated by the mice as indicated by an average increase in body weight in each cohort during the treatment period and after treatment was discontinued.

Figure 4:
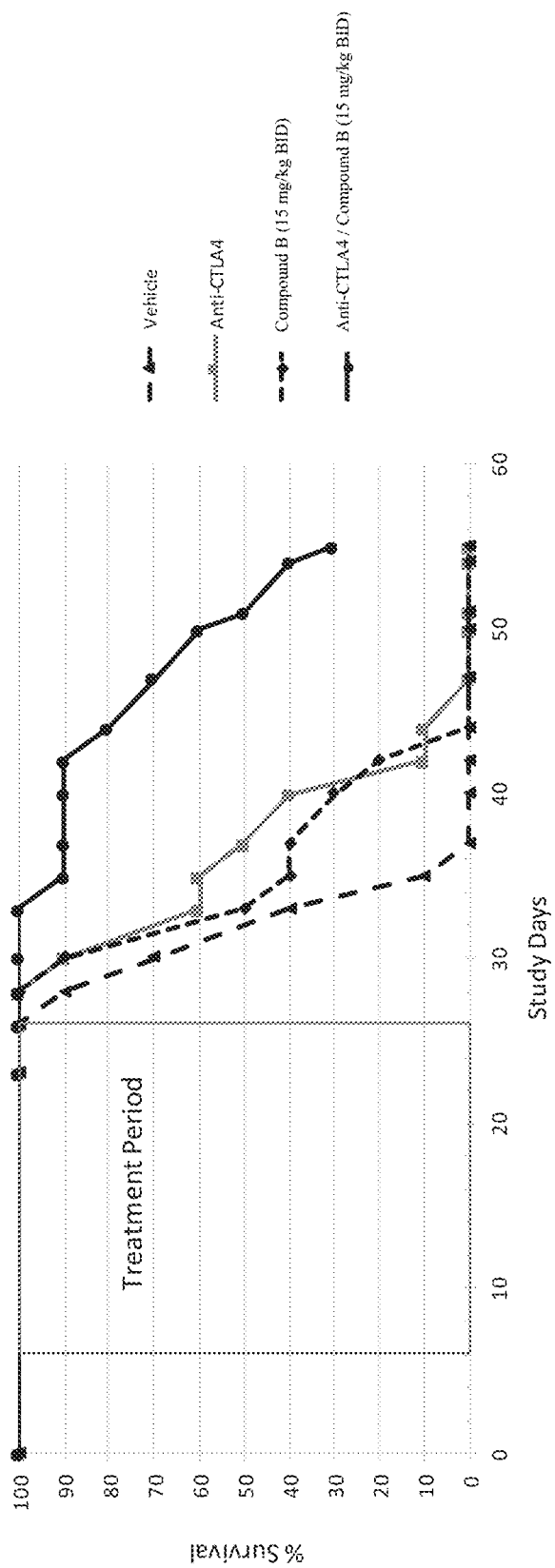
FIG. 4 depicts Kaplan-Meier Curve of Tumor-Bearing Mice Study. Kaplan-Meier curve of tumor-bearing mice treated with vehicle, anti-CTLA4, or Compound B at 15 mg/kg BID alone or in combination with anti-CTLA4. Mice were monitored for 41 days after tumor inoculation, and animals were sacrificed when tumor sizes exceeded 3000 $mm^3$.

After treatment was discontinued, mice treated with Compound B at 15 mg/kg BID in combination with anti-CTLA4 demonstrated improved survival rate relative to either single agent alone (FIG. 4). For example, after continuing to monitor the mice for 47 days after tumor inoculation, 7 of 10 mice treated with the combination were still alive whereas none of mice treated with either single agent alone was alive 47 days after tumor inoculation. 3 of 10 mice treated with the combination were still alive at the end of the study 55 days after tumor inoculation. These data suggest that the Compound B and anti-CTLA4 combination leads to an improved antitumor response relative to either agent alone.

The antitumor activity of Compound B as a single agent and combined with a mouse anti-PD1 antibody was evaluated in the 4T1 mouse breast cancer model grown in BALB/c mice in an additional experiment. Mice were inoculated subcutaneously in the right flank with $3 \times 10^5$ tumor cells. When tumors reached an average size of 97 mm³ dosing was initiated. The dosing regimens in the 4 separate cohorts comprising 7 mice each are as follows:

treated with either single agent. Each dosing regimen was tolerated by the mice as indicated by an average increase in body weight in each cohort during the treatment period.

Example 6. Effect of Compound B on Immune Cell Composition in the CT-26 Colon Adenocarcinoma Mouse Model The immune cell composition of Compound B as a single agent and combined with a mouse anti-PD1 antibody was evaluated in the CT-26 mouse colon adenocarcinoma model grown in BALB/c mice. Mice were inoculated subcutaneously in the right flank with $5 \times 10^5$ tumor cells. When tumors reached an average size of 85 mm³ dosing was initiated. The dosing regimens in the 4 separate cohorts comprising 10 mice each are listed as follows:

| Group | Treatment | Dose per administration | Dose volume per administration | Dosing Schedule/Days | Administration route | Number of mice |
|---|---|---|---|---|---|---|
| Group 1 | Vehicle (0.5&MC) | — | 10 ul/g | BID × 7 days | po | 10 |
| | PBS | — | 5 ul/g | Q3D × 3 doses | ip | |
| Group 2 | Compound B | 15 mg/kg | 10 ul/g | BID × 7 days | po | 10 |
| | PBS | — | 5 ul/g | Q3D × 3 doses | ip | |
| Group 3 | Anti-PD1 | 10 mg/kg | 5 ul/g | Q3D × 3 doses | ip | 10 |
| | Vehicle | — | 10 ul/g | BID × 7 days | po | |
| Group 4 | Compound B | 15 mg/kg | 10 ul/g | BID × 7 days | po | 10 |
| | Anti-PD1 | 10 mg/kg | 5 ul/g | Q3D × 3 doses | ip | |

After dosing animals for 7 days, tumors were resected and used to prepare single cell suspensions. Live cells representing tumor and immune cells were stained with cocktails of antibodies targeting multiple immune cell markers (anti-CD45, anti-CD3, anti-CD4, anti-CD8, anti-CD25, anti-FoxP3, anti-PD-1, anti-CD11c) conjugated to different fluorescent tags. The stained cells were fixed in 4% paraformaldehyde and quantified using a multi-color flow cytometer (Fortessa). The data was analyzed with FloJo software.

Figure 7:
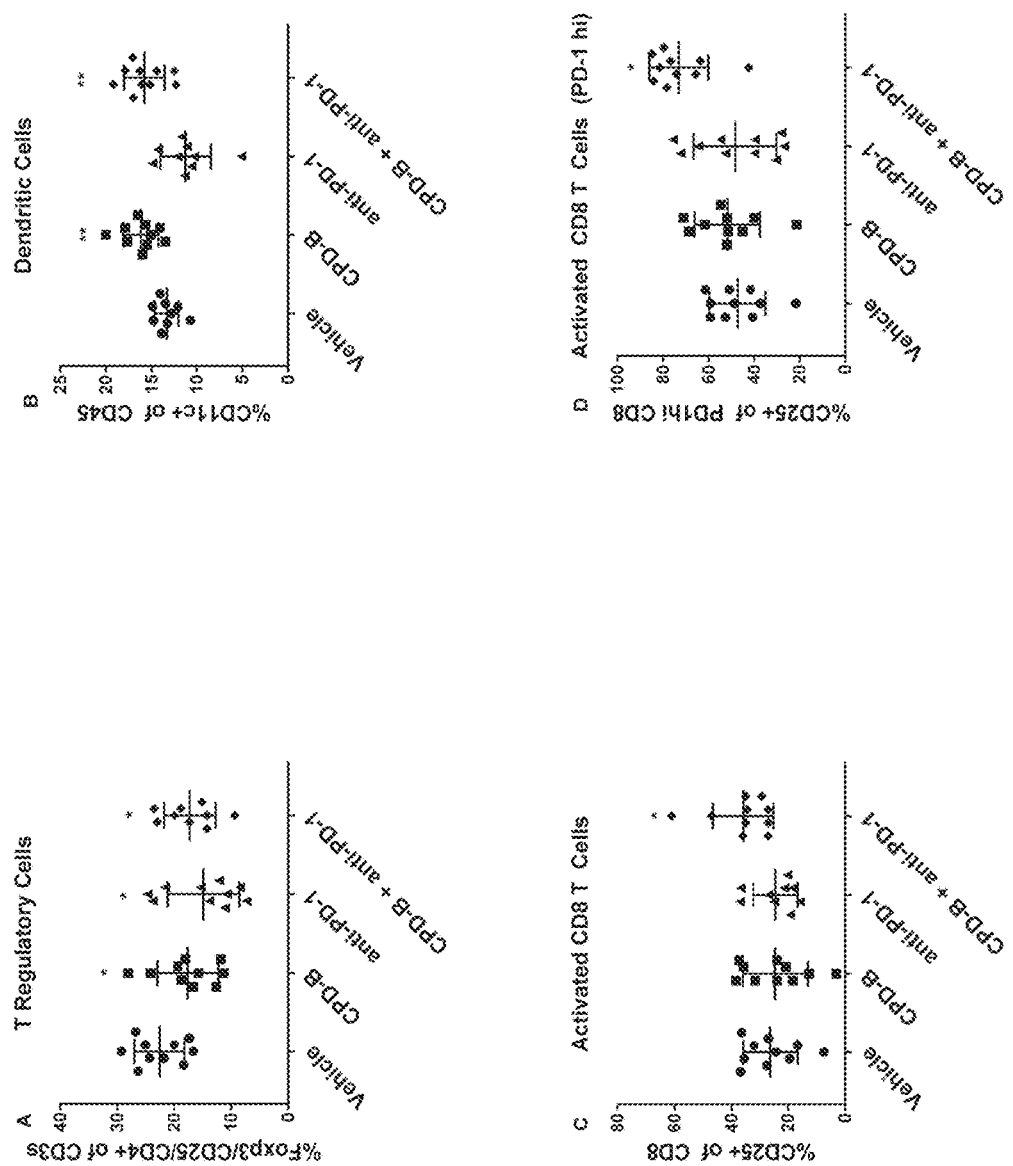
FIG. 7 depicts the immune cell composition of CT-26 tumors grown in BALB/c mice treated with vehicle (0.5% methylcellulose and PBS), anti-PD1, or Compound B (CPD-B) at 15 mg/kg BID alone or in combination with anti-PD1. The percentage of regulatory T cells (a), dendritic cells (b), activated T cells (c) and activated PD-1 high T cells (d) is shown. p values determined using a Student's T-test comparing vehicle to treated groups; *$p<0.05$, **$p<0.01$.

Compound B, anti-PD-1 and the combination of the 2 agents resulted in a significant decrease in regulatory T cells (CD45, CD4, FoxP3, CD25 positive) (FIG. 7a). Compound B dosed alone and with anti-PD-1 led to increased percentage of dendritic cells (CD45, CD11c positive), whereas

| Group | Treatment | Dose per administration | Dose volume per administration | Dosing Schedule/Days | Administration route |
|---|---|---|---|---|---|
| 1 | Vehicle (0.5&MC) | — | 10 ul/g | BID × 20 days | po |
| | PBS | — | 10 ul/g | BIW × 5 doses | ip |
| 2 | Compound B | 15 mg/kg | 10 ul/g | BID × 20 days | po |
| | PBS | — | 10 ul/g | BIW × 5 doses | ip |
| 3 | Anti-PD1 | 10 mg/kg | 10 ul/g | BIW × 6 doses | ip |
| | Vehicle | — | 10 ul/g | BID × 19 days | po |
| 4 | Compound B | 15 mg/kg | 10 ul/g | BID × 20 days | po |
| | Anti-PD1 | 10 mg/kg | 10 ul/g | BIW × 6 doses | ip |

Figure 6:
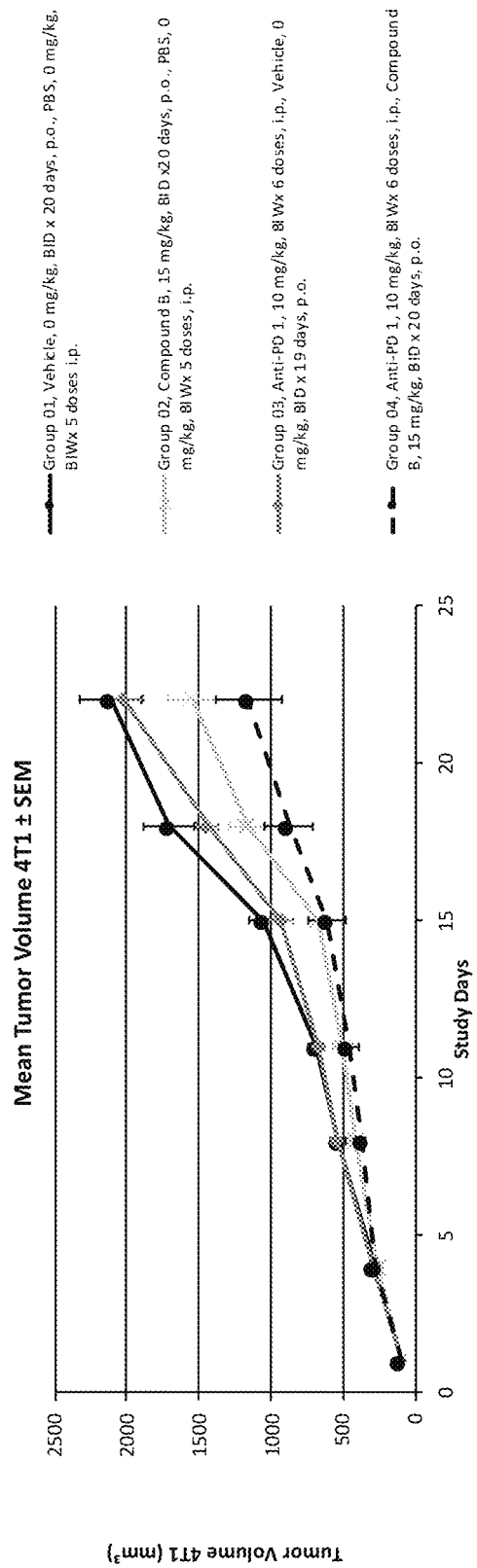
FIG. 6 depicts BALB/C mice bearing 4T1 tumors treated with vehicle (0.5% methylcellulose and PBS), anti-PD1, or Compound B at 15 mg/kg BID alone or in combination with anti-PD1. Mean tumor volumes ($mm^3$) and standard error of the mean (n=7/group) are shown.

During the period of dosing, the tumor growth kinetics in mice treated with Compound B dosed at 15 mg/kg twice daily (BID) was less than that of the vehicle group and anti-PD1 when dosed alone (FIG. 6). The tumor growth kinetics in mice treated with Compound B dosed at 15 mg/kg BID combined with anti-PD1 were lower than mice anti-PD-1 alone did not (FIG. 7b). The combination of Compound B with anti-PD-1 also led to increased percentage of activated T cells (CD45, CD3, CD8) by evaluating the CD25 expression where as either agent dosed alone did not (FIG. 7c). The percentage of CD25 was higher in T cells with increased levels of PD-1 (FIG. 7d). Collectively, these findings demonstrate that Compound B alone and when combined with anti-PD-1 antibodies alters the immune cell composition of CT-26 tumors indicative of an increased proinflammatory phenotype.

The invention claimed is:

1. A method for treating non-small cell lung cancer (NSCLC) or colorectal cancer (CRC) in a patient comprising administering to the patient an agent that inhibits prostaglandin EP4 receptor (EP4) activity in combination with an anti-PD-1 antibody, wherein the agent is

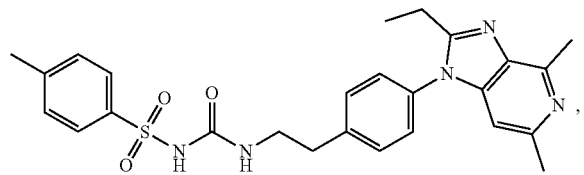

or a pharmaceutically acceptable salt thereof.

2. The method of claim 1, wherein the patient is a NSCLC patient.

3. The method of claim 2, wherein the NSCLC patient is an advanced (stage IIIb) and metastatic (stage IV) patient who has progressed clinically and/or radiographically per RECIST 1.1 (Response Evaluation Criteria in Solid Tumors).

4. The method of claim 1, wherein the patient is a CRC patient.

5. The method of claim 4, wherein the CRC patient is histologically confirmed advanced, metastatic, or progressive colorectal cancer (CRC).

6. The method of claim 1, wherein the anti-PD-1 antibody is Pembrolizumab.

7. The method of claim 2, wherein the NSCLC patient has been treated by PD-1/L1 immunotherapy for a minimum of 12 weeks.

8. The method of claim 2, wherein the NSCLC patient has pathologically diagnosed adenocarcinoma histology of NSCLC.

9. The method of claim 2, wherein the NSCLC patient has known PD-L1 positive status (>1%).

10. The method of claim 2, wherein the NSCLC patient does not have a history of severe hypersensitivity reactions to a PD-1/L1 antibody.

11. The method of claim 2, wherein the NSCLC patient does not have a known EGFR, ALK, or ROS gene alteration.

12. The method of claim 4, wherein the CRC patient is intolerable to 5-FU based therapy.

13. The method of claim 4, wherein the CRC patient does not have a history of severe hypersensitivity reactions to chimeric or humanized antibodies.

14. The method of claim 4, wherein the CRC patient has not received prior therapy with an anti-PD-1, anti-PD-L1, or anti-PD-L2 agent or with an agent directed to another stimulatory or co-inhibitory T-cell receptor.

15. The method of claim 1, wherein the patient does not have a recent history of inflammatory bowel disease (IBD), or non-infectious interstitial lung disease.

16. The method of claim 1, wherein the patient does not have current use of nonsteroidal anti-inflammatory drugs (NSAIDs) or cyclooxygenase-2 (COX-2) inhibitors.

17. The method of claim 1, wherein the patient does not have medical conditions requiring concomitant administration of strong CYP3A4 or P-glycoprotein inhibitors or inducers.

18. The method of claim 1, wherein the patient does not have a diagnosis of immunodeficiency.

19. The method of claim 1, wherein the agent, or a pharmaceutically acceptable salt thereof, is administered orally twice a day (BID) at a dose of 300 mg.

20. The method of claim 6, wherein Pembrolizumab is administered 200 mg IV every 3 weeks (Q3W).

* * * * *